US009695364B2

(12) United States Patent
Iversen

(10) Patent No.: US 9,695,364 B2
(45) Date of Patent: *Jul. 4, 2017

(54) PROCESS FOR PRODUCING LIQUID HYDROCARBON

(75) Inventor: Steen Brummerstedt Iversen, Vedbaek (DK)

(73) Assignee: STEEPER ENERGY APS, Vedbaek (DK)

(*) Notice: Subject to any disclaimer, the term of this patent is extended or adjusted under 35 U.S.C. 154(b) by 225 days.

This patent is subject to a terminal disclaimer.

(21) Appl. No.: 14/125,193

(22) PCT Filed: Jun. 11, 2012

(86) PCT No.: PCT/DK2012/000067
§ 371 (c)(1),
(2), (4) Date: Dec. 10, 2013

(87) PCT Pub. No.: WO2012/167790
PCT Pub. Date: Dec. 13, 2012

(65) Prior Publication Data
US 2014/0099691 A1 Apr. 10, 2014

(30) Foreign Application Priority Data

Jun. 10, 2011 (AU) ................. 2011902293
Jun. 11, 2011 (DK) ................. 2011 00444

(51) Int. Cl.
*C12P 5/02* (2006.01)
*C10G 1/04* (2006.01)
(Continued)

(52) U.S. Cl.
CPC .............. *C10G 1/047* (2013.01); *C10G 1/02* (2013.01); *C10G 1/04* (2013.01); *C10G 1/042* (2013.01);
(Continued)

(58) Field of Classification Search
CPC .......... C10G 1/047; C10G 1/042; C10G 1/04; C10G 1/02; C10G 1/065; C10G 2300/1014
See application file for complete search history.

(56) References Cited

U.S. PATENT DOCUMENTS 3,617,470 A 11/1971 Schlinger et al.
4,266,083 A 5/1981 Huang
(Continued)

FOREIGN PATENT DOCUMENTS

EP  0 073 355 A1  3/1983
EP  0 204 354 A1  12/1986
(Continued)

OTHER PUBLICATIONS

Tsukahara et al., Microalgal cultivation in a solution recovered from the low temperature catalytic gasification of the microalga. Journal of Bioscience and Bioengineering. vol. 91, No. 3 (2001) pp. 311-313.*

(Continued)

*Primary Examiner* — Kara Johnson
(74) *Attorney, Agent, or Firm* — Birch, Stewart, Kolasch & Birch, LLP

(57) ABSTRACT

The invention relates to a continuous process for converting carbonaceous material contained in one or more feedstocks into a liquid hydrocarbon product, said feedstocks including the carbonaceous material being in a feed mixture including one or more fluids, said fluids including water and further liquid organic compounds at least partly produced by the process in a concentration of at least 1% by weight, where the process comprises converting at least part of the carbonaceous material by pressurizing the feed mixture to a pressure in the range 50-400 bar, heating the feed mixture to a temperature in the range 250-500° C., and maintaining said pressurized and heated feed mixture in the desired pressure (Continued)

and temperature ranges in a reaction zone for a predefined time; cooling the feed mixture to a temperature in the range 25-200° C. and expanding the feed mixture to a pressure in the range of 1-70 bar, thereby causing the carbonaceous material to be converted to a liquid hydrocarbon product; separating a fraction comprising liquid hydrocarbon product, and leaving a residual fraction; feeding said residual fraction into a bioreactor for the production of biomass such as algae and/or bacteria such as cyano bacteria.

12 Claims, 19 Drawing Sheets

(51) Int. Cl.
 C10G 1/02 (2006.01)
 C10G 1/06 (2006.01)
 C10G 1/10 (2006.01)
 C12M 1/00 (2006.01)

(52) U.S. Cl.
 CPC .............. *C10G 1/065* (2013.01); *C10G 1/10* (2013.01); *C12M 43/02* (2013.01); *C12P 5/02* (2013.01); *C10G 2300/1003* (2013.01); *C10G 2300/1014* (2013.01); *C10G 2300/4018* (2013.01); *Y02P 30/20* (2015.11)

(56) References Cited

U.S. PATENT DOCUMENTS

| | | | |
|---|---|---|---|
| 4,485,003 | A | 11/1984 | Coenen et al. |
| 4,935,567 | A | 6/1990 | Yokoyama et al. |
| 6,132,478 | A | 10/2000 | Tsurui et al. |
| 7,262,331 | B2 | 8/2007 | Van De Beld et al. |
| 2008/0276800 | A1 | 11/2008 | Lourenco et al. |
| 2009/0126274 | A1 | 5/2009 | Vogel et al. |
| 2009/0206007 | A1 | 8/2009 | Allam |
| 2011/0023565 | A1 | 2/2011 | Yanik et al. |

FOREIGN PATENT DOCUMENTS

| | | |
|---|---|---|
| EP | 1 184 443 A1 | 3/2002 |
| EP | 1 862 527 A1 | 12/2007 |
| EP | 2 287 279 A1 | 2/2011 |
| WO | WO 81/00855 A1 | 4/1981 |
| WO | WO 95/14850 A1 | 6/1995 |
| WO | WO 2006/117002 A2 | 11/2006 |
| WO | WO 2009/015409 A1 | 2/2009 |
| WO | WO 2009/085700 A2 | 7/2009 |
| WO | WO 2009/099684 A2 | 8/2009 |
| WO | WO 2010/014010 A2 | 2/2010 |

OTHER PUBLICATIONS

Minowa et al., A novel microalgal system for energy production with nitrogen cycling. Fuel, vol. 78, No. 10 (Aug. 1999) pp. 1213-1215.*
Brown et al., Hydrothermal liquefaction and gasification of *Nannochloropsis* sp. Energy Fuels, vol. 24 (online May 10, 2010) pp. 3639-3646.*
Haiduc et al., SunCHem: an integrated process for the hydrothermal production of methane from microalgae and CO2 mitigation. Journal of Applied Phycology, vol. 21 (2009) pp. 529-541.*
Elliott et al., Process development for hydrothermal liquefaction of algae feedstocks in a continuous-flow reactor. Algal Research, vol. 2, No. 4 (Oct. 2013) pp. 445-454.*
Hammerschmidt et al., "Catalytic conversion of waste biomass by hydrothermal treatment", Fuel, vol. 90, 2011 (Available online Oct. 20, 2010), pp. 555-562.
Karagoz et al., "Comparative studies of oil compositions produced from sawdust, rice husk, lignin and cellulose by hydrothermal treatment", Fuel, vol. 84, 2005 (Available online Jan. 19, 2005), pp. 875-884.
Osada et al., "Catalytic Gasification of Wood Biomass in Subcritical and Supercritical Water", Combust. Sci. and Tech., vol. 178, 2006, pp. 537-552.
Peterson et al., "Thermochemical biofuel production in hydrothermal media: A review of sub- and supercritical water technologies", Energy Environ. Sci., vol. 1, 2008 (published online Jul. 9, 2008), pp. 32-65.
Luft, et al. "Safety and Control in High Pressure Plant Design and Operation", In High Pressure Process Technology: Fundamentals and Applications; Bertucco, A. and Vetterm G., Eds.; Elsevier: Amsterdam, 2001; vol. 9; pp. 405-406.
Outland, J.S., "Applications of Mechanical Vapor Recompression to Evaporation and Crystallization", Proceedings from the Seventeenth Industrial Energy Technology Conference, Houston, TX (Apr. 5-6, 1995); pp. 67-70.
Sinnott, R.K.; "Chemical Engineering Design"; 4th ed.; Elsevier; Oxford (2005), p. 101.
United States Environmental Protection Agency, "Sugar Cane Processing" [online], Jun. 1997 (retrieved on Aug. 20, 2015), retrieved from the Internet: <URL:http://www.epa.gov/ttn/chief/ap42/ch09/final/c9s10-1a.pdf>.
Wiebe et al. "The Solubility of Carbon Dioxide in Water at Various Temperatures from 12 to 40 degrees C and at Pressures to 500 Atmospheres. Critical Phenomena", J. Am. Chem. Soc., 62 (1940), pp. 815-817.

* cited by examiner

PROCESS FOR PRODUCING LIQUID HYDROCARBON

FIELD OF THE INVENTION

The present invention relates to the field of producing liquid hydrocarbons from carbonaceous materials. In particular, it relates to an improved process and apparatus for doing so in an efficient, economical and environmentally sustainable way.

BACKGROUND OF THE INVENTION

The world is facing fluctuations in crude oil prices as well as challenges to energy security, economic stability and growth. Further environmental concerns related to climate change due to the 'greenhouse effect' is coming more and more in focus. Furthermore a number of conventional energy sources such as oil are being depleted. This calls for a more efficient and sustainable use of resources, including non-conventional and alternative resources.

Hence, there is a large and increasing global interest in new technologies for the production of liquid hydrocarbons from low value abundant resources such as lignite, peat, biomass, residues and waste. A general characteristic of such low value resources is that they typically have high moisture content, an oxygen content on a dry ash free basis in the range 20-60%, and an ash content ranging from a few percent to more than 50% by weight, which results in a low heating value as received.

Technologies for production nonconventional liquid hydrocarbons are known e.g. production of liquid hydrocarbons from coal has been known for more than 150 years. Pyrolysis or high temperature carbonization is another well known route for production of liquid hydrocarbons from solid fuel. Depending on the specific process the input stream may be heated to a temperature in the range 450 to 1000° C. in the absence of oxygen, driving of the volatile compounds and leaving a coke product. The hydrocarbon yields can be wide varying and ranges from 10 to 75% depending on the volatile content of the specific input streams and process conditions. In general fast heating (fast pyrolysis) and short residence time provides the highest yields. However, pyrolysis is limited to dry input streams e.g. moisture contents up to approximately 10% by weight. Further as only very limited conversion of the liquid hydrocarbon produced occurs during processing, the liquid hydrocarbons produced have a high oxygen and water content, and the liquid hydrocarbons produced consequently have a low heating value. Further, the liquid hydrocarbons are not mixable with petrodiesel and petrocrude, and are corrosive and susceptible to polymerization which makes long term storage difficult. This limits the direct use of such pyrolytic hydrocarbon liquids. Upgrading of pyrolytic hydrocarbons may be performed by hydrodeoxygenation or by addition of hydrogen during the pyrolysis process. However, though such hydrogenation processes are technically feasible, they will add significantly to the production costs as no oxygen is removed by the pyrolysis, and production of hydrogen is relatively expensive.

Indirect liquefaction of coal by first producing a syngas by thermal gasification and subsequent conversion into liquid hydrocarbons by the Fischer-Tropsch route has been practiced by Sasol in South Africa since the 1950's. Shell and ExxonMobil has developed similar technologies for production of liquid hydrocarbons from natural gas. Indirect gasification is characterized by being very capital intensive and having relatively low efficiencies. Typically the energy efficiency for conversion from coal to liquid hydrocarbons is in the range 30-50%.

Production of liquid hydrocarbons by dissolution of coal in a solvent in the presence of high hydrogen pressures and iron catalysts to produce high boiling liquids is known as the Bergius, Pott Broche or I. G. Farben process and was used to produce gasoline during the Second World War Common features are dissolution of a high proportion of coal in a solvent at elevated temperature, followed by hydro-cracking of the dissolved coal with hydrogen and a catalyst. The processes differ in the number of stages, process conditions and specific catalysts applied.

The production of liquid hydrocarbons from feedstock other than coal is also being conducted by the pyrolysis, indirect and direct liquefaction techniques described above. However, common for all of them is that they all require relatively dry input streams. A fundamental issue is difference in the stoichiometry of the input stream and liquid hydrocarbon fuels. For example dry wood may be represented by the formula $CH_{1.4}O_{0.7}$, whereas liquid hydrocarbon fuels may be represented by the formula $CH_2$:

$$CH_{1.4}O_{0.7} \rightarrow CH_2$$

This fundamentals result in an indispensable need for hydrogen addition and/or removal of carbon during the processing for adaption of the H/C ratio and removal of oxygen. Removal of carbon as char and $CO_2$ reduces the maximum obtainable yields of the desired hydrocarbons, whereas production of hydrogen is relatively expensive and adds significantly to the complexity and reduces the efficiency of such processes. Hence to be viable such processes require a very large scale and thereby become very capital intensive (UK DTI, Coal Liquefaction, Cleaner Coal Programme, Technology Status Report 010, October 1999).

Hence, there is a large interest in developing improved production techniques for liquid hydrocarbons not suffering from the drawbacks described above. Conversion of the feedstock in pressurized water at elevated temperatures is a route which has attracted significant attention over recent decades. Such techniques are generally called hydrothermal processing, and generally convert the feedstock into liquid hydrocarbon product, a char product, a water phase comprising water soluble organics, a gas and a mineral product.

An advantage of hydrothermal processing is that water is kept under pressure so that it is maintained in its liquid and/or supercritical state which means that no phase transition into steam occurs during processing. Hence, the energy loss, in the form of latent heat of evaporation, need not be supplied, and thus energy consuming processes such as evaporation or distillation are eliminated. This renders such processes very energy efficient particularly for wet input streams.

Water, in the vicinity of its critical point (374° C., 221 bar) obtains physical properties which are very different from water at ambient conditions e.g. the dissociation product of water is more than three orders of magnitude higher, it changes its polarity from a polar solvent to a non-polar solvent, interphase mass and heat transfer resistances are significantly reduced and mass- and heat transfer rates are therefore enhanced.

Due to these properties of water in the vicinity of its critical point, water may serve both as a reaction medium, a catalyst for acid and base catalyzed reactions and as a reactant and source of hydrogen in the conversion process.

Hence hydrothermal processing holds the potential to reduce the oxygen content of wet oxygenated feedstock with lower parasitic energy losses and with less hydrogen required due to formation of hydrogen in situ.

An excellent review of the state of the art of such hydrothermal processes and characteristic chemical reactions for conversion of organic macromolecules is given in A. Peterson et al, "Thermochemical biofuel production in hydrothermal media: A review of sub- and supercritical water technologies, Energy Environ. Sci., 2008, 1, 32-65.

Deoxygenation goes through dehydration, decarboxylation and hydrogenation reactions. However, the reaction pathways are complex and are to a large extent unknown except for simple molecules. Carbonaceous macromolecules may undergo various reactions including hydrolysis, dehydration, decarboxylation, steam reforming, water gas shift, steam cracking, Bouduard reaction, hydrogenation, methanation, Fischer-Tropsch, aldol condensation, esterification, methanol synthesis etc. The rate of the individual reactions and the extent to which conversion proceeds via specific reaction pathways depends on a number of factors.

Processes differ in the specific operating conditions and process design and layout being applied e.g. the feedstock, the dry solid content in the feed, the ash content of the feed, the operating pressure and temperature, the pH, the catalysts and other additives present in different parts of the process, the residence time in the different parts of the process, the heat integration, the separation techniques applied including further product handling and upgrading etc.

These factors all influence the distribution, yields and quality of the products produced i.e. the amount and quality of liquid hydrocarbons, the amount and quality of char, the amount of organics contained in the water phase, and the amount and quality of gas, and the amount and quality of mineral product. Further they influence the overall efficiency of the process i.e. the parasitic energy loss and overall energy recovery in desired product(s), amount of consumables used, the robustness and complexity the process as well as the overall process economics.

Several hydrothermal conversion processes of biomass and other carbonaceous macromolecules are in the development or demonstration including hydrothermal processes producing char or a solid residue as main product, thermal wet gasification, catalytic gasification and hydrothermal liquefaction to produce liquid hydrocarbons.

Processes for production of coke/char product by supercritical hydrothermal dewatering and/or partly depolymerization have been developed. Examples of hydrothermal processes being commercialized are the Slurycarb process by Enertech (N. L. Dickinson, WO95/014850, www.enertech.com), the K-fuel process by Evergreen Energy (R. F. Hogsett, EP2,287,279, www.evergreen.com), and the JGC Coal Fuel process by JGC Corporation (M. Tsurui et al, U.S. Pat. No. 6,132,478, www.jgc.co.jp/enindex.html). Common to these processes are is the aim to produce a partly depolymerized char product as the main product and that they operate at relatively low pressure (50-150 Bar) and temperature (200-300° C.).

Thermal wet gasification aims at producing gas by thermal decomposition without applying a heterogeneous catalyst. Typically such processes operate at temperatures in the range 500-700° C., and pressures above the critical pressure of water. Corrosion is severe at these conditions, and places very high demands on the materials of construction (A. Peterson et al, 2008). Hence, a considerable interest is directed to gasification processes applying a heterogeneous catalyst to decrease the temperature required for said gasification to proceed with reasonable rate and yield (A. Peterson et al, 2008; M. Osada et al, 2006; F. Vogel et al, US2009/0126274; D. C. Elliott et al, WO2009/099684). Catalytic gasification may proceed at operating temperatures in the range 400 to 500° C. However, the use of heterogeneous catalysts requires efficient removal of suspended particles prior to contact with said heterogeneous catalyst to avoid clogging of the reactor (A. Peterson et al, 2008; F. Vogel et al; US2009/0126274; D. C. Elliott et al, WO2009/099684). Progress is being made in this direction (F. Vogel et al; US2009/0126274; D. C. Elliott et al, WO2009/099684) No hydrothermal gasification plant has yet been commercialized (A. Peterson et al, 2008).

Hydrothermal processes for production of liquid hydrocarbons from carbonaceous materials are generally performed at a pressure sufficient to avoid vaporization of the fluid, and at lower temperatures than hydrothermal gasification processes, to maximize yield of liquid hydrocarbon products. Typically the pressure is in the range 40 to 200 bar and the temperature in the range 200 to 370° C. (A. Peterson, 2008). Some of the most significant prior processes are described below.

Shell developed the so-called HTU process for production hydrocarbon containing liquids from biomass (Annee et al, EP 0,204,354). The process converts biomass products such as wood at temperatures in the range 300 to 380° C. and a pressure above the boiling point of water, preferably in the range 150 to 250 bar and residence times from 3 to 10 minutes. No catalyst was used in the process. Heating was performed by a combination of indirect heating and heating by direct steam injection. An oil yield of 30-50% calculated as the ratio of the mass of oil to the mass of dry biomass feed was obtained from wood chips as well as char (carbon) in an amount of 10 to 22% by weight, 20-25% gas by weight and 20-23% water and water-solubles by weight. The oil produced contained up to 20% oxygen by weight. An embodiment comprises recycling a substantially aqueous liquid to a pretreatment step to increase the thermal efficiency and reduce water consumption.

A further development of the above HTU process is disclosed by Van de Beld et al in U.S. Pat. No. 7,262,331. The further development include pressurizing the feedstock to preferably 130 to 180 bar, heating to a temperature in the range 180-280° C. and maintaining it at these conditions in a period up to 60 minutes to produce a reaction mixture, which is further heated to a temperature in the range 280 to 350° C. over a period of up 60 minutes. An option includes separation of a liquid fraction containing fermentable compounds from the mixture prior to heating to the reaction temperature. Heating is performed by a combination of indirect heating, direct injection of steam, direct injection of a preheated $CO_2$ containing gas and/or an oxygen containing gas. The process results in a liquid hydrocarbon crude with an oxygen content of 10-25% by weight, a mineral fraction 0.5-10% by weight, and with about 50% of the liquid hydrocarbons boiling above 450° C. The heavy fraction has an oxygen content of 10-20% by weight and mineral content of 0.5 to 25% by weight, and the light fraction has an oxygen content of 5 to 25% and a mineral content of less than 0.5% by weight.

Yokoyama et al (U.S. Pat. No. 4,935,567) discloses a process for producing a liquid hydrocarbon product from cellulotic biomass such as wood by treatment of the biomass by conversion of the biomass at a pressure of 3 to 100 atm and a temperature from 250° C. to 400° C. (372 to 378° C. preferred) in the presence of a neutral oxygen-containing organic liquid in the form of alcohols, ketones, ethers, esters and mixtures thereof. A particularly preferred embodiment is when said neutral oxygen-containing organic liquid is acetone. The oxygen containing liquid is claimed to accelerate the reactions and makes it easy to separate the liquefied product from the reaction mixture. Another embodiment include the use of an alkaline catalyst in a concentration of 1 to 10% by weight of the dry biomass. The alkaline catalyst may be used in an amount so that the reaction mixture has a pH in the range 10-14 and preferably in the range. The dry solid content of the biomass is preferably in the range 5 to 20% by weight (5-20 parts). The product was separated by decanting (oil phase heavier than water), and subsequent distillation to distill off water. The liquefied hydrogen products produced had calorific values between 24.5 MJ/Kg and 35.5 MJ/kg and contained 14-31% oxygen by weight. Most of the oils solidified at room temperature and were not considered to be stable at room temperature. An experiment conducted at 375° C. produced oil that didn't solidify at room temperature. Though the patent discloses some parts which may be attractive, the yields achieved are considered as very low i.e. 20-25% of the dry biomass weight. The oxygen content of the produced liquid hydrocarbon product is considered to be high despite the relatively high calorific values. Further be noticed that the pressure being applied is not high enough to ensure that the fluid mixture is in a single phase. Assuming that the fluid mixture comprises pure water, the fluid will be on a vapor phase in the whole temperature range from 200 to 400° C., and at 100 atm the fluid will be on a liquid form up to 312° C., and on a vapor form from 312 to 400° C. This is considered insufficient according to the present invention.

Humfreys (WO2009/015409) discloses a process for converting organic matter such as lignite or brown coal, lignin, cellulose, hemicellulose, organic waste, plastic or a generic polymer into products including mixing it with a supercritical liquid comprising one or more of the group consisting of water, methanol, and ethanol at a pressure greater than 220 bar (up to more than 300 bar) and temperatures in the range 350 to 420° C. The products produced by the process include heavy oil petroleum fractions referred to as oil, asphaltenes and pre-asphaltenes, and also yielding residual char, gas (mostly carbon dioxide) and produced water as the main products. The process disclosed is in many ways very similar to the HTU process described above in relation to the disclosures by Annee et al and Van de Beld et al with major differences being the presence of methanol and/or ethanol in the fluid and/or operation at higher pressures and/or temperatures.

Iversen et al (WO2006/1170002A3) discloses a catalytic process, wherein organic material is converted into converted into hydrocarbon fuels with high efficiency. In this process, organic matter such as biomass, waste and sludges is converted by pressurizing said organic matter to a pressure of at least 225 bar, and heating said fluid comprising said organic matter to a temperature of at least 200° C. in the presence of a homogeneous catalyst (comprising at least one compound of an element of group IA of the periodic table of elements, such as at least one compound of potassium and/or sodium), and subsequently contacting the fluid containing organic material with a heterogeneous catalyst (comprising a compound of at least one element of group IVB of the periodic table such as zirconia and/or titania and/or alpha alumina at a temperature of up to 374° C., while maintaining the fluid at a pH of least 7. In a preferred embodiment described, the heating is performed in a sequential manner, and the hot effluent from the heterogeneous reactor, containing reaction products and/or intermediate reaction products, is at least partly recycled and mixed with the feed mixture after heating to more than 200° C. The combined fluid of the incoming feed mixture and re-circulated reactor effluent is further heated to reactor temperature in a trim-heater. Accompanying examples indicate up to 40% of the carbon and up to 76% of the energy contained in the feed being recovered as a liquid hydrocarbon (oil).

Despite that hydrothermal technologies have many potential benefits over conventional methods of processing biomass and other organic macromolecules to useful fuels and chemicals, the fact remains that these technologies have yet not been being widely commercialized (A. Peterson et al, 2008).

There are a number of challenges that may be addressed to improve the effectiveness of processing. These include:

Gasification processes operating without a heterogeneous catalyst at temperatures in the in the range 450-700° C., demand specialized materials to withstand the high temperature and corrosive environment at these conditions (e.g. A. Peterson et al, 2008).

Effective and economically viable processes demand a feedstock at high dry solid loading e.g. at least 20% by weight. Size reducing and feeding of such feedstock is difficult as it may have a solid appearance and high viscosity, particularly for fibrous materials, and may block orifices and contra valves in pumps. Inadequate pretreatment and/or homogenization and/or pump design has limited a number of processes to operate at low dry solids content, which challenges the economy of such processes (e.g. A. Peterson et al, 2008; M. Osada et al, 2006).

Some feedstock contains high amount of salts and inorganics that can lead to precipitation, fouling and plugging of pipes, heat transfer surfaces, reactors and other process equipment if not properly managed (e.g. A. Peterson et al, 2008; Osada, et al, 2006).

Processes applying heterogeneous catalysts for production of syngas or syncrudes are applied in a number of processes to lower the operating temperature and/or increase the yield of desired product. The success of these processes has been varying. A number of processes have been developed wherein inadequate catalysts which do not withstand hydrothermal processing conditions have been applied. Further the application of such heterogeneous catalysts are prone to clogging of reactors and catalysts pores if not properly designed for high loads of impurities and/or efficient removal of suspended particles prior to said catalytic reactors is performed (A. Peterson et al, 2008, Vogel et al, US2009/0126274A1, Elliott et al, WO2009/099684A3).

Processes are susceptible to formation of tar and chars if process steps and operating conditions are not selected properly. The formation of tars and char may result in increased fouling and result in a less efficient process due to formation of solid residues instead of desired products (Vogel et al, US US2009/0126274A1).

Some feedstocks such as lignite, sub-bituminous coals and high-lignin containing biomasses are susceptible to tar and char formation, and often produce significant amount of solid residues.

Water soluble organic compounds in prior art hydrothermal processes for liquid hydrocarbon production can comprise 5 to 70% of the carbon and 10 to 60% of the energy contained in said carbonaceous material being fed to the process, depending of the specific carbonaceous material and/or combination of carbonaceous materials being converted, specific process steps and process parameters for said hydrothermal conversion process (e.g. Hammerschmidt et al, 2011). Besides representing a process loss reducing the yield of desired products, such water soluble organic products may be considered as pollutants that increases the treatment and purification requirements of the water effluent.

Homogeneous catalysts such as potassium and sodium are well known to enhance the degradation and conversion of organic macromolecules in the feed mixture and suppress formation of coke and char for both gasification and liquefaction process (A. Peterson, 2008; S. Karagoz et al, 2006; T. Bhaskar et al, 2006; Hammerschimidt, 2011). However, such homogeneous catalysts are relatively expensive, and must be recovered or reused in order to achieve an economically viable process (A. Peterson et al; 2008).

Hence an improved process and apparatus for production of liquid hydrocarbons as the main product and not suffering from the problems and disadvantages from the prior art is advantageous and desirable.

Accordingly, it is an object of the invention to provide an improved process for the production of liquid hydrocarbon, and further to provide an improved apparatus for the production of liquid hydrocarbon.

SUMMARY OF THE INVENTION

According to the invention the objective of the invention has been achieved by means of a continuous process for converting carbonaceous material contained in one or more feedstocks into a liquid hydrocarbon product, said feedstocks including the carbonaceous material being in a feed mixture including one or more fluids, said fluids including water and further liquid organic compounds at least partly produced by the process in a concentration of at least 1% by weight, the process comprising:
  converting at least part of the carbonaceous material by:
    pressurising the feed mixture to a pressure in the range 50-400 bar
    heating the feed mixture to a temperature in the range 250-500° C., and
    maintaining said pressurized and heated feed mixture in the desired pressure and temperature ranges in a reaction zone for a predefined time;
    cooling the feed mixture to a temperature in the range 25-200° C. and
    expanding the feed mixture to a pressure in the range of 1-70 bar, thereby causing the carbonaceous material to be converted to a liquid hydrocarbon product;
    separating a fraction comprising liquid hydrocarbon product, and leaving a residual fraction;
      feeding said residual fraction into a bioreactor for the production of biomass such as algae and/or bacteria such as cyano bacteria.

By performing the process with the parameters specified a more effective process has been achieved and hence a more competitive hydrocarbon product may be achieved.

Preferably said algae and/or bacteria in said recovery step are concentrated and recycled to the feed mixture.

Advantageously at least partly expanding said converted feed mixture in a flash separation step, wherein the converted feed mixture is separated into a gas phase and a liquid phase, and wherein liquid $CO_2$ is recovered from said gas phase, and where at least part of the liquid $CO_2$ recovered is fed into the bioreactor as a carbon source for enhancing growth.

Preferably the concentration of said at least one liquid organic compound contained in the feed mixture is at least 5% by weight, preferably at least 10% by weight, more preferred at least 20% by weight.

Said at least one organic compound being added in a concentration of at least 1% by weight may comprise a range of different compounds including alcohols and polyalcohols, ketones, carboxylic acids, amino acids, aldehydes, ethers, esters, amines, amides, pyroles, indoles, catecols, phenols, piperidone, cyclopentanones, cyclopentenones, toluene, phenolic acids such as ferulic acid, benzoic acid, flavonoids such as flavones, flavenols, coumaric acid and/or cinnamic acid, hydroxycinnamic acid derivates, lignin monomers (monolignols) such as p-coumaryl alcohol, coniferyl alcohol and/or sinapyl alcohol and other phenol derivatives such as polyphenols, monomeric and oligomeric alkylated phenols, cresol, catecols, thymol alkoxy phenols, alkylated cyclohexanes, alkylated cyclopentanes, toluene, mono- and polynuclear aromatic compounds such as substituted aromatics, quinone and benzon quinones, anthrax quinone, phenanthrene quinone, acenaphephthene quinone, chrysene quinone, diphenoquinone, stilbene quinone, naphodiqiuinones, tetraline, naphthenes, preasphaltenes, asphaltenes, polyaromatics, fatty acids, lipids, fat, waxes, paraffins, alkanes, alkenes and combinations thereof.

A carbonaceous material, in the present context, means a carbon-containing material. Said carbonaceous material should be interpreted in broad terms and may be contained in one or more feedstock such as ancient biomass (for example: lignite and peat), lignin, cellulotic materials such as biomass and wastes including plastics (man made polymers). The carbonaceous may be in a solid form, have a substantially solid appearance, or be suspended, dissolved and/or slurried in a fluid such as sludge or even be in a liquid form. Carbonaceous materials according to the present invention are further exemplified in the further description and accompanying examples and claims.

Liquid hydrocarbon product, in the present context, means a fuel such as an oil or oil-like substance, fuel additives, and other commercially useful hydrocarbon products and chemicals. The liquid hydrocarbon product may be a crude that may be further upgraded and/or refined. The liquid hydrocarbon product may contain oxygen and/or water and/or ash.

The effect of the presence of said one or more liquid organic compounds at the pressure and temperatures during the second step of conversion are believed to be multifunctional. They may work as a stabilizer and/or dispersant assisting in homogenizing the feed mixture such as lowering the viscosity and/or decreasing sedimentation and/or precipitation during said conversion process. They may further act as a solvent assisting in dissolving and/or extracting said carbonaceous material thereby lowering the viscosity of said feed mixture and/or enhancing the conversion towards desired products. Furthermore they may act as radical scavengers suppressing polymerization reactions such as tar and char formation and/or as hydrogen donors during said conversion process thereby increasing the yield and quality of the desired liquid hydrocarbon products. In addition to this, said one or more organic liquid compounds may function as reactants that may be consumed and/or involved in said conversion process.

In a preferred embodiment the weight ratio of the concentration of said one or more liquid organic compounds to the weight of dry solid carbonaceous material in said feed mixture is at least 0.01 such as a weight ratio of at least 0.025, and preferably said weight ratio is at least 0.05 such as at least 0.1 or at least 0.2, and preferably the ratio of the weight of said at least one organic compounds to the weight of dry solid carbonaceous material in said feed mixture is in the range 0.05 to 2, such as in the range 0.1 to 0.15 or in the range 0.10 to 1.0 and even more preferably the ratio of the weight of said one or more organic compounds to the weight of dry solid carbonaceous material in said feed mixture is in the range 0.15 to 0.75 such as in the range 0.2 to 0.5.

Preferably the feed mixture provided contains at least one homogeneous catalyst in the form of a compound of potassium and/or sodium so as to ensure a total concentration of potassium and sodium of at least 0.5% by weight, preferably 1-10% by weight, more preferably in the range 2-5% by weight. Said at least one homogeneous catalyst in the form of potassium and/or sodium, and the pre-treating may include controlling the concentration of said at least one homogeneous catalyst by measuring the content and adjusting the concentration by adding potassium and/or sodium in the form of a salt or solution. Suitable forms of potassium and sodium include potassium hydroxide, sodium hydroxide, potassium carbonate, sodium carbonate, potassium bicarbonate and sodium bicarbonate. Further in many applications according to the present invention said at least one homogeneous catalyst may be least partly contained in said one or more feedstock, and said controlling of the concentration of said at least one homogeneous catalyst may involve mixing a feedstock having a high concentration of potassium and sodium with a feedstock having a low concentration of said homogeneous catalyst in the form of potassium and/or sodium.

The concentration of said at least one homogeneous catalyst is according to the present invention at least 0.5% by weight, and preferably the concentration of said at least one homogeneous catalyst is at least 1% by weight and even more preferably the concentration of said at least one homogeneous catalyst in the form of potassium and/or sodium is in the range 1 to 10% by weight such as in the range 1 to 5% by weight and most preferably in the range 1 to 3% by weight such as in the range 1.5 to 2.5% by weight.

Preferably the ratio of weight of said one or more liquid organic compounds to the dry weight of carbonaceous material in said feed mixture is in the range 0.1 to 2.0, preferably in the range 0.15 to 1.0, more preferably in the range 0.2-0.5.

Preferably the pressure during said conversion step is in the range 275 to 350 bar, preferably 290 to 330 bar, more preferably in the range 300 to 325 bar. Preferably the temperature during said conversion step is in the range 380 to 430° C., preferably 385 to 430° C., more preferred in the range 390 to 430° C. such as in the range 400 to 430° C. The combination of operating pressure and temperature, the presence of one or more liquid organic compounds and optionally at least one homogeneous catalyst in the form of potassium and/or sodium according to preferred embodiments of the first aspect of present invention results in a number of advantages related processing of a broad range of carbonaceous material including difficult materials such as feedstock having a high content aromatics such lignite, sub-bituminous coal, peat and lignin.

Preferably the feed mixture at entry temperature is pressurized essentially to the desired process pressure before heating to process temperature is initiated.

Preferably the pH during said conversion is above 7, preferably in the range 8 to 12, and more preferably 8-10, where the pH of the feed mixture is measured during and/or after the conversion and when the pH measurement is outside the preferred range, the composition of the feed mixture is altered to correct the pH in the conversion.

Preferably the heating of the feed mixture is taking place at a rate of at least 50° C./min, preferably 75° C./min, more preferred 100° C./min and even more preferred 150° C./min in the temperature range 140-300° C.

Preferably the residence time in said reactor is in the range 10 to 40 minutes, preferably in the range 10 to 30 minutes, more preferably in the range 10 to 25 minutes.

Preferably the average flow velocity in pipes in the process and/or at the entry of the conversion zone/reactor, is at least 0.2 m/s, preferably in the range 0.2-5 m/s, more preferred 0.5-3 m/s.

Preferably the process comprises recovery of substances from the residual fraction remaining after separation of said fraction comprising a liquid hydrocarbon product, and wherein said recovery is performed in one or more evaporators and condensers, and wherein the first of said evaporators is adapted to perform a vapour recompression technique, including mechanical vapour recompression and/or thermal recompression.

Preferably said evaporators are heated by steam and said steam is at least partly produced by the process.

Preferably at least the first evaporator comprises at least two condensers operating decreasing condensation temperatures.

Preferably the condensation temperature of first condenser is in the range 85-110° C., preferably in the range 90-105° C. and wherein the temperature of the last condenser is preselected so as to condense compounds having a boiling point lower than water, such as a condensation temperature in the range 20-80° C., preferably a condensation temperature in the range 30 to 70° C., such as a condensation temperature of the last condenser in the range 40-60° C.

Preferably said substances being recovered comprise water soluble organics and/or homogeneous catalyst in the form of potassium and/or sodium, and said recovered substances are at least partly recirculated in a concentrated form and introduced into said feed mixture.

Preferably the concentration factor, as defined as the mass ratio of the residual fraction fed to said recovery step to the mass of concentrate, is at least 4, preferably the mass ratio of the residual fraction fed to said recovery step to the mass of concentrate is at least 5, more preferably the mass ratio of the residual fraction fed to said recovery step to the mass of concentrate is at least 7.

Preferably said algae and/or bacteria in said recovery step are concentrated and recycled to the feed mixture.

Preferably the heating for the conversion is at least partly performed by introducing one or more supercritical fluids, such as a superheated supercritical fluid, into said feed mixture.

Preferably the heating performed for the conversion is at least partly performed by introducing an oxidizing agent into said feed feed mixture.

Preferably the introduction of said one or more supercritical fluids and/or oxidizing agent is performed in a vertically positioned cyclone shaped mixing chamber, and wherein the feed mixture is introduced in the center from top with a ratio of the average linear velocity in the inlet pipe to the minimum average linear velocity of the mixed fluids in said mixing chamber of at least 2, and wherein the superheated supercritical fluid and/or oxidizing agent is introduced into said chamber substantially tangentially to said mixing chamber at a velocity ratio of at least 4, and wherein the partially or fully converted feed mixture is withdrawn from said cyclone shaped mixing chamber from the bottom.

Preferably the introduction of said one or more supercritical fluids and/or oxidizing agent is performed in a mixing chamber having a conically shaped inlet and a conically shaped outlet, the walls of conical shaped inlet and outlet having angle to the centreline of said mixing chamber of maximum 60°, and wherein the feed mixture is introduced from the top with a ratio of the average linear velocity in the inlet pipe to the minimum average linear velocity of the mixed fluids in said mixing chamber of at least 2, and wherein the superheated supercritical fluid and/or oxidizing agent is introduced into said mixing chamber with an angle, a, in the flow direction of at least 20°, and wherein the average linear velocity ratio of said superheated supercritical fluid and/or oxidizing agent is at least 4, and wherein the partially or fully converted feed mixture is withdrawn from said mixing chamber from the bottom.

Preferably the process comprises upgrading, wherein the liquid hydrocarbon product from said separation is heated to a temperature in the range 350 to 600° C., at a pressure in the range 0.5 to 30 bar, thereby producing at least one liquid hydrocarbon fraction and/or at least one solid residue fraction and/or at least one gas fraction and/or at least one aqueous fraction.

Preferably at least part of the aqueous fraction is recycled to the recovery step and mixed with the residual fraction from said separation.

Preferably said upgrading by heating is performed in at least 2 steps.

Preferably the temperature in said first heating step of heating is maintained below 200° C., preferably below 180° C., more preferably below 160° C., more preferably below 140° C. and even more preferably in the range 100 to 140° C.

Preferably the heat for said first evaporation step is recovered from said cooling and expanding the converted feed mixture.

Preferably a residual fraction comprising liquid hydrocarbons and/or solids is withdrawn from said first heating step and fed to a second heating step, wherein it is heated to a temperature of up to 600° C., preferably in the range 400 to 550° C. and more preferably in the range 425-500° C.

Preferably the pressure is maintained in the range 2.5 to 10 bar. Preferably at least a fraction of said heated residual fraction comprising liquid hydrocarbons is fed to a fractionator.

Preferably the evaporated fraction is condensed and fractionated in two or more condensing steps having predefined and decreasing condensation temperatures.

Preferably the outlet temperature of the non-condensed liquid hydrocarbons in said first condensation step is in the range 340 to 400° C., preferably in the range 350-390° C., more preferably in the range 360 to 380° C.

Preferably the outlet temperature from the second condensation step is in the range 120 to 300° C., preferably in the range 150 to 250° C.

Preferably a fraction not being condensed in said one or more condensing steps comprises a combustible gas and wherein said gas is combusted to produce heat for heating in the process.

Preferably a cooling medium is used in said condensation, and the heat transferred to said cooling medium is used for at least partly supplying the heat required in the conversion.

Preferably the second heating step comprises two or more vessels or drums operating in a sequential cycle, and wherein the solid residue is allowed to accumulate within said vessels or drums for a predefined period.

Preferably at least partly expanding said converted feed mixture in a flash separation step, wherein the converted feed mixture is separated into a gas phase and a liquid phase, and wherein liquid $CO_2$ is recovered from said gas phase.

Preferably the process comprises recovery of liquid $CO_2$ includes an expansion to a pressure in the range 50 to 70 bar and a first step of cooling of the gas phase to a temperature in the range 35 to 80° C., and second step of cooling the gas phase to a temperature in the range 12 to 30° C.

Preferably the expanding and cooling comprises first cooling said converted feed mixture at process pressure to a temperature in the range 100-200° C. by heat exchange with the incoming feed mixture and subsequently expanding said cooled product stream in one or more steps at least one of said expansion steps comprising an expansion in a flash separator to a pressure in the range 50 to 70 bar, thereby producing a gas phase and a liquid phase, and subsequently cooling the gas phase in a first condenser to a temperature in the range 35 to 80° C., and cooling the gas phase from said first condenser to a temperature in the range 12-30° C., thereby producing a condensate comprising liquid $CO_2$.

Advantageously a pre-treatment is provided prior to the main process for providing a feedstock for the process where the pretreatment comprising:
  adding at least one feedstock material with a maximum particle size of 30 mm, and
  adding a liquid organic compound in an amount of at least 1% by weight.

Preferably the feedstock material added has a maximum particle size of 15 mm, preferably of 5 mm, more preferred of 1 mm, and even more preferred of 0.5 mm.

Preferably the pretreatment further comprises a division of the particles in the feedstock, to obtain the desired maximum particle size.

Preferably a liquid organic compound is added in an amount of at least 5% by weight, preferably at least 10% by weight, more preferred at least 20% by weight.

Preferably at least one homogeneous catalyst is added in the form of a compound of potassium and/or sodium so as to ensure a total concentration of potassium and/or sodium of at least 0.5% by weight, preferably 1-10% by weight, more preferably in the range 2-5% by weight.

Preferably the pre-treating further comprises chemical pulping.

Preferably the pretreatment further comprises heating of the feed mixture to a temperature of 50-200° C., preferably 90-160° C., at a pressure of 1-20 bar, preferably 4-20 bar to avoid boiling.

Preferably the pretreatment has a duration of 5 minutes to 24 hours, preferably 10 minutes to 12 hours, more preferred 15 minutes to 6 hours and even more preferred 20 minutes to 3 hours.

Preferably the dry solid content of the carbonaceous material is at least 20% by weight such at least 25% by weight, and preferably the dry solid content of the carbonaceous material is at least 30% by weight such as at least 40% by weight.

Preferably the dry solid content of the carbonaceous material is in the range 20 to 70% by weight and preferably in the range 30 to 60% by weight.

The objective of the invention is further achieved by an apparatus for continuous conversion of carbonaceous material contained in one or more feedstocks into a liquid hydrocarbon product, said carbonaceous material being in a feed mixture including said carbonaceous material and one or more fluids, said fluids including water, the apparatus comprising:

at least one feed pump for feeding the feed mixture into the processing zone;

a pressurization device adapted to pressurize the feed mixture to a pressure of 50-400 bar a heating device adapted to heat the pressurized feed mixture to a temperature of 250-500° C.

a conversion device adapted to hold the pressurized and heated feed mixture for a conversion time of 10-40 minutes a cooling device adapted to cool the treated feed mixture to a temperature of 25-200° C.

an expansion device adapted to reduce the pressure of the treated feed mixture to a pressure of 1-70 bar, and a separation device adapted to separate a liquid hydrocarbon product from the treated and successively cooled and expanded feed mixture, and leaving an aqueous fraction;

a bioreactor for treating the aqueous fraction, and generating an algae and/or cyanobacteria growth Preferably a pretreatment apparatus is provided prior to the feed pump. Preferably the pretreatment apparatus comprises a device adapted to divide particles in the feedstock and to mix the feedstock and the water and the liquid organic compound to a feed mixture with the specified feed mixture properties for the process.

Preferably said conversion device comprises a vertically oriented reactor having a conically shaped inlet for introducing said feed mixture in the top and a conically shaped outlet in the bottom, and wherein the angle of the walls of said conical inlet to the centreline of said reactor is below 60°, and wherein the angle of the walls of said conical outlet to the centreline of said reactor is below 30°.

Preferably a vertically positioned cyclone shaped mixing chamber is provided for the introduction of said one or more supercritical fluids and/or oxidizing agent is performed in, and wherein an inlet tangential to the mixing chamber is provided for introducing the superheated supercritical fluid and/or oxidizing agent into said chamber and a bottom outlet is provided for withdrawing the fully converted feed mixture from said cyclone shaped mixing chamber.

Preferably a mixing chamber having a conically shaped inlet and a conically shaped outlet is provided for the introduction of said one or more supercritical fluids and/or oxidizing agent, the walls of conical shaped inlet and outlet having angle to the centreline of said mixing chamber of maximum 60°, and wherein an inlet is provided with an angle, a, in the flow direction of at least 20° for the introduction of the superheated supercritical fluid and/or oxidizing agent into said mixing chamber, and wherein an outlet is provided at the bottom for withdrawing the partially or fully converted feed mixture from said mixing chamber.

Preferably said conversion reactor is adapted to be vertically oriented and further having a conically shaped inlet for introducing said feed mixture in the top and a conically shaped outlet in the bottom, and wherein the angle of the walls of said conical inlet to the centreline of said reactor is below 60°, and wherein the angle of the walls of said conical outlet to the centreline of said reactor is below 30°.

Preferably a cyclone shaped mixing chamber adapted to be vertically positioned, is provided for the introduction of said one or more supercritical fluids and/or oxidizing agent is performed in, and wherein an inlet tangential to the mixing chamber is provided for introducing the superheated supercritical fluid and/or oxidizing agent into said mixing chamber and a bottom outlet is provided for withdrawing the fully converted feed mixture from said cyclone shaped mixing chamber.

Preferably a mixing chamber having a conically shaped inlet is provided for the introduction of said one or more supercritical fluids and/or oxidizing agent, and a conically shaped outlet, the walls of conical shaped inlet and outlet having angle to the centreline of said mixing chamber of maximum 60°, and wherein an inlet is provided with an angle, a, in the flow direction of at least 20° for the introduction of the superheated supercritical fluid and/or oxidizing agent into said mixing chamber, and wherein an outlet is provided at the bottom for withdrawing the partially or fully converted feed mixture from said mixing chamber.

Another aspect of the invention is to provide a feed mixture for the conversion process, the feed mixture comprising a feedstock with a particle size of maximum 30 mm, water and at least one liquid organic compound, where concentration of said at least one liquid organic compound contained in the feed mixture is at least 1% by weight, preferably at least 5% by weight, more preferred at least 10% by weight and even more preferred at least 20% by weight.

Preferably the feed mixture provided contains at least one homogeneous catalyst in the form of a compound of potassium and/or sodium so as to ensure a total concentration of potassium and sodium of at least 0.5% by weight, preferably 1-10% by weight, more preferably in the range 2-5% by weight.

Preferably the ratio of weight of said one or more liquid organic compounds to the dry weight of carbonaceous material in said feed mixture is in the range 0.1 to 2.0.

Preferably the feed mixture comprising a dry solid content of carbonaceous material is in the range 20-70% by weight, preferably 30-60% by weight.

Preferably the feed mixture comprising particles with a maximum diameter of 30 mm, advantageously with a maximum diameter of 15 mm, preferably of 5 mm, more preferred of 1 mm, and even more preferred of 0.5 mm In another preferred embodiment according to the present invention said at least one liquid organic compound comprises, or further comprises, water-soluble organics produced in said process and recovered from said residual fraction.

In a further embodiment said one or more homogeneous catalyst is at least partly recovered and recycled to said pretreatment step as further disclosed in the detailed description of the invention and accompanying figures and examples below.

A particularly preferred embodiment include at least partly recovering both said one or more homogeneous catalyst(s) and said one or more liquid organic compound(s) from said residual fraction in the same fraction, and recycling the recovered one or more homogeneous catalyst(s) and said one or more liquid organic compounds to said first step of pre-treating.

The optional presence of at least one homogeneous catalyst in the form of potassium and/or sodium further suppresses tar and char formation reactions, and enhancing the conversion of the carbonaceous material towards desired products.

Hence, a process according to a first aspect of the invention results in less formation of tar and chars, and improves the yields and quality of desired liquid hydrocarbon products. This further results in a process which are more effective, economical and robust than prior art processes. Hence, several of the objectives of the invention are fulfilled.

The apparatus may preferably further comprise means for adding to said feed mixture at least one liquid hydrocarbon compound such as by re-circulating and introducing liquid hydrocarbons produced or a fraction of said liquid hydrocarbon produced to said pre-treatment stage.

Furthermore the apparatus may preferably further comprise recovery means for recovering liquid compounds water soluble organics and/or homogenous catalyst from the residual fraction, and re-circulating these in a concentrate form to said pre-treatment stage.

In addition hereto the apparatus may further comprise means for upgrading said liquid hydrocarbon fraction such as means for heating and/or fractionating said liquid hydrocarbon fraction.

The first and second aspect of the present invention may each be combined with any of the other aspects. These and other aspects of the invention will be apparent from and elucidated with reference to the embodiments described hereinafter.

The combination of liquid organics and homogeneous catalysts, high pressure and temperature and pH results in a mechanism, which is believed to be a combination of dissolution of the carbonaceous material and depolymerisation/decomposition of the carbonaceous material.

Through the present invention as defined in the main claims alone or in combination with one or more dependent claims a process for production of liquid hydrocarbons from carbonaceous materials has been provided that is more economical and/or effective than the prior art, e.g. produces more liquid hydrocarbons and/or recovering more energy from said feedstock in said liquid hydrocarbons and/or using less energy and/or using less consumables such as hydrogen and other chemical additives in the process.

Further a process for production of liquid hydrocarbons which is more reliable, robust and less prone to fouling and clogging by tar, char, dissolved and/or suspended salts and/or inorganic materials than the prior art may be obtained. A process for production of liquid hydrocarbons which is more environmentally sustainable than the prior art e.g. produces less pollutants and waste streams and/or having a smaller $CO_2$ footprint, may likewise be achieved.

A process for producing liquid hydrocarbon products that has a higher quality than obtained by the prior art may be achieved. Higher quality may mean having a higher H/C ratio and/or a lower O/C ratio and/or a higher heating value and/or a lower viscosity and/or a lower acid number and/or a lower Conradson carbon residue number and/or a lower water content and/or lower ash content and/or a lower alkali metal content and/or a lower density and/or having an improved storage stability and/or having an improved mixability with petrocrude oil and/or having an improved mixability with heavy fuel oil and/or having and improved mixability with gas oil and/or diesel and/or having an improved mixability with gasoline and/or having an improved mixability with jet fuel.

In addition a process that is simpler and less capital intensive than the prior art may be achieved.

Further a process that allows processing of feedstock at higher dry matter contents and/or a wider range of feedstocks than in the prior art may be achieved, and further to provide a liquid hydrocarbon product derived from solid feedstocks that has relatively improved properties.

Further embodiments and advantageous effects of the present invention are presented in the following description of preferred embodiments of the invention.

Throughout this document the terms "comprising" or "comprises" do not exclude other possible elements or steps. Also, the mentioning of references such as "a" or "an" etc. should not be construed as excluding a plurality.

DESCRIPTION OF PREFERRED EMBODIMENTS OF THE INVENTION

The method and apparatus according to the invention will now be described in more detail with regard to the accompanying figures. The figures show one way of implementing the present invention and is not to be construed as being limiting to other possible embodiments falling within the scope of the attached claim set.

Figure 1:
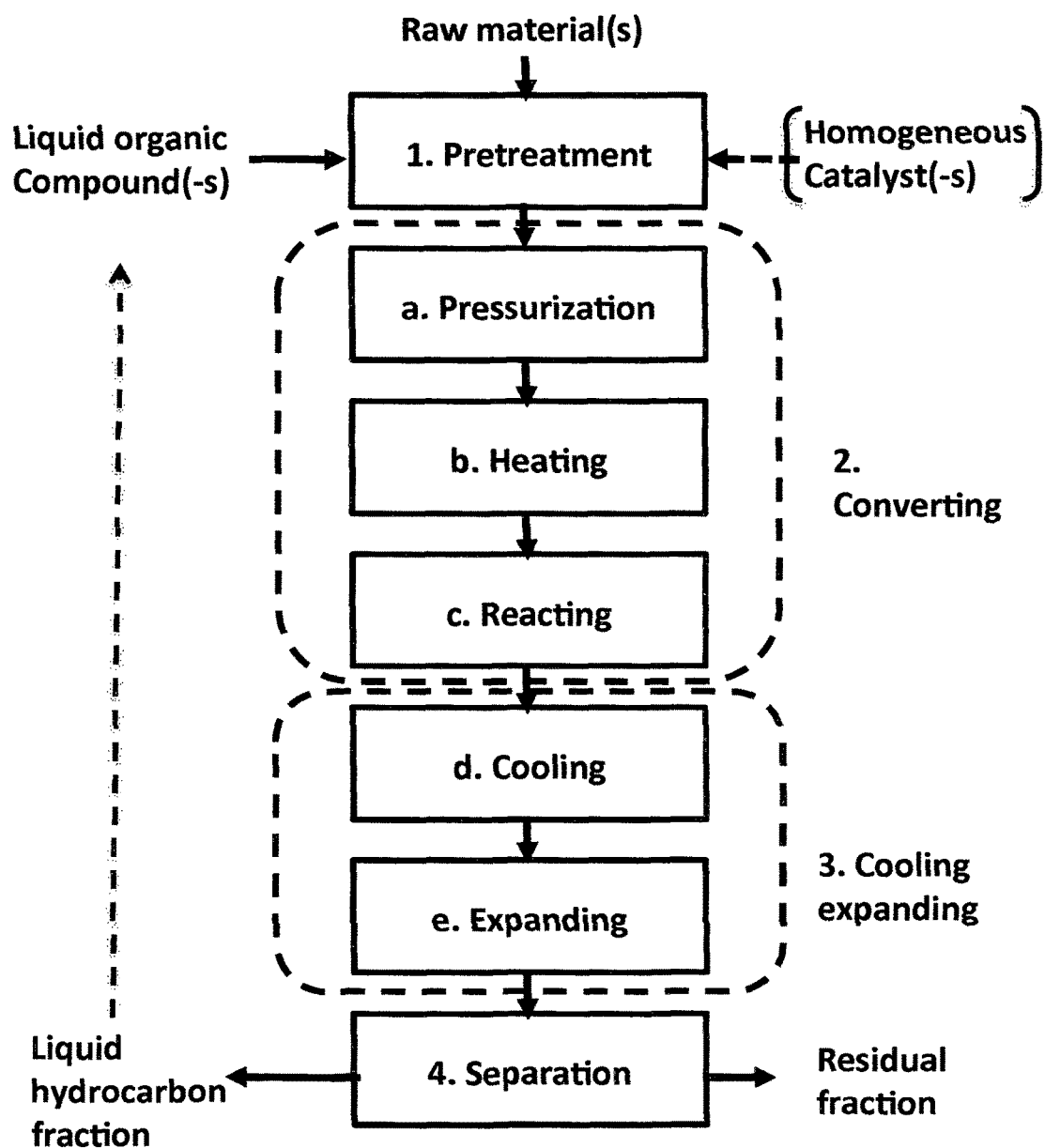
FIG. 1 shows schematically a flow diagram of a conversion process according to the present invention.

FIG. 1 shows a simplified flow diagram of a continuous hydrothermal process for conversion of carbonaceous material to liquid hydrocarbons according to an embodiment of the present invention.

The carbonaceous material to be converted in a process according to the present invention may be contained in one or more feedstock. The feedstock may be on a solid form or may have a solid appearance, but may also be in the form of sludge or a liquid. The dry solid content of the feed mixture according to many embodiments of the present invention at least 20% by weight such as at least 25% by weight, and preferably the dry solid content of said carbonaceous material is at least 30% by weight such as at least 40% by weight.

Non-limiting examples suitable feedstock that may be converted by a process according to the present invention include ancient biomass such as low rank coals such as lignite, sub bituminous coals, peat, moss, spaghnum; biomass such as wood, wood chips, sawdust, forestry thinnings and waste, bark, leaves, lignin, cellulose, hemicellulose, sugars, protein, wine trash and agricultural residues and byproducts such as grasses, straw, stems, stover, husk, cobs, shells from e.g. wheat, rye, corn, rice, sunflowers; empty fruit bunches from palm oil production, palm oil manufacturers effluent (POME, bagasse), manure fibres from livestock production, greenhouse waste, garden waste and weeds; energy crops like jatropha, sorghum, switchgrass and miscanthus; aquatic biomass such as macroalgae, microalgae, bacteria such as cyanobacteria; waste, residues and byproducts from industry such as residues from olive production, residues and byproducts from juice production, residue from wine production, residues, byproducts and waste streams from vegetable oil production; Residues, byproducts and waste from food production such as brewers spent grains and yeast; residues and byproducts from fruit and vegetable processing such as pulp; residues and byproducts from fermentation processes such as wet distillers grain, vinasse, molasses, black liquor from paper production, aerobic and anaerobic digested sludges e.g. sewage sludge from wastewater cleaning and/or digested sludge from biogasification, leachate, clarifier sludge, paper waste, green fraction of household waste, restaurant waste, slaughter house waste, risk material from meat and bone processing, municipal solid waste, used and recycle oils, fat, organic solvents, glycerine, refinery wastes, plastic and polymers and combinations thereof.

The carbonaceous material in said one or more feed stock is added to a pretreatment step, wherein said feed stock is transformed into a feed mixture in the form of a pumpable slurry or paste according to the present invention. Said addition may involve controlling the maximum particle size to less than 30 mm such as a particle size of maximum 15 mm, and preferably a particle size of maximum 5 mm such as a particle size of maximum 1 mm, and even more preferably a particle size of maximum 0.5 mm.

Depending of the character of the specific feedstock, said controlling of the particle size may comprise one or more of the operations of sieving, filtering, and/or settling operation and/or size reduction by one or more crushing, cutting, grinding, attriting and/or milling operations. The size reduction may in a preferred embodiment further be performed as an integral part of a pump for pressurizing said feed mixture such as a double or multiple screw extruders.

Control of maximum particle size in the pre-treating is important for the properties of the feed mixture and also for the mass- and heat transfer within the particles during said second step of converting.

A particularly preferred embodiment of the present invention further comprises adding at least one liquid organic compound in said first step of pre-treating. Said at least one liquid organic compound may comprise a range of different compounds including alcohols and polyalcohols, ketones, carboxylic acids, amino acids, aldehydes, ethers, esters, amines, amides, pyroles, indoles, catecols, phenols, piperidone, cyclopentanones, cyclopentenones, toluene, phenolic acids such as ferulic acid, benzoic acid, flavonoids such as flavones, flavenols, coumaric acid and/or cinnamic acid, hydroxycinnamic acid derivates, lignin monomers (monolignols) such as p-coumaryl alcohol, coniferyl alcohol and/or sinapyl alcohol and other phenol derivatives such as polyphenols, monomeric and oligomeric alkylated phenols, cresol, thymol, alkoxy phenols, alkylated cyclohexanes, alkylated cyclopentanes, toluene, mono- and polynuclear aromatic compounds such as substituted aromatics, quinone and benzon quinones, anthrax quinone, phenanthrene quinone, acenaphephthene quinone, chrysene quinone, diphenoquinone, stilbene quinone, naphodiqiuinones, tetraline, naphthenes, preasphaltenes, asphaltenes, polyaromatics, fatty acids, lipids, fat, waxes, paraffins, alkanes, alkenes and combinations thereof.

The effect of presence of said one or more liquid organic compounds according to the present invention may be multifunctional. They may work as a stabilizer and/or dispersant assisting in homogenizing the feed mixture such as lowering the viscosity and/or decreasing sedimentation and/or precipitation during said conversion process. They may further act as a solvent assisting in dissolving and/or extracting said carbonaceous material thereby lowering the viscosity of said feed mixture and/or enhancing the conversion towards desired products. Furthermore they may act as radical scavengers suppressing polymerization reactions such as tar and char formation and/or hydrogen donors during said conversion process thereby increasing the yield and quality of the desired liquid hydrocarbon products. In addition to this, said one or more organic liquid compounds may function as reactants that may be consumed and/or involved in said conversion process.

Said at least one liquid organic compound may be added as a single compound. However, in many embodiments according to the present invention said at least one liquid organic compound may comprise a range of organic compounds, and is preferably at least partly produced in situ in the process, and separated, recovered and recycled to said first step of pre-treating.

According to a preferred embodiment according to the present invention said one or more liquid compounds comprise a liquid hydrocarbon produced by the process or a fraction of said liquid hydrocarbon product produced by the process e.g. the heaviest fraction of said liquid hydrocarbons produced as further described and exemplified below. Further said one or more liquid hydrocarbons may or may further comprise water soluble organic compounds produced in the process.

Said one or more organic compounds is according to the present invention present in a concentration of at least 1% by weight such as at least 5% by weight. In a preferred embodiment of the present invention said one or more organic compounds is present in a concentration of at least 5% by weight such as at least 10 or at least 20% by weight.

In a preferred embodiment the weight ratio of the concentration of said one or more liquid organic compounds to the weight of dry solid carbonaceous material in said feed mixture is at least 0.01 such as a weight ratio of at least 0.025, and preferably said weight ratio is at least 0.05 such as at least 0.1 or at least 0.2, and preferably the ratio of the weight of said at least one organic compounds to the weight of dry solid carbonaceous material in said feed mixture is in the range 0.05 to 2, such as in the range 0.1 to 0.15 or in the range 0.10 to 1.0 and even more preferably the ratio of the weight of said one or more organic compounds to the weight of dry solid carbonaceous material in said feed mixture is in the range 0.15 to 0.75 such as in the range 0.2 to 0.5.

According to a preferred embodiment said at least one liquid organic compounds is/are at least partly produced within the process, and separated or recovered and subsequently recycled to said first step of pre-treating.

In a preferred embodiment according to the present invention said at least one liquid organic compound being added in said pretreatment step comprise liquid hydrocarbon product produced by the process and/or a fraction of said liquid hydrocarbon product produced by the process such as the heaviest fraction of said hydrocarbon product.

In another preferred embodiment according to the present invention said at least one liquid organic compound comprise or further comprise water soluble organics produced in the process and recovered from said residual fraction.

Advantageously said first step of pre-treating further comprise controlling the concentration of at least one homogeneous catalyst in the form of potassium and/or sodium to a total concentration of at least 0.5% by weight.

Said controlling may be performed by measuring and adjusting the concentration of potassium and/or sodium e.g. by, adding potassium and/or sodium in the form of a salt and/or a solution. Preferred forms of potassium and/or sodium according to the present invention include potassium hydroxide, sodium hydroxide, potassium carbonate, sodium carbonate, potassium bicarbonate, sodium bicarbonate, potassium formate, sodium formate, potassium acetate, sodium acetate, potassium citrate, sodium citrate. In some embodiments of the present invention said addition of potassium and/or sodium at least partly include mixing a feedstock with a high content of potassium with a feedstock having a lower content of potassium and/or sodium.

The process according to the present invention is advantageously carried out under alkaline conditions i.e. the pH is maintained at a value above 7 such as a pH in the range 7 to 14, and preferably in the range 8 to 12 such as a pH value in the range 8 to 10. Operation under such alkaline conditions assists in partly decomposing said carbonaceous material at least by alkaline hydrolysis during said pre-treatment, whereby the viscosity of said feed mixture for many carbonaceous materials according to the present invention decreases and thereby becomes easier to pump. Alkaline conditions during said conversion minimize corrosion, and also assist in suppressing undesired side reactions.

Hence, the first step of pre-treating in many embodiment of the present invention includes measuring and adjusting the pH to obtain a pH value in the above preferred ranges. Said adjustment of pH may according to the present invention be by adding a base. Said base may be the same potassium and/or sodium source as used for control of said at least one homogeneous catalyst, but may also be another base such as ammonia and/or urea.

The feed mixture according to an embodiment the present invention further comprise water in an amount of at least 25% such as at least 40%, and preferably the water content of said feed mixture is in the range 30 to 80% such as in the range 30 to 70%.

The first step of pre-treating according to the present invention is in a preferred embodiment at least partly performed in a stirred vessel such as a planetary or Banbury mixer capable of efficiently mixing and homogenizing highly viscous feedstock. The stirred vessel may further be equipped with means such as a heating jacket so as to preheat the feed mixture to a temperature in the range 50 to 200° C. such as 90 to 160° C. at a sufficient pressure to keep the feed mixture below the boiling point such as a pressure in the range 1-20 bar such as 4 to 20 bar. The energy needed for the preheating of said feed is preferably supplied by recovering heat from one of the process streams to be cooled such as e.g. the cooled the product stream after heat exchange with e.g. the incoming feed in the heating step of the conversion.

An embodiment of a preferred first step of pre-treating according to the present invention. Many feedstocks according to the present invention are viscous, wet and comprise fibrous material. It is well known that such fibrous material can be difficult to pump and may block orifices and contra valves in pumps etc. Many size reduction techniques for such fibrous materials are available for dry materials e.g. knife, hammer, and stone mills or combinations thereof. Further a wide range of techniques are available for wet materials at low materials including different kind of wet milling techniques such as ball mills, colloidal mills, cutting mills, macerators, etc.

An alternative preferred embodiment of a pre-treatment according to the present invention include feeding one or more feedstock containing said carbonaceous material to be converted to agitated vessel comprising a high shear mixer e.g. a planetary mixer such as a Kneader mixer or a Banbury mixer. Additives such as liquid organic compounds and/or homogeneous catalyst is/are added in concentrations as described in relation to FIG. 1, an pH is adjusted to a value in the range 8 to 12 by addition of a base such as sodium hydroxide and/or potassium hydroxide. The mixture is preheated to a temperature of 50 to 200° C. at a pressure sufficient to prevent the mixture from boiling e.g. a pressure in the range 1 to 20 bar and mixed and homogenized in a predefined time e.g. from 5 hours minutes to 24 hours such as from 10 minutes to 12 hours and preferably said predefined time for pretreatment is in the range 15 minutes to 6 hours such as a predefined time in the range 20 minutes to 3 hours. During said pre-treatment for a predefined time said feedstock is softened and size reduced and the viscosity in lowered and a homogenous paste is produced. The process may be pictured as the softening of vegetables being cooked and subsequently blended in a kitchen.

The pre-treated and optionally preheated feed mixture is withdrawn from the pre-treatment step and is converted by first pressurizing the feed mixture to an operating pressure for said conversion in the range 250 to 400 bar, and even more preferably in the range 275 bar to 350 bar such as in the range 300 to 350 bar.

Said pressurization may be performed in one or more steps. Suitable pumps for pressurization include positive displacement pumps such as reciprocating or rotary vane or gear pumps. Examples of preferred pumps include rotary lobe pumps, progressing cavity pumps, rotary gear pumps, pisto pumps, screw pumps, vane pumps and diaphragm pumps. A particularly preferred pressurization system according to the present invention includes a auger pump such as a double and/or multiple augers pumps. The rotating augers preferably in such pressurization system preferably comprise augers with variable pitch such as screws and/or diameter. Another preferred pump according to the present invention includes a hydraulically driven piston or plunger pump, which may be single or double acting. For said piston or plunger pumps, it is generally preferred that the duration of the stroke is relatively long e.g. in the range 0.5 to 60 min per stoke such as in the range 1 minute to 30 minutes, preferably the duration of said strokes are in the range 1 to 20 minutes per stroke such as in the range 1 to 15 minute per stroke. Still another preferred embodiment according to the present invention comprises a first step of pressurization using a double or multiple screw system and a second pressurization system comprising a hydraulically driven piston or plunger.

The pressurized and pre-treated feed mixture is subsequently heated to the operating temperature for said conversion in one or more steps. The operating temperature may according to the present invention be in the range 360 to 450° C., and even more preferably in the range 370 to 430° C. such as in the range 385 to 415° C.

The heating is preferably at least partly performed by recovery of heat from one or more of the process streams to be cooled such as the hot raw product stream being withdrawn from said conversion step to maximize the thermal efficiency of the process. This may according to a preferred embodiment of the present invention be performed by direct heat exchange between the incoming feed mixture and the outgoing raw product stream as indicated in FIG. 1. In an optional embodiment the heat exchange may be performed by indirect heat exchange with a heat transfer medium such as steam, hot oil or molten salt transferring heat from hot process streams to the cold process streams.

A further heating step using an external heat source is required to heat and trim the temperature of feed mixture to the desired operating temperature. This heating may be performed by direct heat exchange of the partly heated feed mixture with a heating fluid such as steam or with hot flue gas from a burner or furnace.

In accordance with the invention the steam may comprise steam from an external process such as hot low pressure steam from a turbine. The steam may be further heated by an external heat source before heat exchange with the partly heated feed mixture to obtain specific heating rates and/or to minimize the heat transfer surface area required.

In the embodiment of the present invention, wherein the heating fluid comprises hot flue gas from a burner, said burner may be a furnace comprising heat transfer surfaces for further heating said partly heated feed mixture or the hot gas may be transferred to an external heat exchanger for said heat exchange. In both cases it is greatly preferred that the fuel for said burner or furnace is at least partly comprised by combustible gases produced by the process. The co-combustion of such combustible gases produced by the process in said burner and/or furnace increases the overall thermal efficiency of the process and/or reduces waste streams from the process by destroying pollutants, whereby some objectives of the current invention are accomplished.

In another advantageous embodiment accordance with the present invention said further heating of the partly heated feed mixture to the desired operating temperature for said conversion may comprise indirect heat exchange with a heat transfer medium such as hot oil or a molten salt. External heat may at least partly be transferred to said heat transfer medium in a burner and/or furnace. Said burner may advantageously comprise co-combustion of gas produced in the process, and/or be equipped with means for recirculation of flue gas in a similar manner as described above.

Furthermore an embodiment for heating said partly heated feed mixture in accordance with the present invention comprises or further comprises direct injection of steam and/or an oxidizing agent as further described and illustrated in relation to FIG. 4-7.

It is advantageous that said heating is not too slow and advantageously fast. Hence, in a particular preferred embodiment the heating rate in the temperature range 140° C. to 300° C. is preferably at least 50° C./min such as 75° C./min and preferably at least 100° C./min such as at least 150° C./min. The residence time for said conversion to proceed at the desired operating pressure and temperature may according to the present invention be in the range 1 to 60 minutes such as in the range 5 to 45 minutes, and preferably the residence time is in the range 10 to 40 minutes such as a residence time in the range 10 to 35 minutes, and even more preferably said residence time is in the range 10 to 30 minutes such as in the range 10 to 25 minutes.

The process according to the present invention is preferably a continuous process, and may be performed in a substantially in a plug flow of the feed mixture. The flow velocities in pipes are according to an embodiment of the invention further selected so as to minimize sedimentation or precipitation of particles that may be suspended or formed during said conversion process e.g. by keeping at velocity in said pipes of at least 0.20 m/s such as at least 0.5 cm/s, and preferably in the range 0.2 to 5 m/s second such as 0.5 to 3 m/s.

The residence time needed may according to the present be obtained by applying one or more long tubes preferably vertically arranged and connected with bends designed to minimize dead zones that could cause settlement. Flow velocities in said reactor tubes should preferably be maintained within the above ranges to minimize that the risk of sedimentation and clogging of said tubular plug flow reactor(s).

In an advantageous embodiment said predefined residence time is at least partly obtained in one or more reactors. Said reactor(s) may in accordance with a preferred embodiment of the invention be fed from the top and have an outlet in the bottom to avoid sedimentation of suspended particles in the reactor. Furthermore in an optional and advantageous embodiment of the present invention said reactor has/have a conical inlet whereby a controlled decrease of the flow velocity in the pipe is performed and/or a conical outlet whereby the flow velocity is increased in a controlled manner to a flow velocity corresponding to the pipe velocity. An example of a preferred reactor design according is shown and described in FIG. 2.

Whereas embodiments of present invention typically allow for management of suspended particles without substantial sedimentation, precipitation or fouling even when processing feedstock having a high ash content, it may be beneficial to at least partly separate said particles from said fluid containing converted carbonaceous material while its hot, thereby e.g. reducing downstream separation needs. Suitable means for such particle separation include one or more gravimetric settling chambers, inline filters and/or hydrocyclones or combination thereof.

Figure 4:
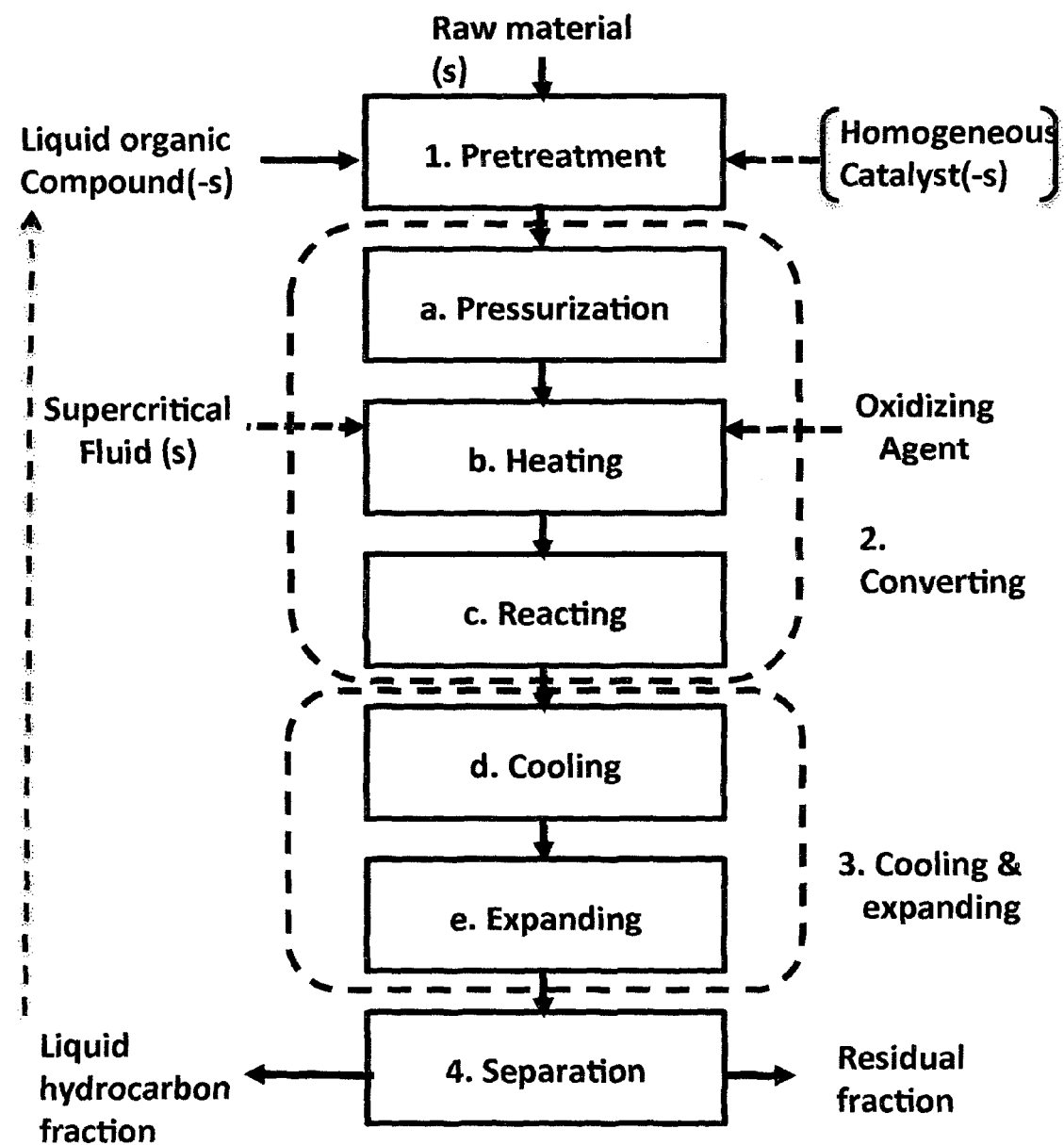
FIG. 4 shows a schematic diagram of an embodiment of a conversion process according to the present invention.

In another embodiment according to the present invention said means and/or reactors for maintaining the residence time within the desired range of operating conditions may or may further comprise a chamber, wherein said suspended particles are at least being partly separated. A preferred embodiment include a residence chamber, wherein the fluid comprising converted carbonaceous material and suspended particles are fed tangentially into a cylindrical chamber and/or cyclone shaped chamber having a conical outlet, and an inner pipe in the centre extending from the top to the start of conus as the outlet for said fluid a containing converted carbonaceous material. Particles are separated by a combination of gravity, centrifugal forces and forced downwards flow. The chamber may further comprise means for continuous removal of said particles e.g. as a brine. An example of a preferred chamber for at least partial removal of particles is shown in FIG. 4.

Subsequent to said second step of converting the fluid comprising converted carbonaceous material is cooled to a temperature in the range 25 to 150° C. and expanded to a pressure in the range 1-25 bar in a third step of cooling and expanding. Said cooling is preferably performed by heat exchange with said incoming feed mixture in one or more steps as described above.

The expansion in third step of cooling and expanding may be performed prior to a last step of cooling e.g. by cooling to a temperature in the range 100-200° C. such as 150° C. by direct heat exchange with the incoming feed mixture. This allows for a less expensive cooler for the last part of the cooling as this only requires operation at a pressure of 1-25 bar. A second step of said fluid comprising converted carbonaceous material may comprise cooling by preheating the feed mixture in said first step of preheating and/or for producing steam for export to e.g. an external process. A preferred expansion system according to the present invention include means, wherein the major part of the depressurization is performed by creation of a dynamic pressure drop in a system of small pipes and/or capillaries of predefined length and at least one control valve. The small pipes and/or capillaries may comprise pipes and/or capillaries of different lengths and dimensions in a series and parallel arrangement. Different combinations of lengths and dimensions of tubes/capillaries may be chosen automatically to account for variations of properties of the feed mixture e.g. during start up and shut down. The control valve is used to fine tune the operating pressure by establishing a back pressure as well as balancing the outgoing flow with incoming flow and making the final expansion. In case of a further cooling step subsequent to the first part of the expanding step the control valve is preferably positioned subsequent to said cooling. The pressure drop over the expansion valve is according to the present invention up to 50 bar such as up to 30 bar, and preferably in the range 5 to 30 bar. The division of expansion into two or more steps in said third step of cooling and expanding into a dynamic pressure drop and one or more control valve(s) reduces wear and makes the system less susceptible to suspended particles e.g. the system is capable of handling higher amounts of suspended particles without being worn out. Another preferred embodiments for expanding said according to the present invention include a depressurization in a pressure left down engine.

The cooled and expanded fluid containing converted carbonaceous material from said third step of cooling and expanding is subsequently lead to a fourth step of separating from said mixture at least a residual fraction and a fraction comprising said liquid hydrocarbon.

The fluid containing converted carbonaceous material may comprise liquid hydrocarbon product, a water phase containing water soluble organic compounds and salts, gas and suspended particles.

According to a preferred embodiment of the present invention said fourth step of separating comprises means for separating gas from said mixture such as a degasser and/or a multiphase gravimetric separator equipped with means for withdrawal of gas and/or comprising different liquid outlets for withdrawing different liquid streams such as a liquid hydrocarbon rich phase and/or a water rich phase and/or particle rich stream.

A preferred option comprises separation means to for degassing and a at least coarse separation of said mixture into a liquid hydrocarbons rich stream and a residual fraction stream preferably after degassing. The gas from said degassing step is preferably fed to burner and/or furnace to supply heat to the process as described above.

The means for separating may comprise or further comprise centrifugation such as by centrifugation in one or more disc centrifuge(s) and/or basket centrifuge(s) for separation of said liquid hydrocarbons and/or water and/or suspended. The fourth step of separating may in accordance with the present invention include a series of such centrifuges operating in both a clarification and purification mode thereby separating the mixture containing fluid, converted carbonaceous material into a liquid hydrocarbon fraction, and a residual fraction containing water and water soluble organics and salts and optional a third fraction containing suspended particles. In some applications according to the present invention it may be advantageous to add an acid such as acetic acid to enhance the separation of liquid hydrocarbons and water. Said acidification may according to the present invention be performed by acidifying the mixture before the first step of centrifugation, but may according to an advantageous embodiment be performed only on liquid hydrocarbon fraction obtained after a first centrifugation step. Further liquid hydrocarbons recovered after an optional purification step of said the water phase may according to the present invention preferably be recycled and mixed with the liquid hydrocarbon fraction before said step of purification of said liquid hydrocarbons.

In an alternative preferred option in accordance with the present invention, said fourth step of separating include means for first degassing said mixture and subsequently recovering a liquid hydrocarbon fraction and a residual fraction by gravitational settling such as in a three phase separator.

The liquid hydrocarbon product and said residual fraction obtained from said fourth step of separating according is crude products, each of which according to the present invention may be subjected to further treatment.

Figure 2:
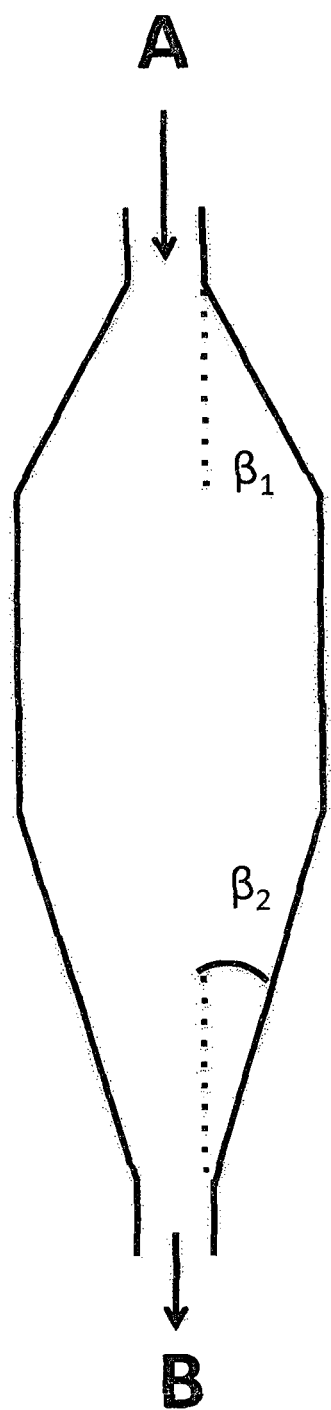
FIG. 2 shows a schematic drawing of a reactor design according to the present invention.

FIG. 2 shows an example of a preferred of a reactor design according to the present invention. Said feed mixture A to be converted is fed from the top and withdrawn from reactor the bottom as the stream B. Feeding the reactor from the top have the advantage of that the velocity in the reactor can be decreased without the risk of particles sedimenting. Hence, relatively low velocities in the reactor is possible without the risk of clogging due to sedimentation of particles, thereby resulting in a robust, compact and economically attractive design of said reactor(-s) allowing for high amounts of suspended particles.

The average velocity of the feed mixture in the inlet to said reactor is preferably at least 0.2 m/s such as in the range 0.2 to 5 m/s such as in the range 0.2 to 3 m/s.

The velocity in said reactor is preferably decreased in a controlled manner such as introducing said feed mixture into the reactor in a conically shaped entrance to the reactor. In a preferred embodiment the angle of the walls to the centreline of said reactor, $\beta_1$, is preferably below 60° such as at below 45°, and preferably said angle $\beta_1$ is below 30° such as below 20°, and even more preferably said angle is below 15°.

The ratio of the average inlet velocity to the reactor to the minimum velocity in said reactor is preferably above 4 such as above 16 and preferably above 25 such as above 50.

The outlet of said reactor is preferably also conically shaped with an angle of the outlet conus to the centreline of said reactor, $\beta_2$, being below 30° such as below 20°, and preferably said angle of the outlet conus to the centreline of said reactor, 132, is below 15° such as below 10° to avoid build up of particle sediments at the walls of said outlet conus.

The residence time in said reactor is preferably in the range 5 to 45 minutes, such as in the range 10 to 40 minutes, and preferably in the range 10 to 35 minutes such as in the range, and even more preferably in the range 10 to 30 minutes such as in the range 10 to 25 minutes.

A process in accordance with the present invention may comprise several of such reactors in a series and parallel arrangement. A preferred embodiment of a reactor in series arrangement include of reactors in series said reactors is connected by a piping with velocities selected according to the present invention, and having bends with dimensions and angles selected so as to eliminate dead zones and to avoid sedimentation of particles. The velocity in the pipes is selected according to the guidelines given in the description relation to FIG. 1 and the angles of the beds may be selected to e.g. 180°.

In the case of reactors in series the total residence time should be maintained within the above ranges including the residence time in the connecting pipes.

Figure 3:
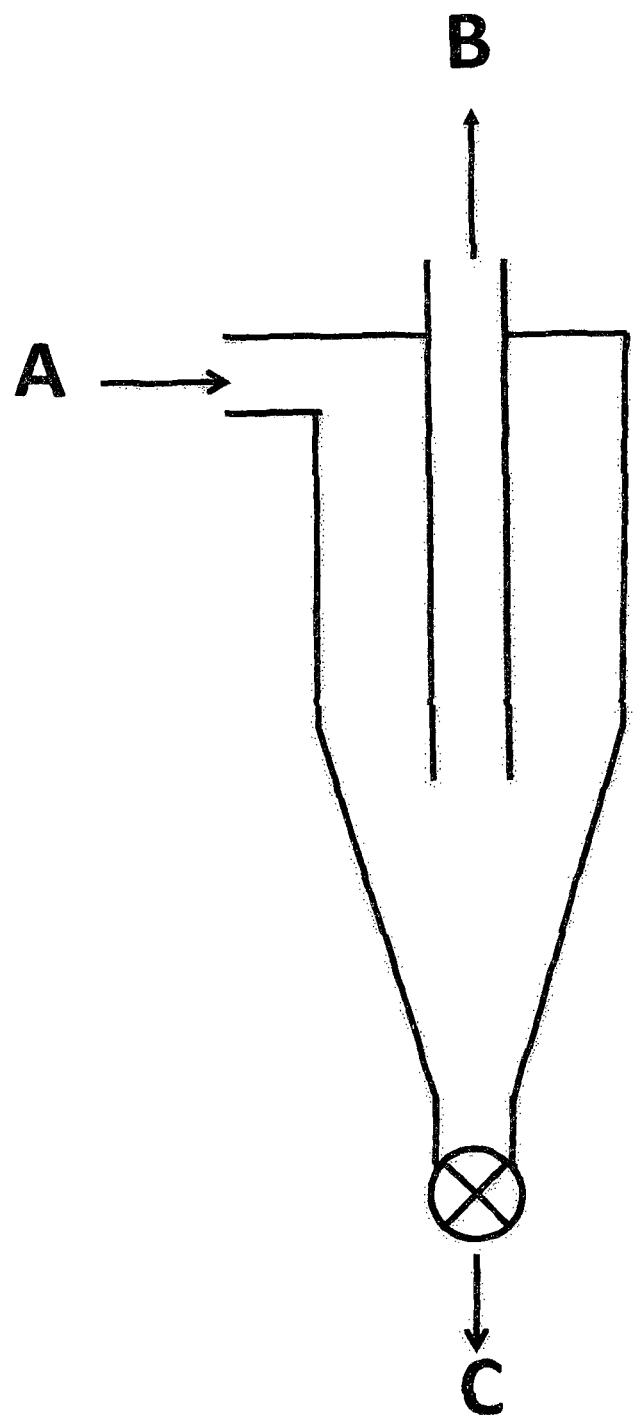
FIG. 3 shows a schematic drawing of an example of a preferred design of a particle separator according to the present invention.

FIG. 3 shows an example of a preferred design of a particle separator according to the present invention. The converted feed mixture according to the present invention contains suspended particles. Often liquid hydrocarbons are adsorbed to said suspended particles at least a low temperature, which may make it difficult to separate said from said liquid hydrocarbons and water phase at low temperature. Adsorption equilibria are temperature sensitive and therefore it may at least for some feedstock containing high amount of ash particles be advantageous and economical to at least partially separate said suspended particles from said feed mixture comprising partially converted or fully converted carbonaceous material at temperature and pressure. In a preferred embodiment this is performed in a particle separator as shown in FIG. 3. The feed mixture A is introduced tangentially into a cyclone shaped chamber thereby introducing both a centrifugal force and a forced downwards flow of the suspended particles as well as by gravity. The feed mixture depleted in particles is collected in a central pipe extending at least to the conus of said cyclone shaped chamber. Particles are allowed to build up in the conus and are according to an embodiment withdrawn from the separator in a continuous or semi-continuous manner. A particle separator according to an embodiment of the present invention further comprises means for removing particles from said particle separator system. Said means may according to an embodiment of the present invention comprise a lock hooper system. Further said particle withdrawal system according to the present invention may comprise a heat recovery system.

FIG. 4 shows a simplified drawing of another preferred embodiment according to the present invention. The preferred embodiment and features of the process may be as described in relation to FIG. 1-3, but according to this preferred embodiment of the present invention, the heating in said second step of converting comprise or further comprise heating by direct injection of an external heating medium such as a superheated supercritical fluid such as superheated steam and/or by addition of an oxidizing agent in a predefined amount to provide heat by partial combustion or partial oxidation of said carbonaceous material internally in the process.

The oxidizing agent may according to the present invention be selected from oxygen, oxygen enriched air, air or hydrogen peroxide and may according to the present invention be added in an amount so as to convert up to 25% of the energy contained in said feed mixture to heat such as up to 15% of the energy contained in said feed mixture, and preferably the amount of said oxidizing agent being added is controlled to convert up to 10% of the energy contained in said feed mixture such as up to 5% of the energy contained in said feed mixture.

The superheated supercritical fluid is in accordance with the present invention preferably at least partly generated within the process and reused. This may according an embodiment of present invention be performed by including one or more flashing steps during said third step cooling and expanding, condensing water from the vapour phase, and applying means for superheating and re-pressuring said vapour e.g. by superheating in an external furnace.

Figure 5:
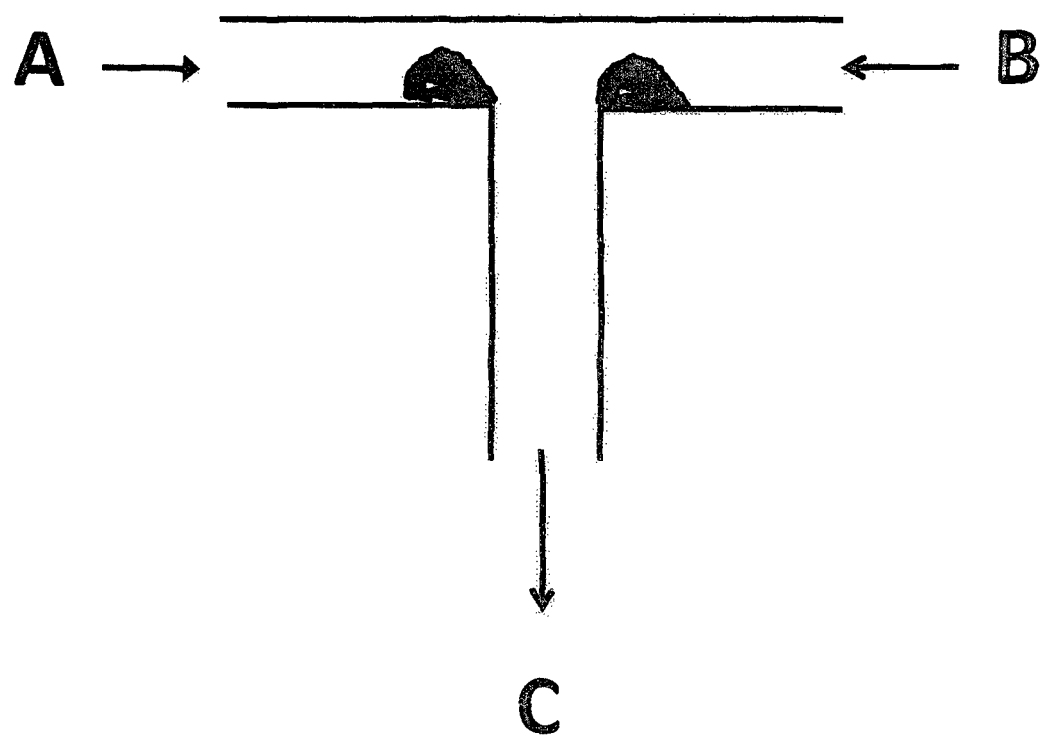
FIG. 5. shows an embodiment of an example of a conventional mixing zone for introducing and mixing a supercritical fluid into a colder feed mixture.
Figure 6:
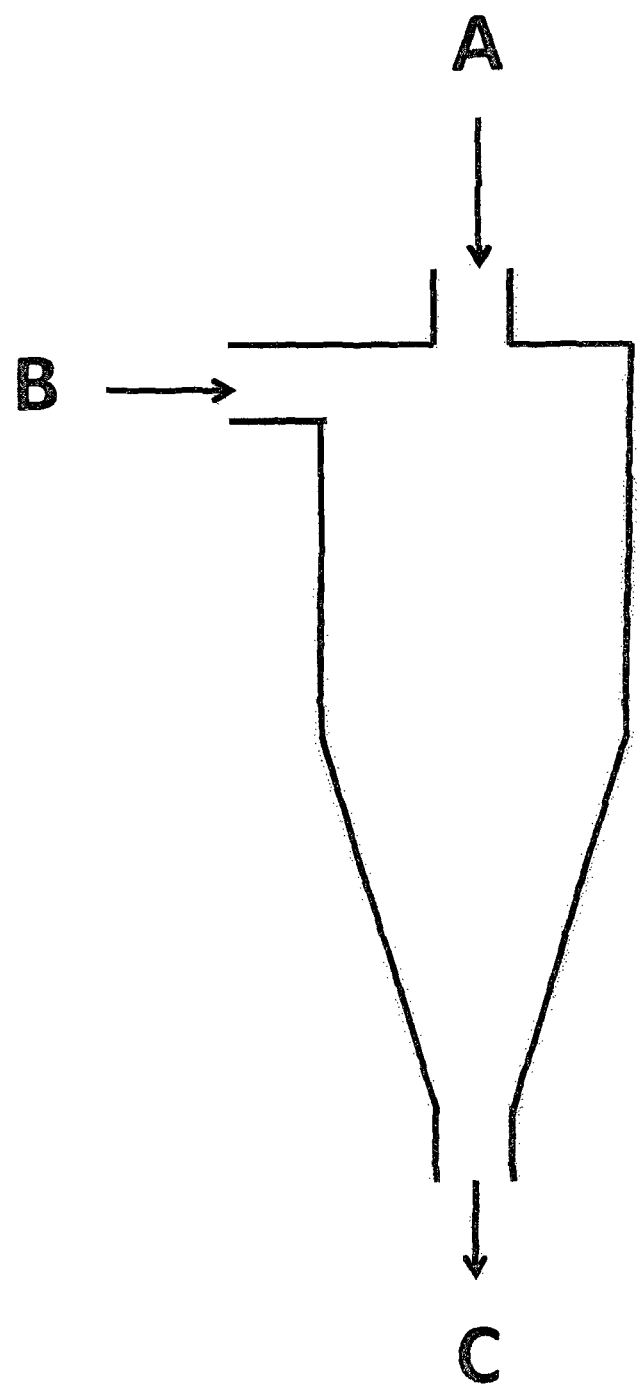
FIG. 6. shows a preferred embodiment of a mixing zone for introducing and mixing a supercritical fluid into a colder feed mixture according to the present invention.
Figure 7:
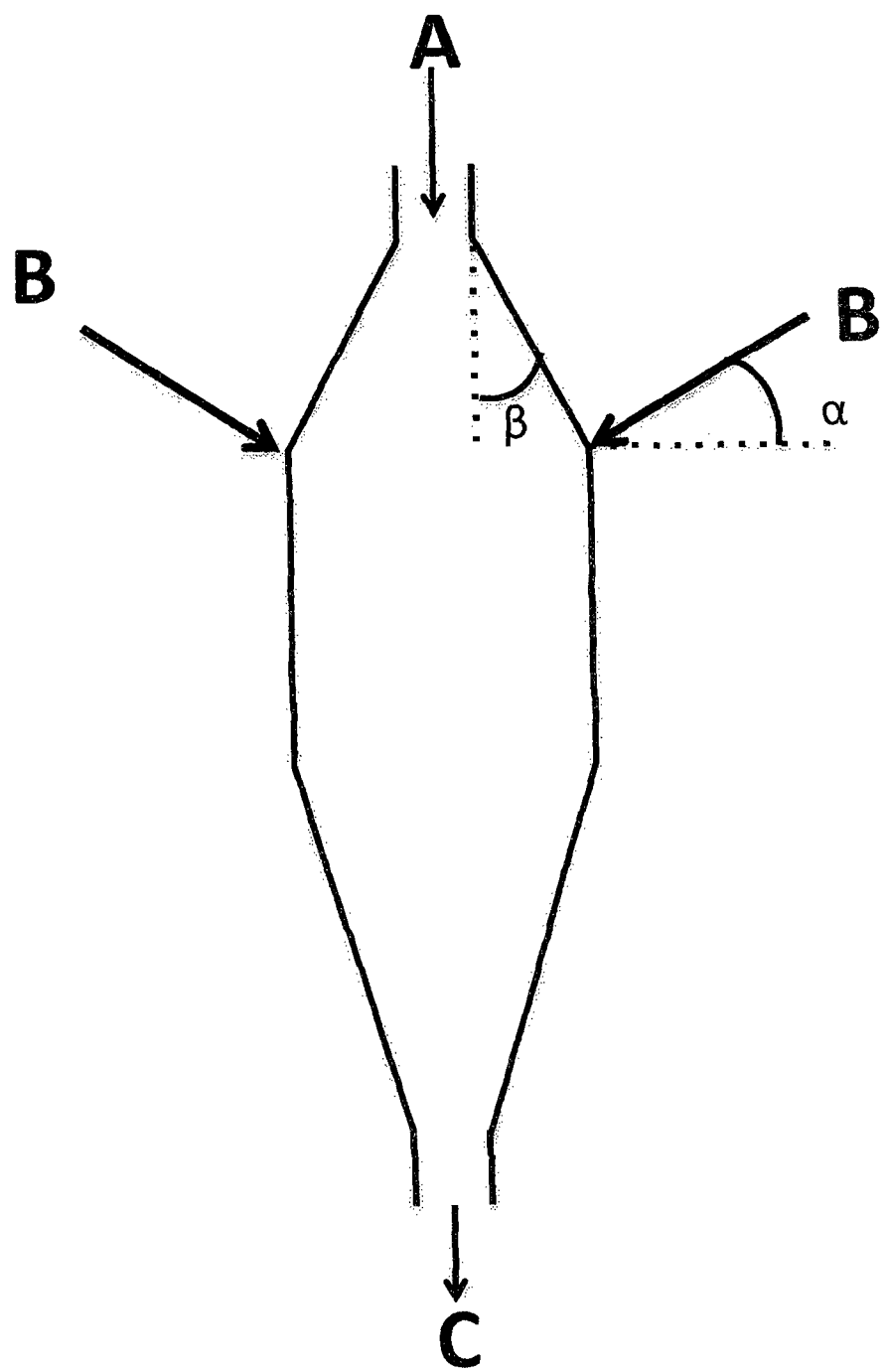
FIG. 7. shows an example of an advantageous embodiment of a mixing zone for introducing and mixing a supercritical fluid into a colder feed mixture according to the present invention.

FIGS. 5-7 show different embodiments of a mixing zone for introducing a superheated supercritical fluid as described in relation to FIG. 4 into a colder feed mixture. Mixing such hot superheated supercritical fluid into a colder feed mixture may provide a very fast and efficient method of heating and partly converting such feed mixtures thereby lowering the viscosity of said feed mixture and allowing for more a more efficient and economical heat exchanger design.

However, rapid change of temperature under hydrothermal conditions also leads to a rapid change of the ionic product of water and thereby the solubility of salts. Salts may be present both as dissolved in said feed mixture and may be released. Hence, such salts may crystallize, precipitate and sediment and clog the mixing point or piping over time. Hence an object and an aspect of the present invention may be to provide a mixing zone design that are less sensitive, more robust and allows for less down time.

FIG. 5 shows an example of a conventional mixing zone design, wherein a hot and a cold fluid are mixed in a mix zone in a T-connection. For illustration it is assumed that the hot flow and cold flow are identical and the pipe dimensions of the connecting pipes are the same and the flow velocity of the combined flow subsequent to mixing is kept the same. As illustrated it has been found that precipitation and sedimentation build up in stagnant regions around both corners of the connecting pipes, and over time will tend to block the pipe. Hence, such design is not considered as a solution according to the present invention. Similar considerations may be applied to Y-shaped mixing zones.

It has been found that a significant improvement is obtained, if the two fluid streams to be mixed are expanded into a common mixing chamber. Further it has been found that the ratio of the average linear velocity in the inlet pipe(s) to the minimum average velocity of the mixed flow ($V_{pipe}/V_{mixed,min}$) should preferably be maintained at a minimum of 2 such as a velocity ratio of at least 4, and preferably said velocity ratio is maintained at a minimum of 8 such as a velocity ratio of at least 16. As the viscosity of the colder feed mixture in most applications according to the present invention are much higher the velocity ratio it is often preferred to keep the velocity ratio of the feed mixture in the lower end of the above ranges in order not to offset improved mixing and less sensitivity towards clogging by too high pressure drops. However, it is often advantageous to maintain the velocity of the superheated supercritical fluid at a high velocity ratio to improve mixing.

FIG. 6 shows a preferred embodiment of a mixing zone according to the present invention. The feed mixture, A, is introduced in the centre from the top of a cyclone shaped mixing chamber and the superheated supercritical fluid, B, is introduced substantially tangentially to said mixing chamber. Both fluid streams are introduced with an average velocity ratio of at least 2. The superheated supercritical fluid, B, may be introduced in one or more inlet at a velocity ratio of at least 4 such as a ratio of at least 8, thereby creating a swirl mixing in said chamber. The combined flow of said partially or fully converted feed mixture, C, is withdrawn from said cyclone shaped mixing chamber from the bottom.

It should be noted that the mixing zone may be suitably combined with the preferred reactor design described in FIG. 2. e.g. the mixed stream. C in FIG. 6 may advantageously be introduced at the position A in FIG. 2.

FIG. 7 shows an example of an advantageous embodiment of a mixing zone according to the present invention. The feed mixture A is introduced into the mixing chamber from top in the centre. The mixing chamber has a conically shaped inlet with an angle of the walls to the centreline of said reactor, $\beta_1$. The angle $\beta_1$ is preferable below 60° such as at below 45°, and preferably said angle $\beta_1$ is below 30° such as below 20°, and even more preferably said angle is below 15°.

The superheated supercritical fluid, B, is preferably introduced into said chamber at one or more inlets having an angle $\alpha$ in the flow direction to minimize back-mixing towards the inlet for said feed mixture. To maximize the penetration and mixing of said superheated supercritical fluid into said feed mixture, it is preferred that said superheated supercritical is introduced, when said the velocity of said fed mixture has been decelerated to substantially its minimum velocity in said chamber e.g. after the conical inlet for said feed mixture.

The angle $\alpha$ is according to an embodiment of the present invention preferably at least 20° such as at least 30°, and preferably said angle is at least 45°. The average velocity of the feed mixture in the inlet to said reactor is preferably at least 0.2 m/s such as in the range 0.2 to 5 m/s such as in the range 0.2 to 3 m/s.

The ratio of the average inlet velocity of the superheated supercritical fluid, B, to the average minimum velocity in said reactor is preferably above 4 such as above 16 and preferably above 25 such as above 50.

The outlet of said reactor is preferably also conically shaped with an angle of the outlet conus to the centreline of said reactor, $\beta_2$, being below 30° such as below 20°, and preferably said angle of the Outlet conus to the centreline of said reactor, $\beta_2$, is below 15° such as below 10° to avoid build up of particle sediments at the walls of said outlet conus.

The residence time in said chamber is preferably in order of seconds such as in the 1 to 60 s, and preferably said residence time is in the range 1 to 30 seconds.

Figure 8:
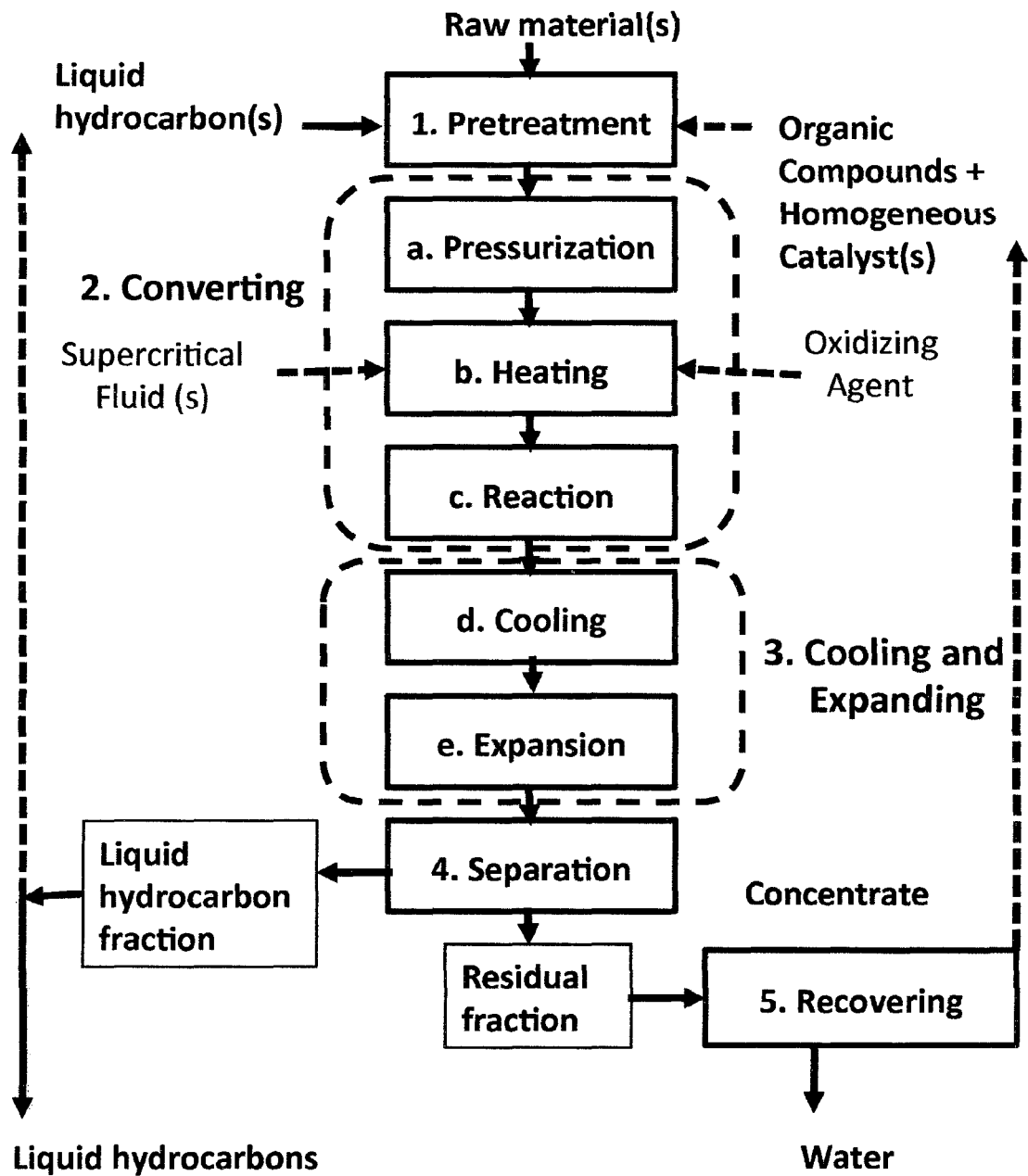
FIG. 8 shows a schematic diagram of a hydrothermal process for conversion of carbonaceous material according to the present invention comprising a fifth step of recovering substances from the residual fraction.

FIG. 8 shows a schematic drawing of an advantageous embodiment according to the present invention comprising a first step of pre-treating, a second step of converting, a third step of cooling and expanding, and a fourth step of separating the fluid comprising converted organic material at least into a fraction comprising liquid hydrocarbons and a residual fraction according to any of the embodiments described above in relation to the FIG. 1-7 further comprising a fifth step of recovering liquid hydrocarbon compounds and homogenous catalyst from said residual fraction.

The residual fraction according to the present invention comprises a water phase that may contain dissolved homogenous catalysts such as potassium and/or sodium. Whereas beneficial for the conversion the carbonaceous material such homogeneous catalysts are relatively expensive and may constitute a major operating cost. Further in many applications of the present invention between 10 to 30% of the energy may be contained in said carbonaceous material contained in said feed mixture is converted into water soluble organic compounds contained in said water phase. The presence of these liquid organic compounds in the water phase represent both a process loss reducing the thermal efficiency of the process, and put further requirements to purification of the water effluent from the process.

An advantageous embodiment of the present invention include a fifth step of recovering comprising at least partly recovering homogenous catalyst in the form of potassium and/or sodium and/or liquid organic compounds from said water phase in a concentrated form ("concentrate") and recycling said concentrate to said first step of pre-treating. Hence, such embodiment according to the present invention improves the process economy by reducing operating cost, improving energy efficiency of the overall process and increasing yield of said desired liquid hydrocarbons.

A preferred fifth step of recovering in accordance with the present invention comprises concentration by an evaporation technique. Said evaporation may be performed in a falling or rising film evaporator and may comprise a multi-effect evaporator comprising 2 or more stages. It is further preferred that at least the first evaporator is equipped with means for vapour compression such as mechanical vapour recompression (MVR) and/or thermal vapour recompression to (TVR) or a combination thereof. In a preferred embodiment steam for heating and/or thermal recompression such as by thermal recompression is produced by the process and thereby reducing the energy requirements for said evaporation and the overall thermal efficiency of the process.

Many applications according to the present invention comprises concentrating water phase at least by a factor of 4 such as a concentration factor of at least 5 preferably said water phase is concentrated by at least a factor of 7 such as a concentration factor of at least 10 on a mass basis.

The amount of liquid organic compounds recovered from said water phase (residual fraction) in said concentrate in said fifth step of recovering and being recycled to said is according to an embodiment at least 80% of the water soluble organics in the put stream to said fifth step of recovering measured as the concentration of total organic carbon present in input water phase. Preferably at least 85% of the water soluble organics in said water phase is recovered, and even more preferably the amount of liquid organic compounds recovered from said water phase is at least 90% such as at least 95%.

Further the amount of homogenous catalyst in the form of potassium and/or sodium recovered from said water phase being fed to said fifth step of recovering is at least 90% such as at least 95% and preferably more than 99%.

The last step of said evaporator in said fifth step of recovering is according to a preferred embodiment of the present invention further equipped with means for condensing said vapour phase from said last evaporator stage in two or more steps of condensing having a decreasing condensation temperature so as to condense compounds having a boiling point lower than water in said second or third step of condensing. Alternatively said compounds may be condensed in the same step as water by selecting the condensation temperature so as to condense such compounds. Said condensation temperature in said last step of condensing may be selected to have a condensation temperature of 40 to 60° C., so as to condense compounds having a boiling point lower than water, and at the same time minimize the mixing of these lower boiling liquid organic compounds with the evaporated water. Hereby it is not only obtained that said compounds having a boiling point lower than water is recovered and may be recycled to the process, but also that the evaporated water are cleaned to a level where it in many applications may be directly used e.g. for irrigation or discharged e.g. to sewer.

The condensed water phase from said evaporation system according to the present invention may comprise an organic compounds corresponding to a concentration of less than 0.1-5 g/l such as a TOC concentration of less than 0.1-2 g/l. The water phase may in many applications according to the present be clean enough for use as technical water internally or for irrigation purposes. Optionally a further polishing treatment may be performed.

Depending on specific local requirements and conditions suitable technologies for such polishing according to the present invention include biological treatment systems such as membrane bioreactor and photo bioreactors. An example of such system is the Bio-gill membrane bioreactor system (www.biogill.com). Other technologies may include photocatalysis, ozone/UV treatment, chromatographic separation systems and membrane systems such as reverse osmosis, nanofiltration, ultrafiltration, electrodialysis, dialysis and pervaporation and combination thereof.

In accordance to another embodiment of the present invention said fifth step of recovering may comprise an aquaculture for production of biomass such as algae and/or bacteria such as cyano bacteria, and recycling said biomass to the first step of pre-treating after dewatering in a decanter centrifuge and/or a filter press, and/or a screw press and/or a membrane filter. Said aquaculture may comprise a bioreactor such as a photobioreactor including open ponds.

Figure 9:
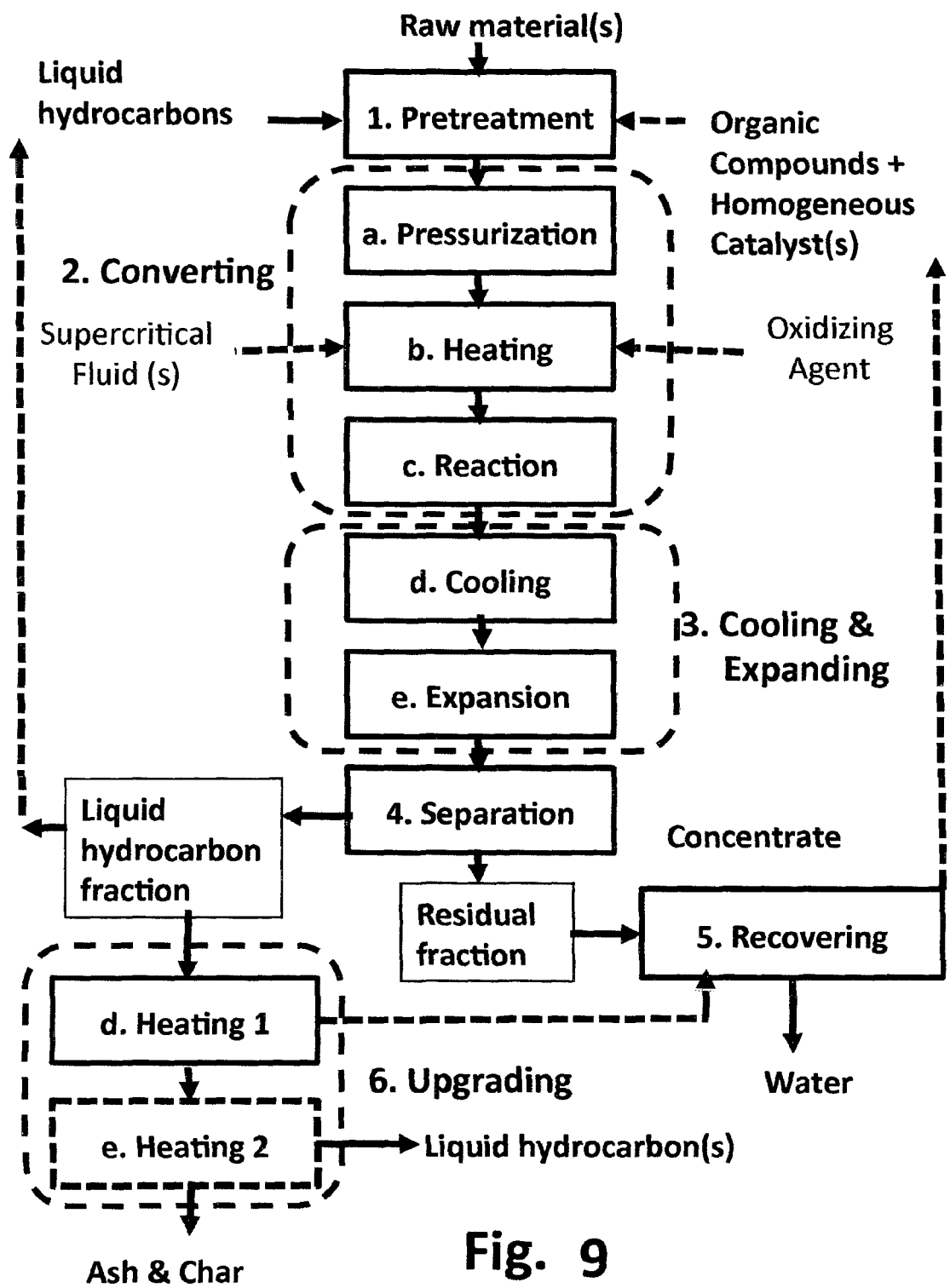
FIG. 9. shows a schematic diagram of a hydrothermal process for conversion of carbonaceous material comprising a $6^{th}$ step of upgrading the liquid hydrocarbon fraction.

FIG. 9 shows an embodiment of the present invention further comprising a sixth step of upgrading the liquid hydrocarbon fraction by heating in one or more steps.

Depending on the specific feedstock, processing conditions and process configuration the liquid hydrocarbon fraction after said fourth step may comprise a crude oil, which may contain more or less water, more or less ash and salts, a relatively high acid number and/or high viscosity. The liquid hydrocarbon fraction may be of sufficient quality for direct use e.g. as a heavy fuel oil or coal substitute in industrial combustion applications. The liquid hydrocarbons may also be of sufficient quality for upgrading to transportation fuels like in a conventional large centralized refinery. However in many cases according to the present invention it is desirable to further upgrade the liquid hydrocarbon fraction so it has more and higher value direct applications.

Hence an embodiment of the present invention comprises the steps and features described in relation to FIGS. 1-8 and further a sixth step of upgrading said hydrocarbon fraction by heating. Said sixth step of upgrading is preferably performed by heating said liquid hydrocarbon fraction to a temperature in the range 300 to 600° C. such as heating to a temperature in the range 360 to 550° C. and preferably to a temperature in the range 400 to 525° C. such as in the range 420 to 500° C. at a pressure in the range 0.5 to 30 bar, thereby producing at least one upgraded liquid hydrocarbon fraction and at least one solid residue fraction and at least one gas fraction and at least one fraction comprising water.

The fraction comprising water is according to a preferred embodiment recycled to the fifth step of recovering such as by introducing it into and mixing it with the residual fraction from said fourth step of separating.

Said sixth step of upgrading by heating according to the present invention may comprise heating said liquid hydrocarbon fraction in an inline heater and subsequently separating it in a flash drum and/or in a fractionator.

During said heating of said sixth step of upgrading according to the present invention, volatiles are evaporated but a mild thermal cracking of the liquid hydrocarbon fraction also occurs. As it will become clear from the accompanying examples, it has been found that the upgrading by heating according to an advantageous embodiment of the present invention increases the calorific value of the liquid hydrocarbon product and/or reduces the viscosity of the liquid hydrocarbon product and/or reduces the density of the liquid hydrocarbon product and/or reduces the acid number, while keeping the amount of char or coke formed at manageable level. Hence, said upgrading step according to the present invention may comprise a visbreaking, delayed coking and/or thermal cracking process or a combination thereof.

The amount of coke being formed may according to the present invention be less than 30% of the mass of the carbon in the liquid hydrocarbon fraction such as less than 25%. Preferably the amount of coke being formed is less than 20% of the mass of carbon in the liquid hydrocarbon product such as less than 15% of the mass of carbon in the liquid hydrocarbon product.

On an energy basis the energy content of the coke being formed is less than 40% A) of the energy contained in said liquid hydrocarbon fraction such as less than 30% of the energy content of said liquid hydrocarbon fraction, and preferably less than 20% of the energy content in said liquid hydrocarbon fraction.

Embodiments of the present invention include upgrading a liquid hydrocarbon fraction comprising a relatively high amount water and ash. Such liquid hydrocarbon fractions may e.g. be derived from embodiments where a feedstock having a high a high ash content such as anaerobically digested sewage sludge is processed and no particle removal is performed during the second step of converting, and wherein said fourth step of separating is performed by a gravitational settling or sedimentation process.

In such applications the liquid hydrocarbon product may stick to the ash particles and make it difficult to separate efficiently without using very expensive separation techniques. Hence, in some embodiments of the present invention embodiment according to the present invention the liquid hydrocarbon fraction may comprise up to 35% ash and up to 35% water.

The sixth upgrading step according to the present invention solves this problem by fractionating both the ash and water from liquid hydrocarbon product. A preferred embodiment of said sixth upgrading includes heating in at least one vessel or drum. Further a preferred embodiment may include fractionating said liquid hydrocarbon in a fractionator located downstream to said heating as further illustrated and described in relation to the FIGS. 13-15.

The heating in said step of upgrading may be performed in at least 2 steps. Preferably the first step of heating comprises heating to a temperature of maximum 200° C., such as below 180° C., preferably the temperature in said first step is below 160° C., such as below 140° C. and even more preferably the temperature of said first step of heating is in the range 100 to 140° C. By dividing the heating into two steps and maintaining the temperature below temperatures specified above, it a selective vaporization of water with some lower boiling compounds from said liquid hydrocarbon fraction is obtained. Further the heat required for said heating and evaporation process may be performed using low quality heat.

A preferred embodiment of a process according to the present invention included a recovery from said third step of cooling and expanding for at least partly supplying the heat required for said first step of heating. The evaporated fraction comprising water with some organics is preferably recycled to said fifth step of recovering as described above.

The evaporated fraction may at least partly supply heat required in said recovering step.

A residual fraction comprising liquid hydrocarbons and solids is preferably withdrawn from said first step of heating and fed to a second step of heating wherein said fraction is heated to a temperature of up to 600 C, such as heating to a temperature in the range 400 to 550° C. The pressure in said second step of heating is according to a preferred embodiment of the invention preferably maintained in the range 2 to 10 bar in order to minimize the amount of coke formed during said second heating step.

The evaporated fraction in said second step of heating may be fed to a fractionator for further fractionation and separation into specific boiling point ranges.

Another advantageous embodiment of a process according to the present invention includes condensation of said evaporated fraction in two or more condensing steps having predefined decreasing temperature. Hereby a fractionation of said evaporated liquid hydrocarbon is obtained.

In a preferred embodiment the outlet temperature of the non-condensed liquid hydrocarbons from the first step of condensing is maintained in the range 330-380° C. as an outlet temperature of the non-condensed liquid hydrocarbons from the first step of condensing of 360° C.

Further in accordance with a preferred embodiment according to the present invention the outlet temperature from the second step of condensing is in the range 120 to 300° C. such as in range 150 to 250° C.

The fraction not condensed in said second step of heating typically comprises hydrogen, carbon monoxide, methane, ethane, propane and butanes, and have a relatively high calorific value. Preferably said gas is combusted to produce heat for heating in the process.

The heat of condensation in said steps of condensing is preferably transferred to a cooling medium. In a preferred embodiment according to the present invention the heat transferred to said cooling medium is used for at least partly supplying the heat required in said heating in the second step of converting.

The cooling medium may comprises hot oil such as Dowterm B or a molten salt such as a Hitech salt.

The cooling medium may subsequently be used to supply heat to the second step of converting be used for at least partly supplying the heat required in the sixth step of upgrading the liquid hydrocarbon fraction from the fourth step of separating.

Said at least partly supplying heat to the sixth step of upgrading the liquid hydrocarbon fraction, may according to a preferred embodiment be performed by heat exchanging said cooling medium with the liquid hydrocarbon fraction prior to and/or during said first heating of the sixth step of upgrading. Further said cooling medium is used to supply heat to said second step of heating e.g. by preheating the liquid hydrocarbon fraction withdrawn from the first step second step of heating before entering into the second step of heating or the liquid hydrocarbon fraction and/or by heating by heat exchange within vessel for said second step of heating.

The cooling medium may according to an embodiment of the present invention be heated in a burner or furnace prior said heating the second step of heating.

Solids such as ash and coke may, according to an advantageous embodiment of the present invention, be allowed to accumulate within the vessel for said second step of heating in a predefined period. In such embodiment, the process according to the present invention may comprise two or more vessels or drums for said second step of heating operating in a sequential cycle.

Figure 10:
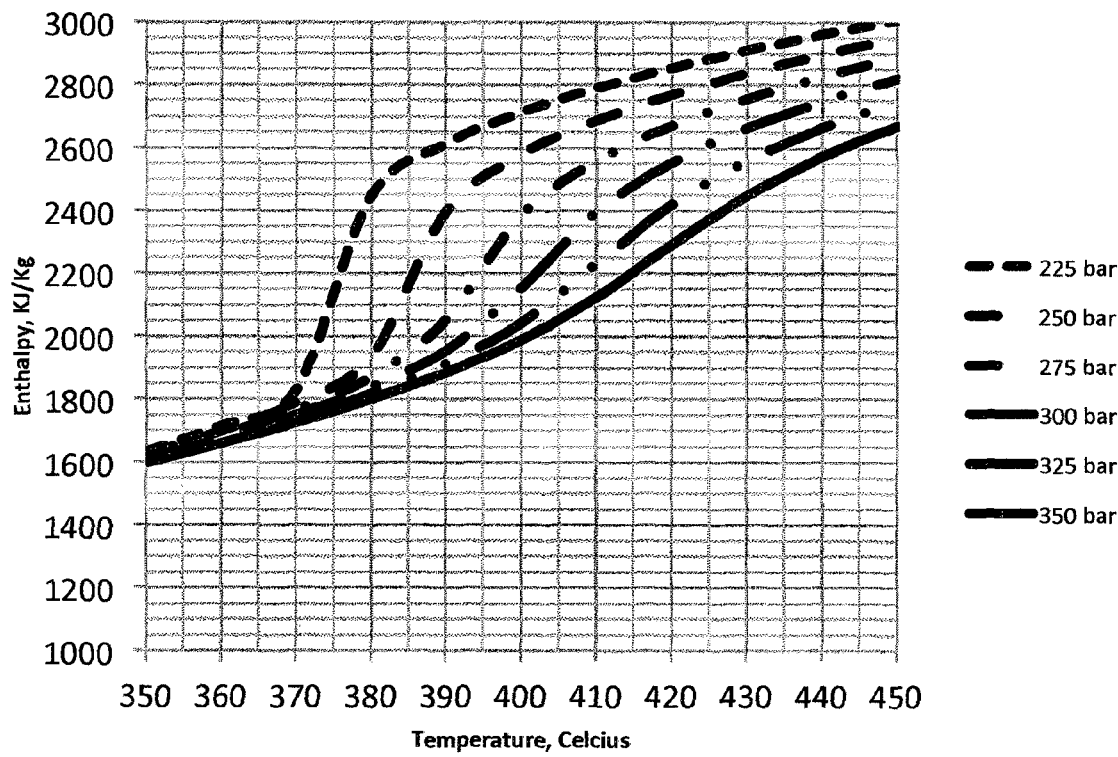
FIG. 10 shows a schematic diagram of the enthalpy of water as a function of temperature and pressure.

FIG. 10 shows an additional advantage of present invention. The operating pressure and temperature in the ranges of the present invention is important for obtaining the desired chemistry and yields of the process.

However, an additional advantage of operating at the pressures according to the present invention is illustrated in FIG. 10 for pure water. As seen from the figure, pressure has limited effect on the enthalpy at a given operating temperature up to a temperature of around the critical temperature of water 374° C., but above the critical temperature operating pressures becomes increasingly important for the enthalpy at a given temperature i.e. the energy input required to heat water to a specific temperature is lower at higher pressure. For instance, at an operating pressure of 300 bar and above, the energy input required at an operating temperature of 390° C. is approximately 30% less than at a pressure of 225 bar and 20% less than at 250 bar.

The actual feed mixture to be heated is not pure water and contains organics of various kinds. The presence of these organics can move critical temperature both up and down depending on the specific organics and carbonaceous material being converted. Hence, the figure is intended for illustrative purpose of added benefits of the operating conditions according to the present invention.

FIG. 11 shows a preferred embodiment of a continuous process according to the present invention.

Pretreatment

Carbonaceous material contained in one or more input streams A,B are introduced into a pretreatment step in pretreatment device 1, where they are transformed into a homogeneous, pumpable feed mixture in the form of a slurry and/or paste F. This may be preformed e.g. by introducing in situ produced liquid hydrocarbon compounds such as a recycle stream of the liquid hydrocarbon product produced or a fraction of the same as indicated by the fluid stream from the pipeline after the first separation and into the pretreatment device 1 and/or recovered liquid organic compounds and/or homogeneous catalysts from the water phase as indicated by the fluid stream from 14 into the pretreatment device 1. Depending on the concentration of the homogeneous catalysts such as potassium and/or sodium in the input stream-s) make up catalysts C may also be introduced to adjust the catalyst concentration to the concentration according to the present invention. Said catalyst may according to a preferred embodiment of the present invention be added as a salt or be dissolved in a liquid e.g. water. Often said make up catalyst(s) C according to the present invention will be in an alkaline form such as in an hydroxide or carbonate form, and may besides make up of the homogeneous catalyst concentration further serve as a pH adjustment of the feed mixture F so as to obtain a pH of at least 7 during or after said conversion, preferably a pH in the range 8-12 and more preferably a pH in the range 8-11. In many embodiments according to the present invention, the pH of the feed mixture during and/or after said conversion of carbonaceous material contained in said feed mixture F is controlled by measuring the pH during and/or after said conversion and adjusting the pH in said feed handling 1 by addition of make-up catalyst and/or alternatively adding another base D to said feed handling 1.

Typically the weight ratio of said recycled stream(-s) comprising liquid organic compounds relative to said input streams being introduced into said feed handling according to the present invention is in the range 0.01 to 5.0, such as in the range such as in the range 0.1 to 2.0, preferably in the range 0.15 to 1.0 such as in the range 0.10 to 0.5, and even more preferably in the range 0.2-0.4. Besides introducing process advantages from a conversion point of view, the recovery and recycle of in situ produced liquid organic compounds to the pretreatment 1 enables preparation of a feed mixture comprising homogeneous pumpable slurry or paste F from the input streams as received and/or preparation of a feed mixture comprising a pumpable slurry or paste F having a higher dry matter content as no or less water and/or other solvent needs to be added to said pretreatment 1. It has further been found that presence of said liquid organic compounds during said pretreatment 1 introduces a stabilizing and/or dissolution effect that assists in homogenizing the feed mixture F e.g. by decreasing the viscosity of said feed mixture at a given dry solid content and temperature or allows for operation a higher maximum particle size and/or at higher dry matter contents and thereby results in an overall more economical and effective process e.g. less parasitic energy losses and more oil produced.

The pretreatment 1 may according to a preferred embodiment of the present invention further comprise providing a feed mixture F with a maximum particle size of maximum of 30 mm such as a particle size of maximum 15 mm, preferably said feed mixture provided has a particle size of maximum 5 mm such as a particle size of maximum 2 mm, more preferably the maximum particle size in said feed mixture is in the range 0.01 to 1.5 mm such as 0.1 to 1.0 mm. Said providing may comprise controlling the maximum particle size particle size of the input materials e.g. by dividing said input materials A, B by a sieving operation and/or one or more crushing and/or grinding and/or milling and/or cutting operations (not shown) and/or by dividing said feed mixture F before being withdrawn from said pretreatment to the pressurization step.

The pretreatment 1 according to a preferred embodiment according to the present invention further comprises means for thoroughly mixing and transforming said input stream(s) and fluid streams A, B, C, D into a homogeneous slurry or paste. Said mixer may according to the present invention be a stirred vessel equipped with means for efficiently mixing and homogenizing viscous materials such as a planetary mixer, Kneader or Banbury mixer. Other preferred means for thoroughly mixing and homogenizing said input and fluid streams to a feed mixture according to the present invention include inline mixers. Such inline mixers may further introduce a cutting and/or scissoring and/or self-cleaning action. The mixer is preferably further equipped with means for heating said feed mixture to a temperature in the range 50 to 200° C., preferably in the range 80 to 180° C. and more preferably in the range 90 to 160° C. at sufficient pressure to avoid boiling such as a pressure in the range 1-20 bars, preferably in the range 1-12 bars. Preferred means for heating said feed mixture during the pretreatment according to the present invention include a heating jacket not shown). In a preferred embodiment the heat for preheating said feed mixture F in the pretreatment 1 is obtained from the cooling of the converted carbonaceous material comprising liquid hydrocarbon product e.g. by heat exchange with this process stream. Hereby the energy efficiency of the process may be further enhanced.

According a preferred embodiment of the present invention, the mixer may further be equipped with a re-circulation loop (not shown), where material is withdrawn from said mixer and at least partly re-circulated in an internal or external loop and re-introduced into said pretreatment so as to control the residence time in said pretreatment or feed handling to a predefined time. Preferred residence times in said pretreatment step 1 are according to the present invention in the range 1 minute to 24 hours such as in the range 5 minutes to 12 hours. Preferably the residence time is in the range 5 minutes to 6 hours, more preferably in the range 10 minutes to 3 hours.

Typically the dry matter content according to the present invention is in the range 20 to 70% by weight, preferably in the range 25 to 60% and more preferably in the range 30 to 50% by weight.

The process according to the present invention requires water to be present in said feed mixture. Typically the water content in said feed mixture is at least 30% by weight in the range 30 to 80% by weight and preferably in the range 30 to 70%

The mechanical and/or thermal and/or chemical pulping of the input materials obtained in said pretreatment 1 according to a preferred embodiment of the present invention enables the production of a homogeneous pumpable feed mixture F premixed with additives for performing a process according to the present invention and having a high dry matter content at a viscosity processable by a process according to the present invention. The feed mixture according to the present invention results in a more effective and economical process than in the prior art e.g. less parasitic energy losses and higher oil yields.

Conversion

The feed mixture F is being withdrawn from said feed handling 1 and transferred to the pressurization pump 2, preferably by a positive displacement pump such as an auger or lobe pump. According to the present invention said pressurization to the desired reaction pressure is essentially performed before heating from entry temperature from the pretreatment 1 to the reaction temperature is initiated. Preferred pumps for said pressurization according to the present invention include rotary lobe pumps in a series arrangement, single or double acting piston pumps, hose diaphragm piston pumps.

The pressurized feed mixture is subsequently heated to a reaction temperature in the range 370 to 450° C. such as in the range 380 to 430° C., preferably in the range 385 to 430° C. such as in the range 390 to 430° C., more preferred in the range 400 to 430° C. such as in the range 400 to 420° C.

According to a preferred embodiment of the present invention said heating is performed in one or more heat exchangers 3, 4, 5. Preferably said heating is at least partly performed by recovery of heat from one or more process streams. In the preferred embodiment shown in the figure, heat is recovered from the hot product stream, from the reactor 6 and transferred to the pressurized feed mixture by direct heat exchange in the first heat exchangers 3 and 4. Typically the feed mixture F is heated from entry temperature to a temperature in the 180-250° C. in the first heat exchanger 3, and to a temperature in the range 300-390° C. in the second heat exchanger 4. In an optional embodiment said heat recovery may be performed by indirect heat exchange with a heat transfer medium such as steam, hot oil or a molten salt. By said heat recovery it is obtained that the process becomes very energy efficient as most of the heat required is recovered.

The heat exchangers 3 and 4 may optionally be combined into one heat exchanger. However, as the properties of the feed mixture e.g. the viscosity changes significantly during said heating, it is typically preferred to divide said heating into two or more heat exchangers. This further has the advantage that different materials of construction may be used in the heat exchangers e.g. a lower alloyed material may be used in the first heat exchanger 3. Further according to a preferred embodiment of the present invention said heat exchangers are designed to provide a relatively high heating rate in the temperature range up to 300° C. or thereabout. Typically the heating rate in the to range from 140 to 300° C. is at least 50° C./min, preferably 75° C./min, more preferred 100° C./min and even more preferred 150° C./min. In combination with the characteristics of the feed mixture according to the present invention it is hereby obtained that undesired side reactions to char and tar is minimized, and that the yield of desired liquid hydrocarbon product is maximized.

The feed mixture F is further heated to reaction temperature in the heat exchanger 5. Said heater may be a fired heater 7 as shown in the figure e.g. a heater fueled by e.g. natural gas, oil or other suitable fuel 8. Preferably said fired heater is at least partly fueled by a product produced by the process according to the present invention such as gas produced by the process as shown in the figure. Other potential products produced by the process for at least partly fueling said fired heater may include char and liquid hydrocarbon product. By at least partly fueling said fired heater by a product produced the parasitic energy loss is reduced and the energy efficiency is increased. Hereby a process that uses less consumables, are more economical more energy efficient and having a smaller environmental and/or $CO_2$ footprint is obtained.

Alternative embodiments of the further heating to the reaction temperature according to the present invention include a fired heater with indirect heating e.g. where heat from the combustion fuel(-s) in said furnace or burner is first transferred to another heat transfer medium such as steam, hot oil or molten salt before heat exchange with said partly heated feed stream.

Subsequent to heating to reaction temperature said pressurized and heated feed mixture F is maintained at the desired pressure and temperature in a reaction zone 6 for a predefined time. The feed characteristics and/or the combination of pressure and temperature according to the present invention generally allow for shorter reaction times and/or a more reacted liquid hydrocarbon product than in the prior art without sacrificing the yield and/or quality of the desired product. The predefined time in said reaction zone may according to an embodiment of the present invention be in the range 1 to 60 minutes such as 5 to 45 minutes, preferably said predefined time in said reaction zone is in the range 10 to 40 minutes such as in the range 10 to 30 minutes, more preferred in the range 10 to 25 minutes such as 10 to 20 minutes.

A reaction zone 6 according to the present invention advantageously comprises one or more reactors, preferably vertically oriented, wherein said feed mixture is fed to the top of said reactor(-s) in same direction as the gravity and withdrawn from the bottom. Preferably said conversion reactors further comprise a conically shaped inlet for introducing said feed mixture in the top and a conically shaped outlet for withdrawing said converted feed mixture F in the bottom. Advantageously said conically shaped inlet has an angle of the walls of said conically shaped inlet to the centerline of said reactor below 60°, and said conically shaped outlet has an angle of the walls of said conically shaped outlet to the centerline of said reactor below 30°.

Further the diameter of inlet and outlet of reactor 6 to the maximum diameter of the reactor are preferably selected so as to obtain a minimum ratio of the maximum average velocity in inlet/outlet to the minimum average velocity in the reactor of at least 4, preferably the ratio of the maximum average velocity in the inlet/outlet to the minimum average velocity in the reactor are selected so as to obtain a ratio of velocities at least 16, more preferred the maximum average velocity in the inlet/outlet to the minimum average velocity in the reactor are selected so as to obtain a velocity ratio of at least 25 such as a at velocity ratio of at least 50.

Hereby an advantageous reactor system is provided that is less sensitive to clogging due to sedimentation of suspended particles, and is more compact and economically attractive than in the prior art. Further the controlled decrease and increase of velocities in the inlet and outlet may allow for a more efficient use of the reactor volume.

Cooling and Expanding

The outlet stream from the reactor 6 comprising liquid hydrocarbon product from said converted carbonaceous material is subsequently cooled by heat exchange with the incoming feed mixture F in the heat exchangers 3,4. Often it is cooled to a temperature in the range 240-300° C. in the heat exchanger 4 and further to a temperature in the range 100-200° C. in the heat exchanger 3 and optionally by heat exchange in said pretreatment/or feed handling step as described above, before expanding the converted feed mixture containing liquid hydrocarbon product to a pressure in the range 1-70 bars in one or more expansion steps 9. A further cooler 10 may be provided.

Separation

The mixture from said expanding containing liquid hydrocarbon product is subsequently lead to separation. Said separation may according to the present invention comprise means 11 for separating gas from said mixture as shown in the figure. Said separation means may comprise a flash separator or degasser 11, wherein gas is withdrawn from the top. According to an embodiment of the present invention said gas may be used to produce heat for heating in the process to the process as shown in the figure and further described above. The gas may optionally be cooled to condense compounds such as e.g. water prior to said use to produce heat for heating in the process.

The gas separating means 11 may further provide at least a coarse separation of the degassed mixture into a liquid hydrocarbon rich stream and residual water rich stream e.g. by gravimetric separation. The water rich stream comprising water soluble organics, suspended particles and dissolved salts may be at least partly withdrawn from said gravimetric separator, and fed to a recovery unit, optionally after further separation by filtering and/or centrifugation (not shown) to remove suspended particles.

The degassed mixture or optionally the liquid hydrocarbon rich stream, is withdrawn from said gas separating means 11, and may be further separated by centrifugation 12,13. Said centrifugation 12,13 preferably comprises one or more 3-phase centrifuges such as one or more high speed disc bowl centrifuges and/or one or more decanter centrifuges 12,13, separating the degassed mixture into a water phase containing water soluble organics and dissolved salts, an oil phase and a sludge phase comprising suspended particles. The first centrifuge 12 is preferably a concentrator designed for producing a water phase substantially free of liquid hydrocarbon product, a liquid hydrocarbon product comprising some water and a sludge phase comprising suspended ash and/or char particles. The water phase is fed to the recovery unit 14. The liquid hydrocarbon product is fed to the second centrifuge 13 for further separation of water and ash and/or char. Preferably the liquid hydrocarbon product after said first centrifuge is being divided prior to entering said second centrifuge 13. Preferably a fraction of said liquid hydrocarbon product produced is recycled to said pretreatment step 1.

The second centrifuge 13 is preferably a high speed disc bowl centrifuge designed as an oil purifier i.e. to produce an liquid hydrocarbon product substantially free of water. Water from the second centrifuge 13 is preferably mixed with water from the first centrifuge 12 and fed to the recovery unit 14. Similarly ash and/or char from the second centrifuge 13 is mixed with ash and/or char from the first centrifugation 12, dried (not shown) and send to storage.

For effective separation the centrifuges 12,13 according to an embodiment of the present invention is preferably operated at temperature in the range 50 to 200° C. such as a temperature in the range 70 to 150° C. The pressure during said separation by centrifugation is maintained at a pressure sufficiently high to avoid boiling at the prevailing temperature e.g. a pressure of up to 15 bar, preferably a pressure up to 10 bar, more preferred a pressure up to 5 bar.

Recovery

The water phases from the gas separating means 11, centrifuges 12 and 13 are fed to a recovery device 14, where liquid organic compounds and/or homogeneous catalysts are recovered in a concentrated form, and recycled to into the pretreatment device 1.

Preferably said recovery device 14, comprises an evaporation step, wherein said water is evaporated from said combined water phases, and thereby providing a distillate and a concentrate. The combined water phases may be preheated to a temperature of e.g. 70-95° C. before entering into said evaporator. The heat for said preheating is preferably provided by heat recovery from a process stream and/or from the outgoing distillate stream before entering into the evaporator.

In the evaporator, water is evaporated from said mixture comprising water soluble organics and dissolved salts at a temperature of 100 to 105° C. A preferred embodiment of said evaporator according to the present invention include increasing the condensation temperature of said evaporated water by increasing the pressure by a blower, compressor (Mechanical Vapor Recompression) or a steam jet ejector (Thermal Vapor Recompression) or a combination thereof. Thereby the evaporated water vapor can be used as a heating medium for the evaporation in said evaporator, and said evaporator becomes very energy efficient as the latent heat of evaporation do not need to be supplied to said evaporation step. Preferably said evaporated fraction passes a demister and/or foam breaker prior to said vapor recompression. Said evaporator may advantageously be divided into two or more steps operating at a decreasing pressure and temperature each heated with the evaporated vapor from the same vapor (in the case of vapor recompression) or the vapor from the foregoing step to minimize or further minimize the heat required for said evaporation.

Said evaporator may further comprise condensing said evaporated vapor in to or condensation steps, where the condensation temperatures in said condensation steps are selected so as to obtain a fractionation of the evaporated fraction i.e. a fraction comprising water and eventually higher boiling compounds, and a fraction where compounds having a boiling point temperature lower than water are concentrated. It should be noted that said condensers according to the present invention may comprise heat exchangers where the media to be concentrated are evaporated on the other side, but in general said evaporation step according to the present invention comprises at least one additional condenser compared to the number of evaporation steps.

The fraction comprising evaporated water ("distillate") may further be cooled to a temperature suitable for discharge in a cooler, 15. Hereby, it is obtained that said evaporator besides recovering said liquid organic compounds and/or homogenous catalysts also cleans and purifies the water phase in an efficient manner, and can produces a water phase that may be reused or discharged to recipient. Optionally the "distillate" may be subjected to one or more polishing steps, 16. Said polishing steps may include an absorber and/or adsorber and/or a coalescing step and/or membrane system and/or a biological treatment system such as bioreactor.

The fraction being concentrated with compounds having a boiling point lower than water may according to a preferred embodiment be mixed with the concentrate from said evaporator, and recycled to the pretreatment step 1.

Figure 11A:
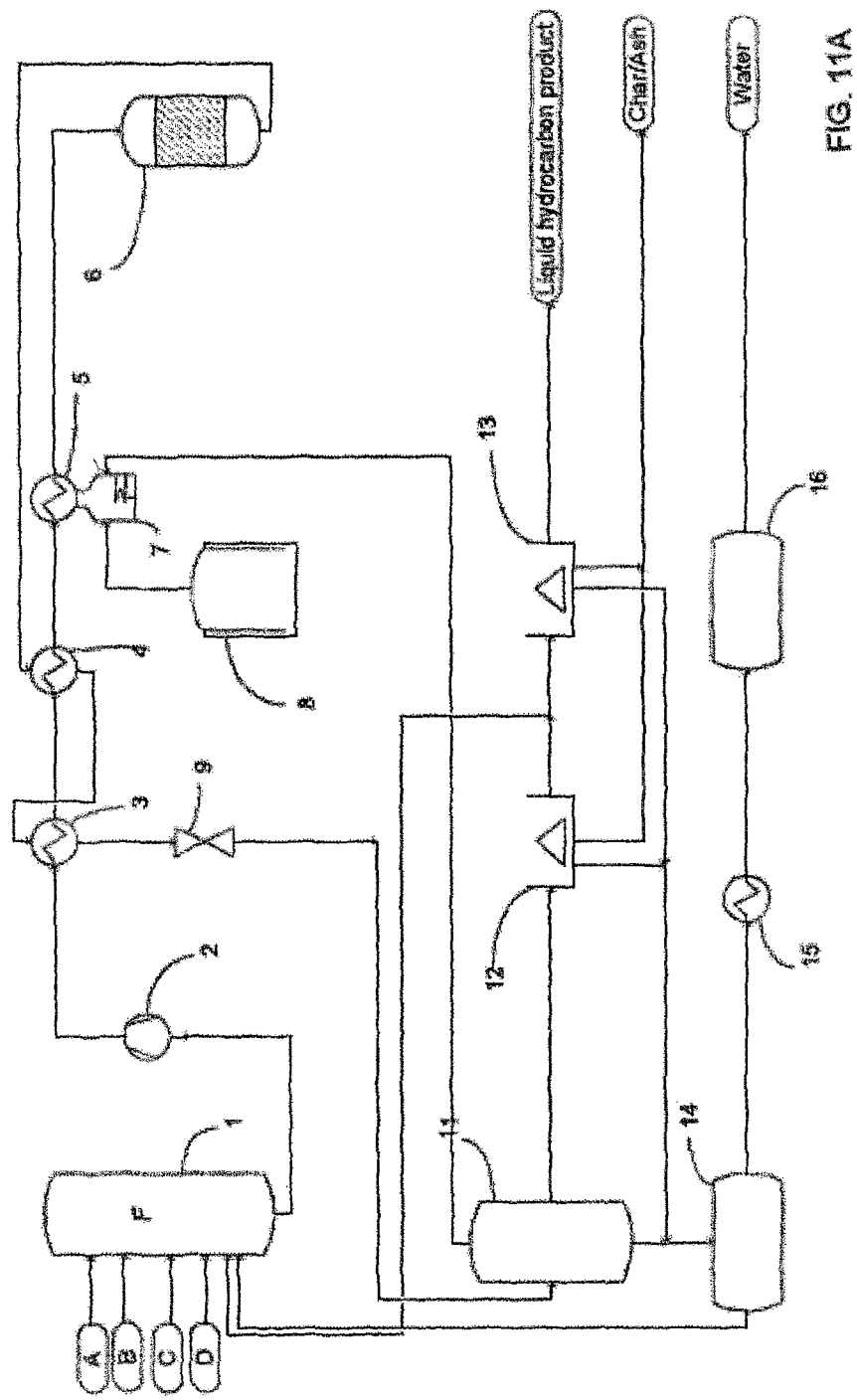
FIG. 11A shows a diagram of a preferred embodiment of a process apparatus according to the invention.
Figure 11B:
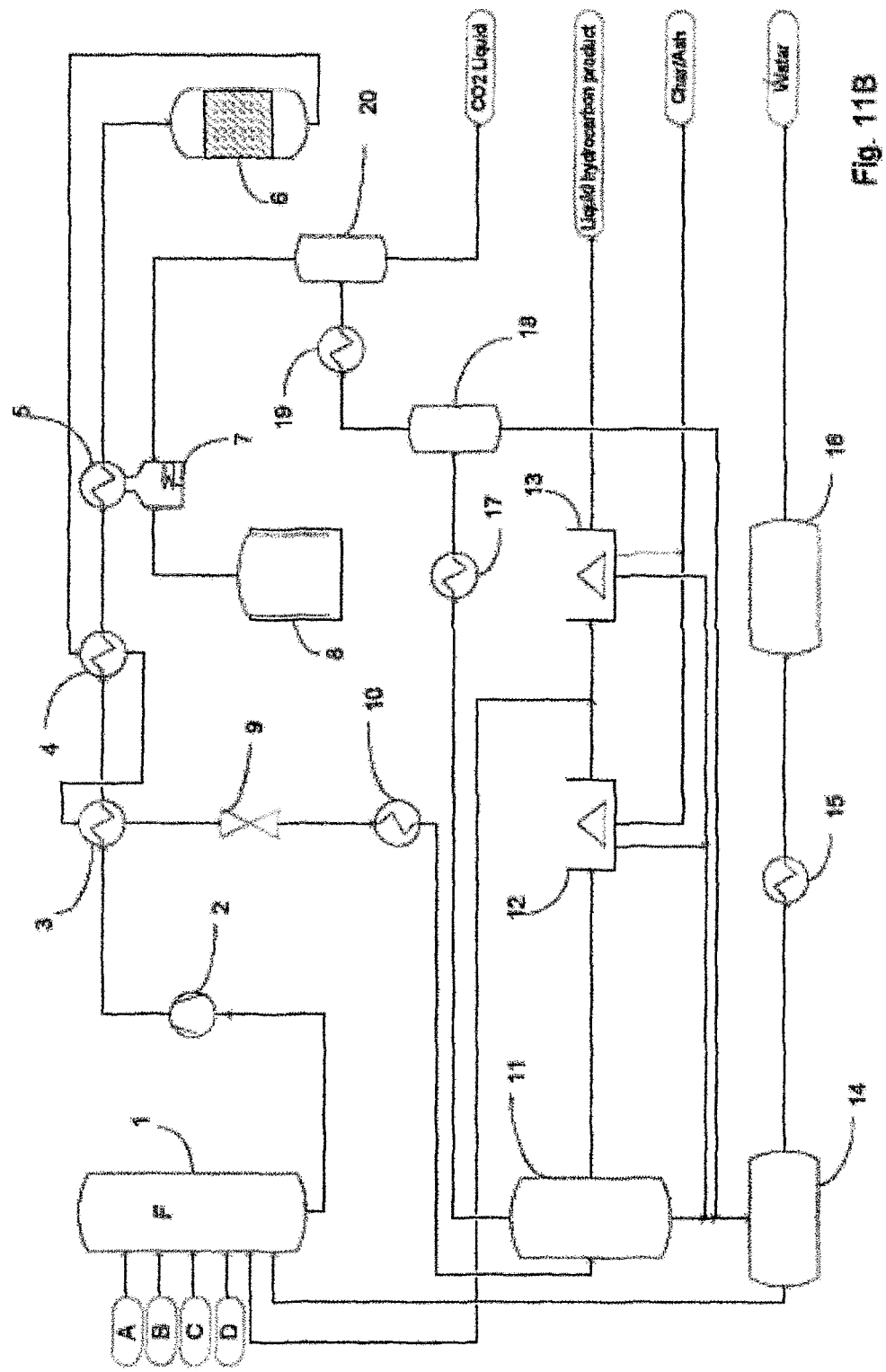
FIG. 11B shows a diagram of a preferred embodiment of a process apparatus including CO2 removal according to the invention.

FIG. 11B shows a preferred embodiment of a process according to the present invention, wherein $CO_2$ is recovered from the gas produced by the process.

A carbonaceous material from one or more feedstock is provided as a feed mixture according to the present invention and converted into a liquid hydrocarbon product in a continuous process by pressurizing the feed mixture to a pressure in the range 50-400 bar, and subsequently heating the feed mixture to a temperature in the range 250 to 500° C., and maintaining the feed mixture in the desired pressure and temperature range in a reaction zone for a predefined time. Subsequently the mixture containing converted carbonaceous material, is cooled and expanded in one or more cooling and expansion steps to a temperature in the range 25-200° C., and a pressure in the range 1 to 70 bar.

The converted feed mixture is at least partly expanded in at least one flash separation step 11, wherein the converted feed mixture is separated into a gas phase and a liquid phase. The gas typically contains 60 to 95+% $CO_2$ by weight with the remainder being hydrogen, $C_1$-$C_4$ hydrocarbons and water. The gas is is withdrawn from the top of the flash separator, and $CO_2$ is recovered from said gas phase.

It should be understood that the cooling and expanding may comprise a series of flash separators operating at different pressures and temperatures e.g. a first flash separator may be operating at a temperature and pressure close to the reaction temperature and pressure and may result in a gas phase and liquid phase. Either phase may be further cooled, expanded and separated into further gas and liquid phases. According to an embodiment of the present invention $CO_2$ is recovered from said gas phase or combination of gases by cooling and expanding said gas phase under pressure to a final pressure below the critical pressure of $CO_2$ of 74 bar such as a pressure in the in the range 50 to 70 bar, and a final temperature below the critical temperature of $CO_2$ of 31° C. in one or more steps so as to condense and recover $CO_2$ as liquid $CO_2$.

The process for recovering $CO_2$ is exemplified in FIG. 11B based on the preferred embodiment of a process as was illustrated in FIG. 11A.

As shown in the FIG. 11B a preferred embodiment includes a flash separator or degasser 11 that separates said converted feed mixture into a gas phase comprising a substantial amount of $CO_2$ and a liquid phase. The flash separator or degasser is preferably operated at a pressure of 50-70 bar and a temperature in the range 100 to 200° C. The gas may withdrawn from the top and cooled to a temperature in the range 35 to 80° C. such as a temperature in the range 35 to 50° C. in a first condenser 17, whereby a first condensate comprising water and/or other condensables such as methanol, ethanol and/or acetone are produced. The condensate is separated from the gas in the splitter 18, and preferably fed to the recovery unit for concentration and purification. The gas phase separated from said splitter 18, is further cooled to a temperature below the critical point of $CO_2$ of 31° C. in the second condenser 19. Preferably said gas exiting the first splitter is cooled to a temperature in the range 12-30° C. such as a temperature in the range 15-25° C., whereby $CO_2$ is condensed. $CO_2$ condensed by the cooling in the second condenser is separated from the residual gas in the second splitter 20. The liquid $CO_2$ recovered is fed to a storage tank. The liquid $CO_2$ produced may be used for production of algae as described in FIG. 11A or enhanced oil recovery etc. The residual gas may have a high calorific value and a high hydrogen content after said separation. According to the present invention, the calorific value of said residual gas may be above 20 MJ/kg such as above 25 MJ/kg, preferably said residual gas may have a calorific value above 30 MJ/kg such as above 35 MJ/kg, more preferred said gas may have a calorific value above 40 MJ/kg. The residual gas produced may according to the present invention be used for at least partly producing heat for heating of the process such as shown in FIG. 11A.

The hydrogen concentration in said residual gas may be more than 30% by volume such as a hydrogen concentration of more than 35% by volume, preferably the hydrogen concentration in said residual gas is above 40% by volume. The hydrogen rich residual gas may in another embodiment according to the present invention be used as a hydrogen source in an upgrading process for upgrading said liquid hydrocarbon as further described in relation to the following figures.

Figure 12:
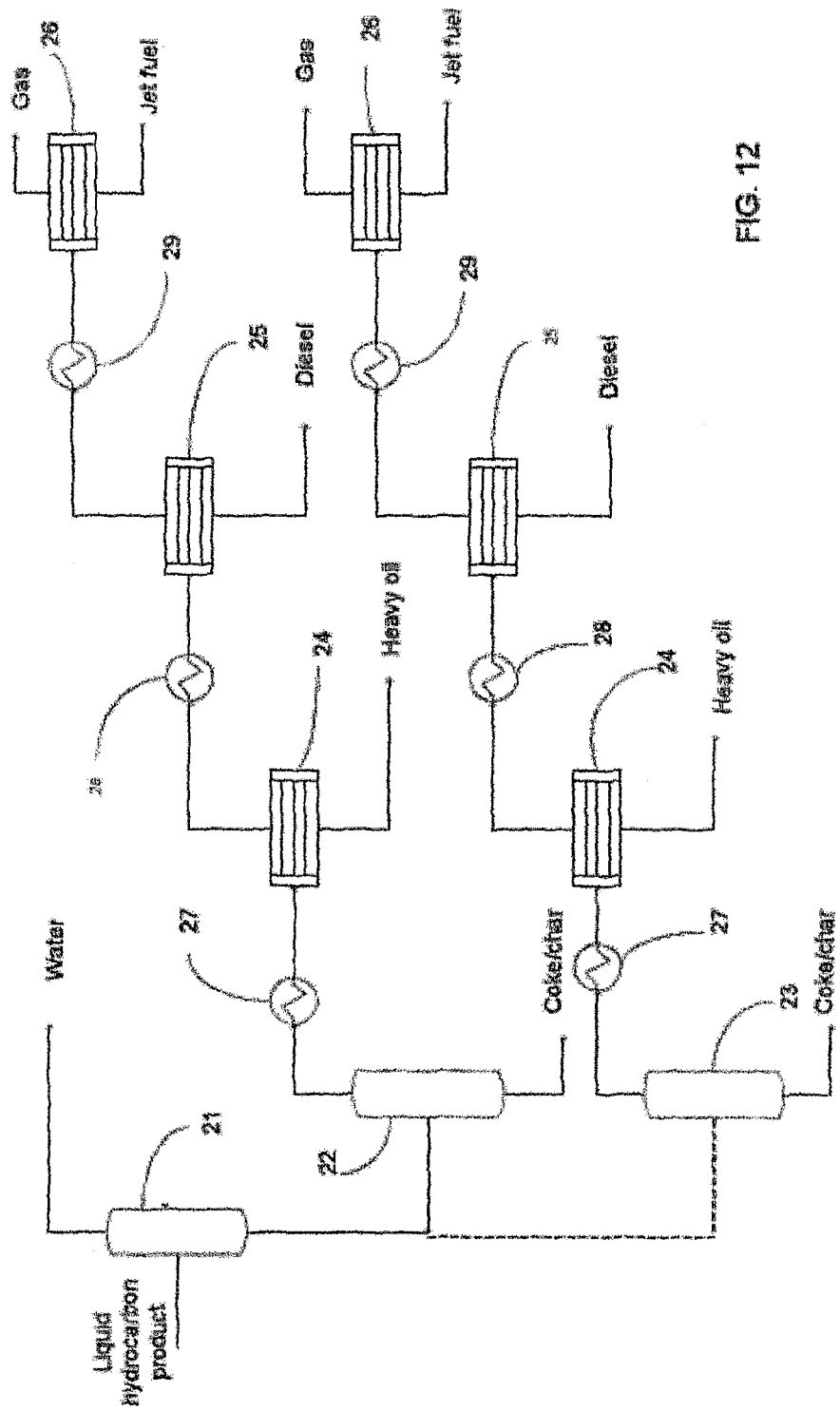
FIG. 12 shows a diagram depicting a preferred embodiment of a device for upgrading hydrocarbon products.

A preferred embodiment of an upgrading process according to the present invention is shown in FIG. 12.

The liquid hydrocarbon product after said separation according to the present invention is a crude product, which may be of sufficient quality for direct use in e.g. combustion applications or for further upgrading in a centralized refinery.

However, in many applications according to the present invention it is desirable to further upgrade the liquid hydrocarbon product to broaden the direct application window and/or to provide more higher value applications for the product.

FIG. 12 shows a preferred embodiment for upgrading the liquid hydrocarbon product according to an embodiment of the present invention, where the raw liquid hydrocarbon product from said separation is heated to a temperature in the range 300 to 600° C. such as in the range 360 to 550° C., preferably to a temperature in the range 400 to 525° C., such as in the range 420 to 480° C. at a pressure in the range 0.5 to 30 bar, thereby producing at least one liquid hydrocarbon fraction and/or at least one solid residue fraction and/or at least one aqueous fraction.

The heating in said upgrading process may be performed in two steps as shown in FIG. 12. The raw liquid hydrocarbon product from said separation, first enters a first heating and separation step 21, where it is preheated and/or heated to a temperature up to 200° C., preferably below 180° C., more preferably below 160° C., more preferably below 140° C. and even more preferably in the range 100 to 140° C.

The heat for said first preheating and/or heating step is according to an embodiment of the present invention recovered from said cooling and expanding the feed mixture.

During said first heating step in the evaporator 21, water is evaporated from said liquid hydrocarbon product. Said evaporated water is preferably recycled to the recovery step and mixed with the residual fraction from said separation.

The residual fraction is withdrawn from said first heating step, and heated to a temperature of up to 600° C., preferably to a temperature in the range 400 to 550° C. and more preferably 425 to 500° C. in a second heating step in an evaporator 22. Hereby liquid hydrocarbons are evaporated leaving a residual solid fraction of char/coke, heavy residues and ash in said second heater/evaporator 22. Said solid fraction is allowed to accumulate in the second heater for e.g. 24 hours, whereafter the feed of liquid hydrocarbons is fed to the other second heater 23. The evaporated liquid hydrocarbons are condensed in two or more condensers 24,27;25,28;26,29 having decreasing and predefined condensation temperatures, whereby a fractionation of said hydrocarbons occurs. The outlet temperature of the non-condensed liquid hydrocarbons in said first condensation step may in a preferred embodiment be in the range 340 to 400° C., preferably in the range 350 to 390° C., more preferably in the range 360 to 380° C., whereby a liquid hydrocarbon fraction comprising heavy gas oil is condensed. Further the outlet temperature of the non-condensed liquid hydrocarbons in said second condensation step is preferably in the range 230 to 250° C., whereby a fraction comprising liquid hydrocarbons having a boiling point in the diesel range is condensed. The outlet temperature of the non-condensed liquid hydrocarbons in said third condensation step is preferably in the range 100 to 150° C., whereby a fraction comprising liquid hydrocarbons having a boiling point in the jet fuel range is condensed. The a fraction not being condensed in said condensing steps comprises a combustible gas comprising hydrogen and may be combusted to produce heat for heating in the process. Optionally said combustible gas comprising hydrogen may be at least partly recycled to said second heating step (not shown in the figure). In an alternative embodiment said gas may be at least partly mixed with the residual gas described as described in connection with FIG. 11 or another hydrogen containing gas. By introducing and/or recycling said hydrogen containing gas to said second heating step less char and/or more liquid hydrocarbons and/or a less oxygenated liquid hydrocarbon product are produced in said second heating step.

The upgrading of said liquid hydrocarbon product by said heating steps according to the present invention results in a liquid hydrocarbon product having a higher quality and value, e.g. the upgraded liquid hydrocarbon product may be less viscous and/or have a lower density and/or has a lower acid number and/or having a lower oxygen content and/or have a lower Conradson carbon residue number and/or contain less ash and/or contains less water and/or has a higher calorific value than said liquid hydrocarbon crude product entering said upgrading process. Further said cooling and condensation with decreasing and predefined condensation temperatures results in a fractionation of said liquid hydrocarbon product into jetfuel, diesel and heavy fuel oil.

Figure 13:
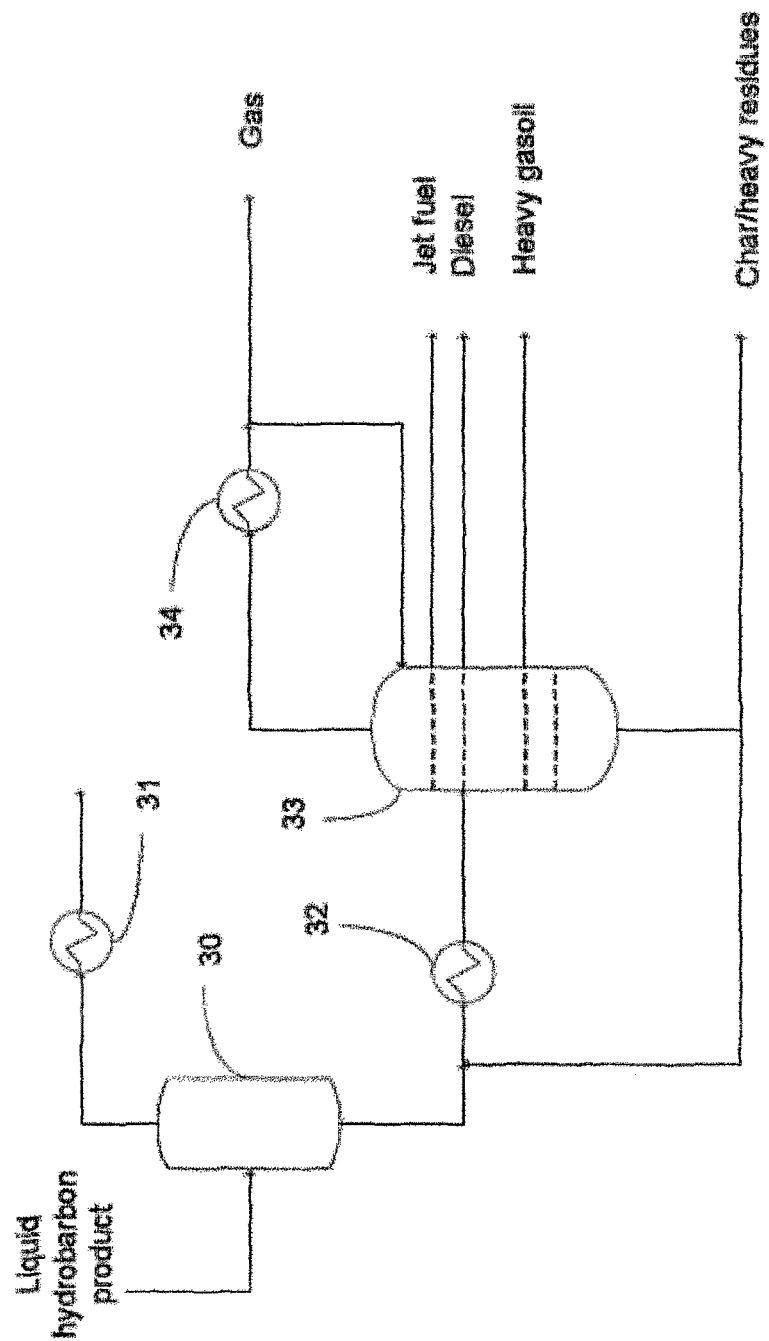
FIG. 13 shows a diagram depicting a preferred embodiment of a device for upgrading hydrocarbon products.

Another preferred embodiment of an upgrading process according to the present invention is shown in FIG. 13.

FIG. 13 shows another preferred embodiment of an upgrading process according to the present invention. The upgrading process is quite similar to the upgrading process illustrated in FIG. 12, but a fractionator 33 is used instead of the cooling and condensation with decreasing and predefined condensation temperatures.

The raw liquid hydrocarbon product from said separation, first enters a first heating and separation step in the evaporator 30, where it is preheated and/or heated to a temperature up to 200° C., preferably below 180° C., more preferably below 160° C., more preferably below 140° C. and even more preferably in the range 100 to 140° C.

Water is evaporated from said liquid hydrocarbon product in said first heating and separation step. The residual liquid hydrocarbon product exiting may be mixed with a stream recycled of, liquid hydrocarbon product from the bottom section of said fractionator 33 and heated to a temperature of up to 600° C., preferably to a temperature in the range 400 to 500° C. and more preferably to a temperature in the range 425 to 500° C. in a heater 32, whereafter it is introduced into the bottom part of the fractionator 33.

In the fractionator 33 the liquid hydrocarbon product is fractionated into a raw gas oil product and/or a raw diesel product and/or a jet fuel product. A stream of combustible gas comprising hydrogen is withdrawn from the top after cooling in cooler 34 and recycled as a condensate to the fractionator. Said gas may be mixed with the residual gas described in FIG. 11A-B and combusted to produce heat for process heating or may be recycled to said fractionator 33 or the hydroprocessing step described in relation to FIG. 14. A stream comprising heavy residues and/or coke and/or ash is withdrawn from the bottom of the fractionator 33.

Figure 14:
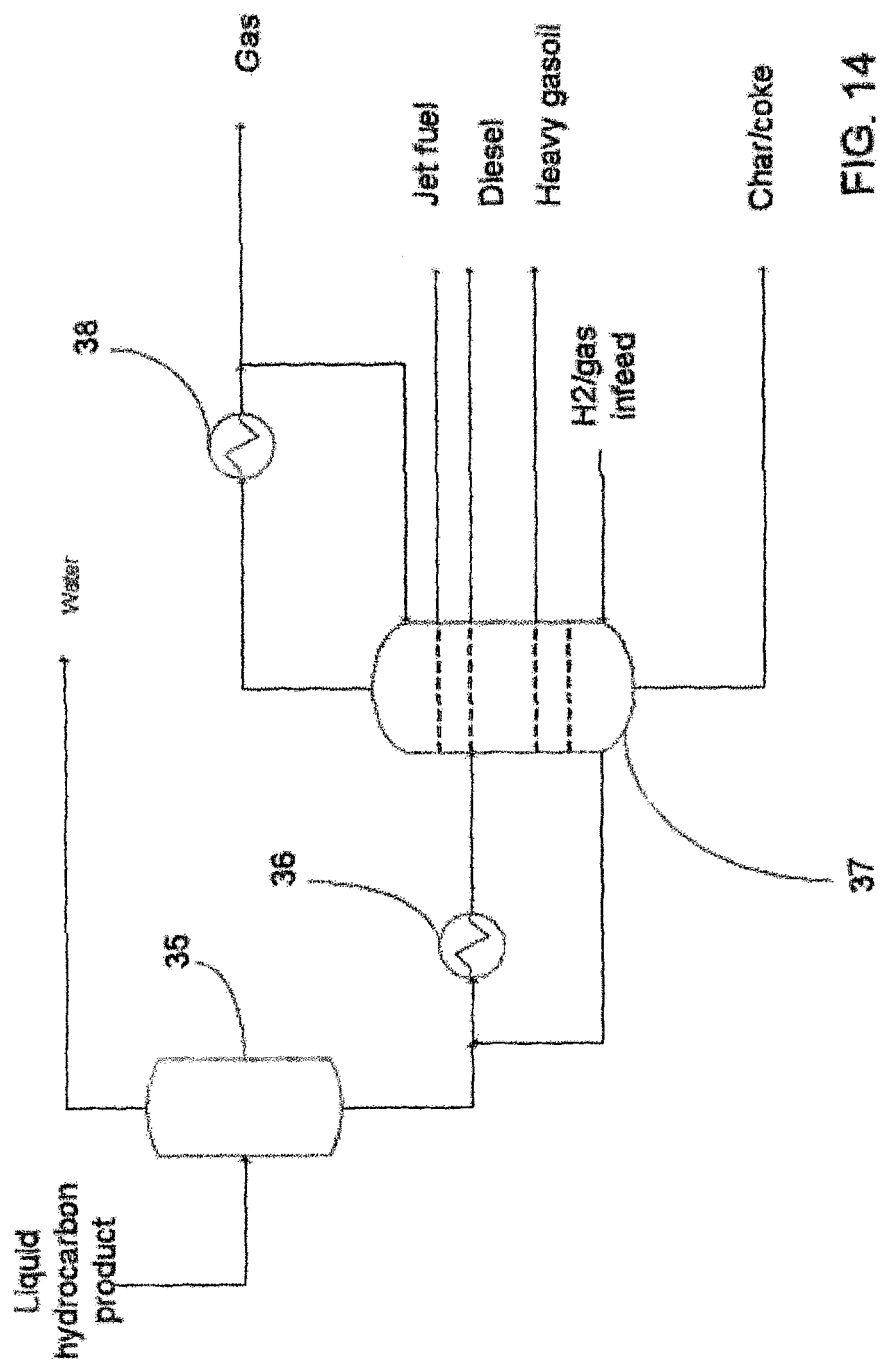
FIG. 14 shows a diagram depicting a preferred embodiment of a device for upgrading hydrocarbon products.
Figure 15:
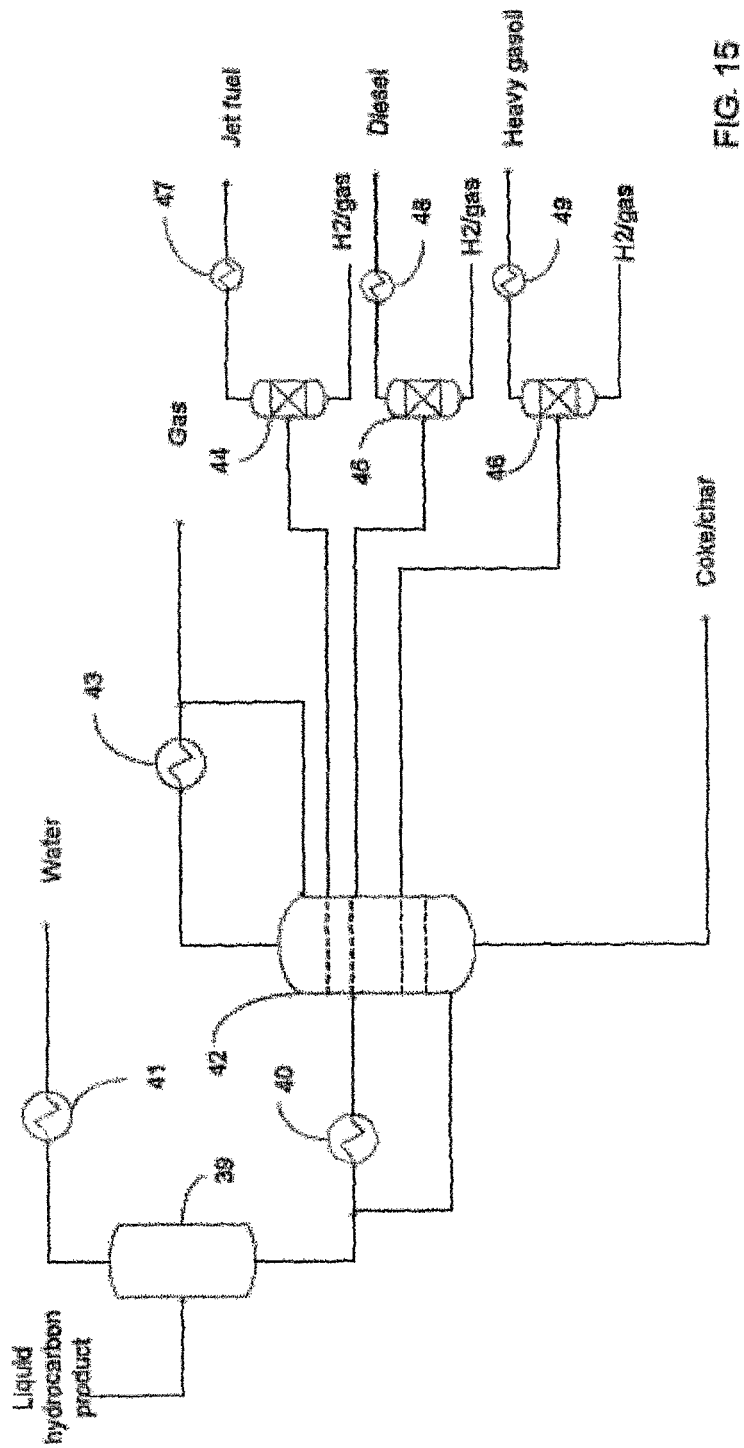
FIG. 15 shows a diagram depicting a preferred embodiment of a device for upgrading hydrocarbon products.

A further preferred embodiment of a process for production of finished liquid hydrocarbon is shown in FIGS. 14 and 15.

FIGS. 14 and 15 shows two embodiments of a process according to the present invention similar to FIG. 13, but further comprising steps for hydrogenation or hydroprocessing of said raw gas oil and/or raw diesel and/or jet fuel fractions from the fractionator to finished gas oil and/or diesel and/or jet fuel products. By said hydroprocessing residual oxygen, nitrogen or sulfur is removed.

Said hydroprocessing according to an embodiment of the present invention may involve the treatment of said liquid hydrocarbons with hydrogen in the fractionator 37 or in one or more catalyst beds 44,45,46 comprising a catalyst selected from CoMo, NiMo, NiW, Pd and Pt on a carrier of γ-alumina, aluminosilicates or zeolites (X, Y or mordenite) at a temperature in the range 300 to 430° C. and a pressure of 40 to 200 bar, preferably at a temperature of 350-400° C. and pressure of 60-120 bar and a liquid hourly space velocity of 0.5 to 5 hr. A successive cooling in coolers 47,48,49 takes place.

The source of hydrogen for said hydrotreatment may at least partly be the residual gas described in FIG. 11 or the hydrogen containing gas from said fractionator. Other hydrogen sources according to the present invention includes hydrogen produced by steam reforming of natural gas, hydrogen produced by electrolysis and hydrogen produced by gasification of char and/or coke produced by the process.

Though it is difficult to discriminate the influence of the individual parameters, the following factors are is believed to at least partly produce the advantages enjoyed by the invention:

High pressure generally suppresses the formation of char and tar. Further the pressure is important for overall reactivity and process stability i.e. if pressure is lost or not maintained e.g. due to pump failure or a relief valve that opens will result in spontaneous cooking and coking at the operating temperatures according to the present invention, thereby leading to clogging, plugging etc.

Furthermore, high pressures results in energy efficiency advantages above the critical temperature as described in relation to FIG. 10

The temperature according to the present invention ensures that the conversion proceeds sufficiently fast and is further important to the quality of the produced liquid hydrocarbons.

Besides assisting in the dissolution/conversion of the carbonaceous material the liquid organics are believed to work as radical scavengers suppressing the formation of char and tar and as hydrogen donors favouring deoxygenation by hydrogenation thereby resulting in an improved liquid hydrocarbon product yield and quality, besides preventing process upsets.

The homogeneous catalyst, in the form of potassium, suppresses tar and char formation and accelerates the reactions for the desired reactions paths, i.e. improves liquid hydrocarbon yield and quality.

Operating at pH>7 is important for reaction chemistry and reduces corrosion compared to operation under acidic conditions.

Liquid hydrocarbons produced in the process improves process economy significantly Water soluble organics are preferably part of the liquid organics being added. These can normally cause a process and energy loss, resulting in reduced yields of liquid hydrocarbons, and generating a waste stream that requires clean up (water phase is black!). The removal of organics from the water phase and recycle to the pre-treatment step increase the hydrocarbon yield, energy efficiency and improves economy of the process i.e. say that the distribution of the energy in the input stream is 75% to hydrocarbons, 20% to water soluble organics and 5% to gas without the recovery and recycle then the hydro carbon yield will increase to approximately: 75+75/80*0.2=93.75%

Besides the increased efficiency and selectivity improved processability e.g. a more fluidic is also obtained by said addition.

It should be noticed that the amount of recycled liquid organics will be in the range 2-5 wt % and this is not enough to obtain the minimum 5 wt % liquid organics in the preferred version therefore recycling of at least a fraction of the oil (preferred) or addition of other organics is required to obtain this level.

Recovery and recycle of at least part of the homogeneous catalyst improves process economy significantly.

Figure 16:
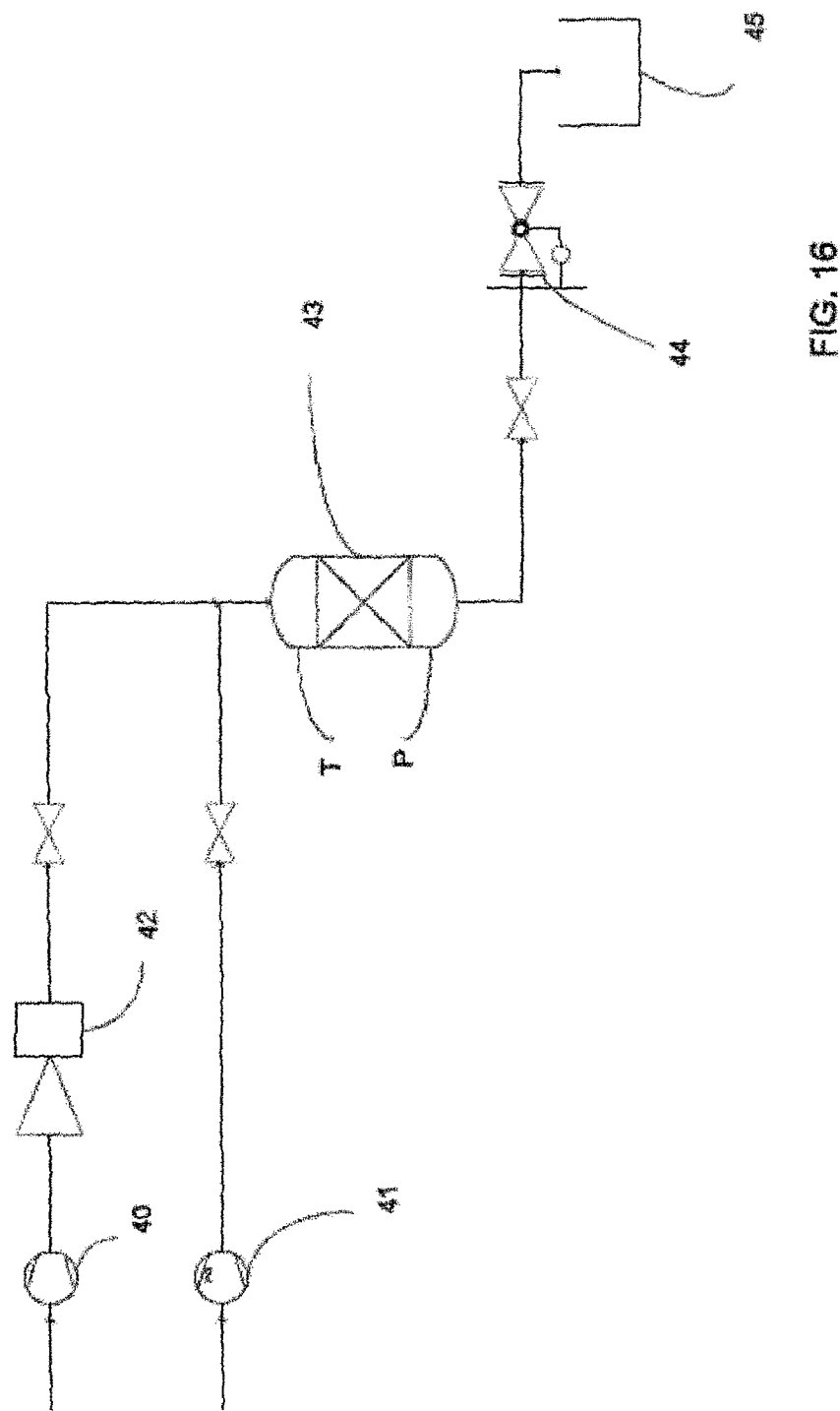
FIG. 16 shows a schematic drawing of an experimental set up used for experiments.

FIG. 16 is a schematic drawing of an experimental reactor set up used for conducting the experiment described in the examples 2 to 4. The reactor set is a so-called "stop flow" reactor, system allowing for injection of a feed mixture sample into a pre-heated and optionally pre-pressurized reaction chamber, where it can be maintained for a pre-defined time until the reaction is quenched.

The reactor, 4, is pre-heated to the desired reaction temperature by electrical heating elements, whereafter deionized water is pumped to the reactor by the pump 2. The pressure in the reactor is controlled by the back pressure valve, 5, which is also used for the expansion. After the pressure and temperature in the reactor has reached it set points, feed mixture contained in the injector 3 is fed to the reactor 4, by starting the metering pump 1 with a controlled speed. Typically said injection of feed material is continued until the reactor volume has been replaced 3-5 times. Here after the injection of the feed mixture is stopped. The feed mixture is maintained in the reactor for the desired reaction time, whereafter the reaction is quenched either by cooling and depressurizing, og by feed a controlled amount of deionized water to the reactor and withdrawing the diluted converted feed mixture via the control valve 5 into a sample container 6.

Figure 17:
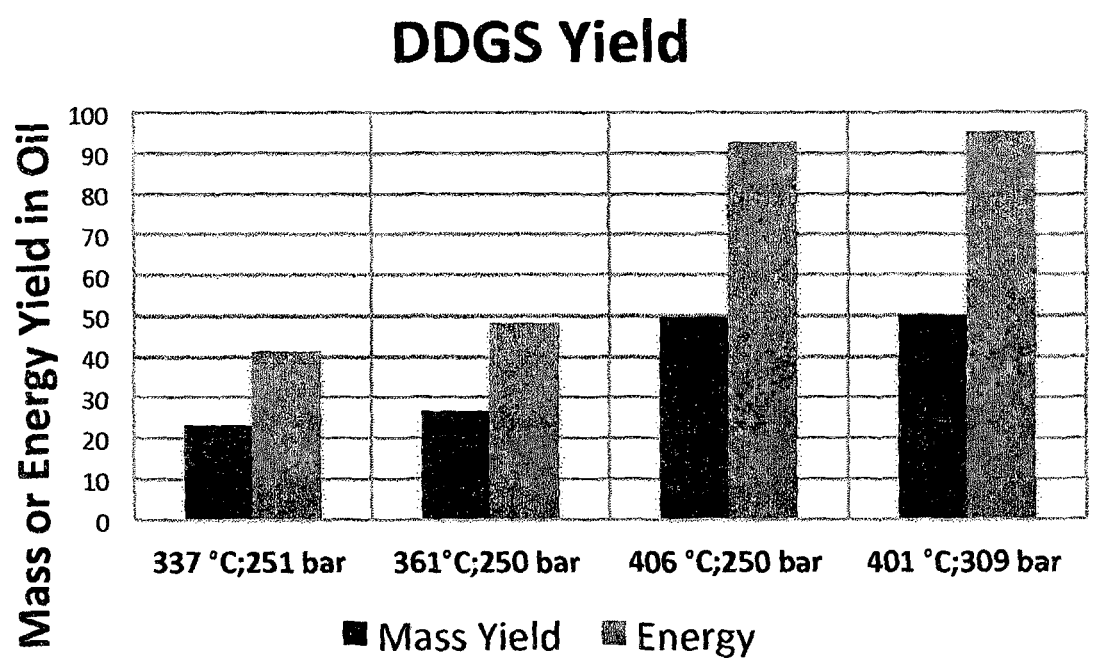
FIG. 17 shows mass- and oil yields obtained for experiments described in example 2.

FIG. 17 shows results for conversion of Dry Distillers Grains with Solubles as described in details in example 2. As seen from the figure significantly yields are obtained at the higher temperatures.

Figure 18:
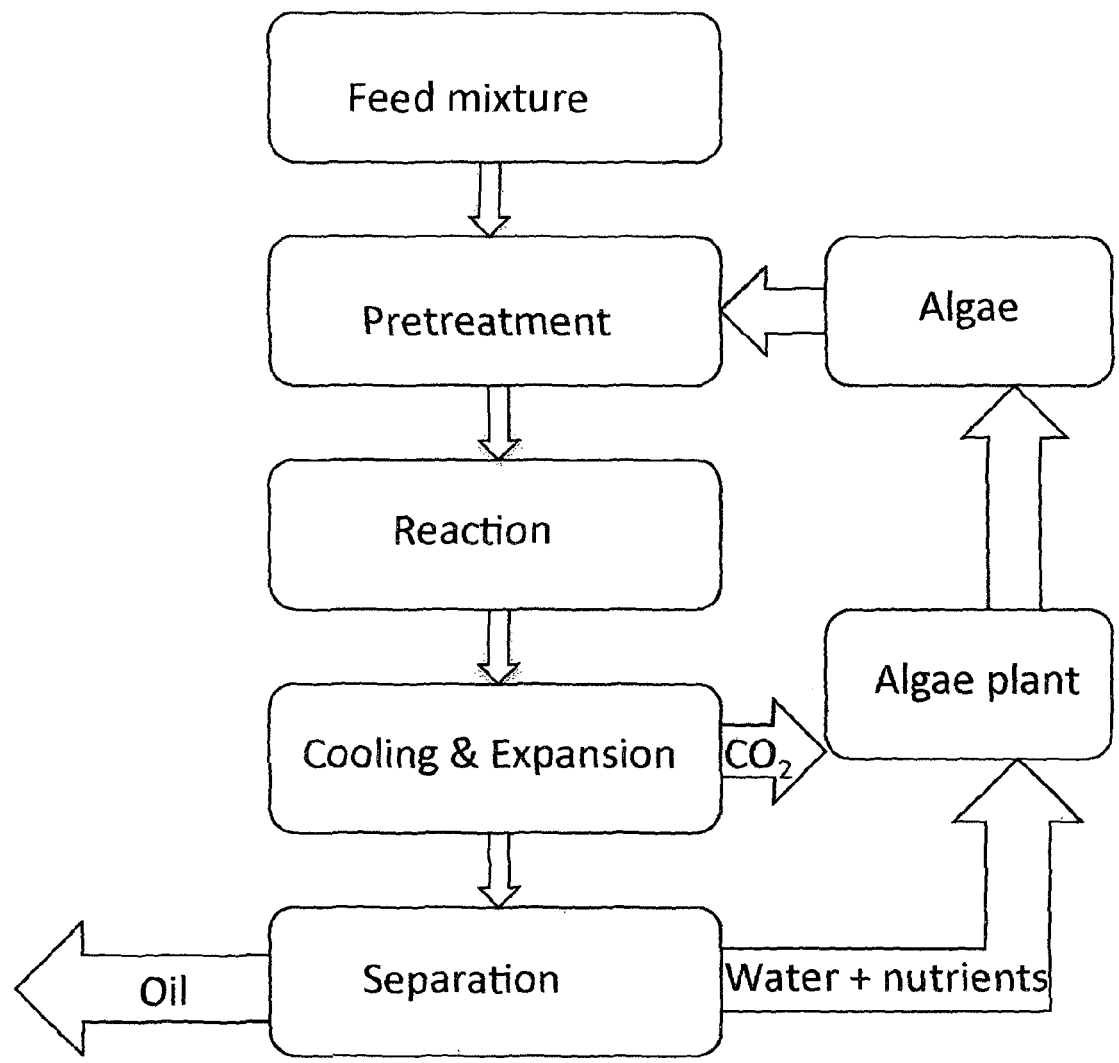
FIG. 18 shows a schematic representation of a conversion plant with an integrated algae plant.

FIG. 18 shows a schematic diagram of a process for conversion of carbonaceous material comprising an integrated algae production plant according to the present invention.

Algae and cyanobacteria (blue-green algae) is attracting enormous attention as the fastest growing biomass on earth, can grow virtually everywhere, high lipid content for some strains and the only biomass which potentially can completely replace fossil fuels.

Various production systems are being developed for cultivation of algae including open and closed ponds, raceways and photobioreactors. Despite the obvious potential of algae and cyanobacteria, production costs are still higher than other biomass. Current issues relates to growing in scale, cost of $CO_2$, and harvesting and extracting the oil. Hence, there is a need for improved and more economical processes for production of oil from algae.

Algae and/or cyanobacteria constitutes an ideal input stream for a process according to the present invention as it is wet and no size reduction is required and further large amounts can be produced directly at site, whereby inbound logistic costs may be eliminated. The lipid content of the algae and/or cyanobacteria is further less important as a process according to the present invention not only extract the lipids from the algae and/or cyanobacteria, but also converts the cell parts of the algae a liquid hydrocarbons. Hence, a process according to the present invention produces more oil and is more efficient than prior art processes. For the same reason a process according to the present invention is less sensitive towards contamination of the specific algae strain than prior art processes.

A particular advantageous embodiment of the present invention is related to co-processing of algae and/or cyanobacteria with other feedstock such as lignite, and/or peat and/or other carbonaceous input streams.

Hence, an aspect of the present invention relates to a process for conversion of carbonaceous materials comprising an integrated algae and/or cyanobacteria production plant.

A preferred embodiment of such process is illustrated in FIG. 18. Carbonaceous material contained in one or more feedstock such as lignite is fed to a first step of pre-treating, wherein it is size reduced to a particle size of less than 30 mm such as less than 3 mm by a milling and/or grinding operation, and mixed with a stream of algae and/or cyanobacteria from said algae and/or cyanobacteria production plant. The algae and/or cyanobacteria production plant may, according to the present invention, comprise open ponds, closed ponds, raceways or photo-bioreactors. The algae and/or bacteria stream fed to said first step of pre-treating is dewatered and concentrated to a paste by mechanical means such as filtration and/or centrifugation such as in a decanter centrifuge prior to being fed to said pretreatment step. The first step of pre-treating may further comprise controlling the concentration of liquid organics and/or the concentration of at least one homogeneous catalyst in the form of potassium and/or sodium to a predefined concentration e.g. by measuring and adding a liquid organic compound and/or at least one homogeneous catalyst in the form of potassium and/or sodium to said feed mixture. Furthermore said pretreatment may comprise controlling the controlling the dry matter content of said feed mixture, the pH value, and preheating said feed mixture as described in relation to FIG. 1.

The feed mixture from said first step of pre-treating step is withdrawn from said first step of pre-treating, and is converted in a second step of converting by first pressurizing the feed mixture to an reaction pressure in the range 100 to 500 bar such as in the range 250 to 350 bar, and subsequently heating it to a reaction temperature in the range 360 to 430° C. such as in the range 370 to 415° C., and maintaining said feed mixture at these reaction conditions for a predefined time e.g. in the range 1 to 60 minutes such as in the range 15 to 40 minutes.

During said second step of converting the feed mixture is decomposed and the oxygen content is reduced by decarboxylation, decarbonylation, hydrogenation and hydrodeoxygenation type of reactions producing a dissolved gas phase comprising carbon dioxide, hydrogen, C1-C4 alkanes and alkenes. Typically the ratio of the weight of gas produced to the weight dry matter in the feed is in the range 15-40%. The majority such as 60 to 95% by volume is comprised by $CO_2$. In a preferred embodiment according to the present invention, the produced $CO_2$ is at least partly recovered and fed to said algae and/or cyanobacteria production plant and used as a carbon source for cultivation of said algae and/or cyanobacteria.

As indicated in FIG. 18 said $CO_2$ recovery is preferably performed during said step of cooling and expanding. In an advantageous embodiment this is performed by first performing said cooling at process pressure by heat exchanging with the incoming feed mixture e.g. to a temperature in the range 100 to 200° C. such as in the range 130 to 160° C. and subsequently expanding the cooled product stream by flashing to a pressure below the critical pressure of $CO_2$ of 74 bar e.g. to a pressure in the range 50-70 bar. Hereby a gas phase comprising dissolved gases such as $CO_2$, $H_2$, C1-C4 alkanes, alkenes, $H_2O$, lower boiling organic compounds such as methanol, ethanol and acetone is produced together with a liquid phase comprising water, liquid hydrocarbons, water soluble organics and suspended and dissolved ash and mineral compounds. The gas phase is preferably cooled and condensed in multiple steps so as to perform a fractionation of the gas phase. In the first step the gas is cooled to a temperature in the range 35 to 80° C. in a first condenser, whereby condensable compounds such as water and lower boiling organic compounds is substantially condensed. Subsequently the gas phase is further cooled to a temperature below the critical temperature of $CO_2$ of 31° C. e.g. in the range 12-30° C. such as in the range 15 to 25° C., whereby $CO_2$ is condensed as liquid $CO_2$ and a high heating value gas is produced. The recovered $CO_2$ is in a liquid form which makes it easier to store and use in said algae and/or cyanobacteria cultivation plant.

The liquid phase from said cooling step is expanded to ambient pressure and cooled to a temperature in the range 25-90° C., and subsequently subjected to a fourth step of separating it into at least a residual fraction and fraction comprising liquid hydrocarbons. Said fourth step of separating preferably comprises separation of said liquid phase in one or more centrifuges.

The residual fraction may in a preferred embodiment according to the present invention subsequently be fed to said algae and/or cyanobacteria plant as shown in FIG. 14, where it may constitute at least part of the growth media for algae and/or cyanobacteria.

The fraction comprising liquid hydrocarbons may further be subjected to a sixth step of upgrading such as described in relation to FIG. 12-15.

The process for conversion of carbonaceous material comprising an integrated algae and/or cyanobacteria production plant according to the present invention possesses a number of advantages over the prior art including:
- The algae and/or cyanobacteria can be processed wet, hence no drying of algae is required or complicated harvesting is required for production of liquid hydrocarbons
- The process according to the present invention is more effective than the prior art as the process also convert the cell parts of the algae and/or cyanobacteria thereby higher hydrocarbon yields can be obtained than in the prior art.
- The process is less dependent on the lipid content of the specific algae and/or cyanobacteria strains. Hence, strains may be selected so as to maximize growth rates rather than lipid content
- Co-processing of carbonaceous materials having a high lignin content such as lignin, lignite, peat, woody biomass etc. with algae and/or cyanobacteria have been found to result in beneficial processing and conversion effects e.g. higher yields of the desired liquid hydrocarbons can be obtained at a lower concentrations of liquid organics added.
- Co-processing of other carbonaceous materials with algae and/or cyanobacteria further enables that the process can be self-sustaining with $CO_2$ for the algae and/or cyanobacteria cultivation thereby reducing a significant production cost
- The $CO_2$ recovery according to the present invention is simple and cheap compared to other $CO_2$ recovery processes which typically use absorption into an amine solution.
- The $CO_2$ recovery process according to the present invention further produces a high heating value gas phase which may be used internally in the process e.g. in the sixth step of upgrading.
- Water from the process containing nutrients is at least partly recycled to said algae and/or cyanobacteria production plant thereby further reducing the production costs of said algae and/or bacteria.
- The recovery and recycle of $CO_2$ and water reduces the $CO_2$ footprint of the process, makes better use of resources and produces less pollutants and waste streams than prior art processes.
- The wet processing of the algae and/or cyanobacteria, the higher yields of hydrocarbons, the recovery and recycle of $CO_2$ and water containing nutrients solves some of the major problems related to cost effective production of algae and/or cyanobacteria in the prior art and results in an overall more effective, energy efficient and economical process for producing liquid hydrocarbons from algae and/or cyanobacteria.

It should be noted that the process of $CO_2$ recovery described in relation to FIG. 18 is generic and may be suitably combined with any of the embodiments according to the present invention.

Example 1: Continuous Flow Vs. Batch Reactors

Batch autoclave type reactors are the most widely used reactor type for hydrothermal research in research labs due to its simplicity and relatively low costs. Handling of the feedstock is easy as it's just placed in the reactor initially. Further pressure let down is easy as the product sample do not need to be removed for pressure let down.

However, some key limitations and differences in the reactor dynamics exist for such systems compared to continuous or semi continuous systems.

One major difference is that heating time to reaction conditions is slow, typically of the order of hours compared to a few minutes. Further the pressure is at least partly dictated by the saturation pressure at the prevailing temperature in the reactor. It should be noted that this fundamentally different from the continuous process according to the present invention, where the input stream is pressurized before heating and the reaction pressure is maintained during all of the heating in the heating step. The pressure during heat up can be increased by adding an initial pressure of an inert gas e.g. $N_2$ or Ar, but in order to be representative for the pressure during heat up according to the present invention the initial pressure needs to be relatively high and will result in venting requirements at reaction temperatures according to the present invention, which means that the atmosphere may be changed and as a consequence results may be difficult to quantify. Still further reaction conditions are typically is specified as the final pressure and temperature. The long heating time and uncontrolled pressure during heat up allows for undesired reactions, and makes it difficult to define a residence time at specific reactions conditions. For the same reasons batch reactor systems may lead to different results and conclusions than the process according to the present invention.

Though not a continuous flow reactor, a stop flow reactor as described above in FIG. 16 eliminates, the limitations with the temperature, pressure and resistance time control in batch reactors systems as the feed mixture can be injected into a pre-heated and pre-pressurized reactor and maintained at these conditions for a predefined reaction time. Hence, though not a continuous flow reactor system such reactor systems are considered to resemble the reaction system according to the present invention close enough to provide useful conversion results.

Example 2: Conversion of DDGS

DDGS was converted in the stop flow reactor described in FIG. 16. Dry Distillers Grain with Solubles the by product from first generation ethanol production and may be considered as a model compound for biomass in the present invention.

Dry distillers grains with solubles from bioethanol production from wheat grains was sourced from Lantmannen Agrotetanol AB, Norrkobing, Sweden. The DDGS supplied as 6 mm pellets and was subquently hammer milled and screened by 0.5 mm screen.

The DDGS mainly consist of protein, cellulose and fibres, but also contains minor amounts of hemicellulos, lipids and starch. The distribution as received from Lantmannen Agroetanol AB is:

| Major components | Wt % as received |
|---|---|
| Moisture | 10 |
| Fibers | 47.5 |
| Cellulose* | 25.4 |
| Lignin* | 6.9 |
| Hemicellulose* | 14.2 |
| Protein | 30.6 |
| Lipids | 5.5 |
| Starch | 1.4 |
| Ash | 5.0 |

*In fibers. Distribution is an estimate and not measured.

A detailed analysis of the DDGS before addition of water and homogneneous catalyst is given in table 2 below. The elemental analysis of the elements C, H and N was determined according to ASTM D 5373. Sulphur was measured according to Swedish standard 187177. The oxygen content was calculated as the balance. Higher and lower heating value as received was measured according to ISO 1928. The moisture content was determined by measuring the weight change by heating at 105° C. over 24 hours, and the ash content was determined as the residue of ignition at 800° C.

|  | DDGS |
|---|---|
| Moisture content (AR), | 9.0 |
| Ash content (AR), | 6.0 |
| C (ASTM D5373), wt % (DAF) | 48.1 |
| H (ASTM D5373), wt % (DAF) | 6.6 |
| N (ASTM D5373), wt % (DAF) | 6.9 |
| S (SS 187177), wt % (DAF) | 1.2 |
| O (Balance), wt % (DAF) | 37.2 |
| HHV (DAF) (ISO1928)), MJ/kg | 20.4 |
| LHV (DAF) (ISO 1928), MJ/kg | 19.5 |

A feed mixture comprising 25% of fry DGGS by weight, 2.5% $K_2CO_3$ by weight and 72.5% water by weight was prepared from the hammer milled and screened DDGS.

The DDGS feed mixture was injected into a preheated and pressurized stop flow reactor as described above, and the feed mixture was maintained at reaction conditions for 15 minutes, whereafter the reactions was quenched by forced cooling with water. After expansion the product was collected in 500 ml centrifuge bottles. The products were allowed to cool, and the liquid hydrocarbon product separated from the water phase by centrifugation for 5 minutes at 8000 rpm in a table centrifuge. The water was removed from the bottle by decanting. The residue comprising liquid hydrocarbon product and particles was diluted with acetone, and subsequently filtered in a vacuum filter. The acetone was removed from the oil by evaporation in a rotary evaporator.

The experimental conditions and results are shown in table below:

Example 3: Recovery of Liquid Organics and Catalyst from Process Water

Water phases from experiment 3 and 4 in example 2 were mixed and 2000 g were concentrated in a rotary evaporator.

In order to maximize the recovery of organics having a boiling point below the boiling point of water, the rotary evaporator was first operated at 60° C. and a pressure of 551 mbar until approximately 10% of the process water was evaporated and recovered in a first distillate The remainder was further concentrated at a temperature of 60° C. and a pressure of 81 mbar. The data for the concentration in the evaporated are shown in the table below:

|  | Amount, g | TOC, g/kg | Total K, g/kg |
|---|---|---|---|
| Process water | 2000 | 21.3 | 22.9 |
| $1^{st}$ distillate | 207 | 34.3 | 0.11 |
| $2^{nd}$ distillate | 1543 | 1.5 | 0.14 |
| Concentrate | 236 | 144 | 199 |
| Concentrate + $1^{st}$ distillate | 443 | 93.6 | 103 |
| Recovery in $1^{st}$ distilliate, % | 10.4 | 16.7 | 0.05 |
| Recovery in $2^{nd}$ distillate | 77.2 | 2.3 | 0.5 |
| Recovery in concentrate, % | 11.8 | 79.8 | 102.5 |
| Total recovery | 99.4 | 98.8 | 103.1 |
| Concentration factor | 4.6 | 4.4 | 4.5 |

The total concentration of carbon (TC) and the total concentration of organic organic carbon (TOC) in the process water before concentrating in the evaporator was measured to 23 g/kg and 21.3 g/kg, respectively. Hence, the majority of the carbon in the liquid phase is comprised by organic carbon. The organic carbon is a complicated mixture alcohols, phenolic compounds, ketones, aldehydes, acids, furans, amines and amides, furans etc. As seen from the table the majority of the liquid organics have a boiling point higher than water with nearly 80% of the total organic carbon being recovered in the concentrate. In general, more than 60% of the organics are typically having a boiling point higher than water.

| Feed mixture | 1<br>25 wt % DDGS | 2<br>25 wt % DDGS | 3<br>25 wt % DDGS | 4<br>25 wt % DDGS |
|---|---|---|---|---|
| $M_{K2CO3}/M_{dry\ matter}$ | 0.1 | 0.1 | 0.1 | 0.1 |
| Reaction temperature, ° C. | 337 | 361 | 406 | 401 |
| Reaction pressure, bar | 251 | 250 | 250 | 309 |
| Residence time, min | 15 | 15 | 15 | 15 |
| Mass yield of oil[1], % | 23.1 | 26.6 | 49.6 | 50.1 |
| Lower heating value of oil, MJ/kg | 34.9 | 35.4 | 36.5 | 37.2 |
| Energy yield of oil[2], % | 41.3 | 48.2 | 92.7 | 95.4 |
| TOC, g/l | 48 | 37 | 23 | 18 |

[1]Mass yield of oil defined as the percentage of dry ash free oil recovered relative to the amount of dry ash free input stream in the feed mixture
[2]Energy yield defined as the percentage of energy recovered in the dry ash free oil relative to the energy content in the dry ash free input stream in the feed mixture As seen from the table and FIG. 17, the mass yield of oil is nearly doubled at a reaction temperature of about 400° C. compared to the mass yield at lower temperature. The carbon content and lower heating value were also found to be higher at the higher temperatures, and the concentration of total organic carbon decreased at the higher temperature.

Visually a clear difference was also observed in the oil produced. Oil produced at the lowest temperature appeared to be viscous and tarry, whereas the oil produced at 360° C. had an appearance like wet paint, whereas the oil produced at about 400° C. appeared to be much lighter and to have a low viscosity.

As further seen from the table about 17% of the have a boiling point lower than for water. Hence, in order to maximize the recovery of liquid organics from the water phase and at the same time clean the water, it is preferred to recover the liquid organics in two fractions e.g. by concentrating the process water using at least two different set of evaporation conditions, whereof at least one set evaporation conditions is selected to result in a distillate with an increased concentration of compounds having a boiling point temperature lower than water and at least one set of evaporation conditions resulting in concentrate with an increased concentration of liquid organics having a boiling point above the boiling point of water. Alternatively, the process water may be concentrated using one set of evaporation conditions and applying at least two sets of condensation conditions with decreasing condensation temperatures. The concentrate and the first distillate or the second condensate may according to the present invention advantageously be mixed as described above and recycled to the pretreatment step according to the present invention.

Finally, it is seen from the table that the recovery of potassium is nearly complete.

Example 4: Conversion of Peat in the Presence of Liquid Organic Compounds

Canadian sphagnum peat moss was converted in the stop flow reactor at a pressure of 240 bar and a temperature 353° C., and at a pressure of 320 bar and 390° C., respectively.

The analysis of the spaghnum peat was:

|  | Spagnum peat moss |
|---|---|
| Moisture content (AR), | 57.0 |
| Ash content (AR), | 22.0 |
| C (ASTM D5373), wt % (DAF) | 51.5 |
| H (ASTM D5373), wt % (DAF) | 4.9 |
| N (ASTM D5373), wt % (DAF) | 4.2 |
| S (SS 187177), wt % (DAF) | 0.9 |
| O (Balance), wt % (DAF) | 38.5 |
| HHV (DAF) (ISO 1928), MJ/kg | 18.9 |
| LHV(DAF) (ISO 1928), MJ/kg | 17.9 |

Spaghnum peat moss was hammer milled and screened to a maximum particle size of 1 mm. 500 g hammer-milled peat was subsequently slurried in a heavy duty planetary mixer by thoroughly mixing it with while adding and mixing it with 175 g of the mixture of the concentrate and distillate of the water phase from experiment 3, 150 g oil produced from DDGS at 360° C., 250 bar, 75 g ethanol, 10 g of NaOH and 5 g of $K_2CO_3$ at a temperature of heating it to about 90° C. The resulting slurry had dry matter content of 25° A) by weight by peat after mixing.

The resulting slurry was injected into the preheated stop flow reactor similarly to the procedure described above in example 2.

| Feed mixture | 5<br>25 wt % Peat | 6<br>25 wt % Peat |
|---|---|---|
| Reaction temperature, ° C. | 353 | 390 |
| Reaction pressure, bar | 240 | 320 |
| Residence time, min | 15 | 20 |
| Mass yield of oil, % | 27.7 | 42.4 |
| Moisture content of oil, wt % | 18.1 | 3.2 |
| Ash content in oil, wt % | 3.6 | 2.2 |
| Conradson carbon residue, wt % |  | 13 |
| Lower heating value of oil (daf), MJ/kg | 32.1 | 37.5 |
| Energy yield of oil, % | 47.0 | 90.9 |

[1]Mass yield of oil defined as the percentage of dry ash free oil produced relative to the amount of dry ash free input stream in the feed mixture
[2]Energy yield defined as the percentage of energy recovered in the dry ash free oil produced relative to the energy content in the dry ash free input stream in the feed mixture

Example 5: Oil Characteristics

The characteristics of the liquid hydrocarbon product produced in experiment 4 and 6 were:

| Feed mixture | 4<br>25 wt % DDGS | 6<br>25 wt % Peat |
|---|---|---|
| Reaction temperature, ° C. | 401 | 390 |
| Reaction pressure, bar | 309 | 320 |
| C, wt % | 79.9 | NA |
| H, wt % | 10.1 | NA |
| N, wt % | 4.9 | NA |
| O, wt % | 4.7 | NA |
| S, wt % | 0.4 | NA |
| Lower heating value (daf), MJ/kg | 37.2 | 37.5 |
| Moisture content, wt % | 2.3 | 1.5 |
| Ash content, wt % | 0.2 | 0.1 |
| Conradson carbon residue number | 10 | 13 |
| Acid number | 32 | NA |
| Density, kg/l | 0.96 | NA |
| Viscosity, cP | 45 | NA |

The boiling point curve was measured by thermogravimetric analysis (TGA) in N2 at a heating rate of 10° C./min:

| Feed mixture | 4<br>25 wt % DDGS | 6<br>25 wt % Peat |
|---|---|---|
| Boiling point: 130 to 230° C. | 25.6 | 42.1 |
| Boiling point: 230-370° C. | 40.8 | 28.5 |
| Boiling point: 370-550° C. | 17.0 | 15.8 |
| Boiling point: >550 Boiling point ° C. | 8.5 | 13.6 |
| Total: | 100.0 | 100.0 |

As seen from the table the majority of the liquid hydrocarbon product had a boiling point in the range 130 to 370° C. (jet fuel+diesel) corresponding to 66.4 and 70.6%, respectively. It should further be noticed that the residue above 550° C. comes close to the Conradson Carbon residue number given in the table above.

Example 6: Upgrading of Oil 200 g of liquid hydrocarbon product produced in experiment 4 was placed in a batch reactor equipped with a condenser. The sample was first heated first to a temperature of 130° C. to remove water and subsequently to a temperature of 550° C. to resemble the two step upgrading procedure according to the present invention. The fractions evaporated at 130° C. and in the range 130 to 550° C. were collected and weighed. A solid black residue was left in the reactor after the evaporation. The results were:

|  | 4 | |
|---|---|---|
|  | g | % |
| Amount evaporated up 130° C., | 5.4 | 2.70 |
| Amount evaporated 130 to 550° C. | 150.5 | 75.25 |
| Water produced 130-550° C. | 8.9 | 4.45 |
| Residue in reactor, | 20.1 | 10.05 |
| Gas produced (Balance) | 15.1 | 7.55 |
| Total | 200.0 | 100.0 |

As seen from the table only a small fraction is evaporated below a temperature 130° C. This fraction is believed mainly comprise water, but only gravimetric analysis was performed.

The majority of the initial mass was recovered as in temperature range 130-550° C. as expected from the boiling point curve measured by TGA above. About 5% water was produced during the heating process in the temperature range 130-550° C. This water is believed to be due to reaction of hydrogen produced by thermal with residual oxygen in the liquid hydrocarbon product. The water form a bottom phase in the product collected and was easily gravimetrically separated from the liquid hydrocarbon product produced. A noncondensable gas was produced during the heating process, particularly at temperatures above 400° C. The gas was found to be combustible by ignition. A black and coke like solid residue was left in the batch reactor after the heating process.

The oil produced was found to be very fluidic and to have a significantly viscosity at room temperature. The liquid hydrocarbon product before and after the upgrading process is compared below.

| Feed mixture | Before upgrading 25 wt % DDGS | After upgrading 25 wt % DDGS |
|---|---|---|
| C, wt % | 79.9 | 80.2 |
| H, wt % | 10.1 | 11.1 |
| N, wt % | 4.9 | 4.5 |
| O, wt % | 4.7 | 3.9 |
| S, wt % | 0.4 | 0.35 |
| Moisture content, wt % | 2.3 | <0.5 |
| Ash content, wt % | 0.2 | NA |
| Higher heating value, MJ/kg | 39.2 | 40.7 |
| Lower heating value, MJ/kg | 37.2 | 38.9 |
| Conradson carbon residue number | 10 | NA |
| Acid number | 32 | 11 |
| Density (22° C.), kg/l | 0.99 | 0.86 |
| Viscosity (60° C.), cP | 48 | 6 |

As seen from the table, at the viscosity, density, acid number, Conradson carbon residue and moisture content are improved by the upgrading by heating.

The invention claimed is:

1. A continuous process for converting carbonaceous material contained in a first feedstock into a liquid hydrocarbon product, said first feedstock, which includes the carbonaceous material, being fed into a feed mixture including one or more fluids, said fluids including comprising water and liquid organic compounds at least partly produced by the process in a concentration of at least 1% by weight, said liquid organic compounds including a second feedstock, the process comprising:
converting at least part of the carbonaceous material by:
pressurising the feed mixture to a pressure in the range 50-400 bar
heating the feed mixture to a temperature in the range 380-500° C., and
maintaining said pressurized and heated feed mixture in the desired pressure and temperature ranges in a reaction zone for a predefined time;
cooling the feed mixture to a temperature in the range 25-200° C. and
expanding the feed mixture to a pressure in the range of 1-70 bar, thereby causing the carbonaceous material to be converted to a liquid hydrocarbon product;
separating a fraction comprising liquid hydrocarbon product, and leaving a residual fraction;
feeding said residual fraction into a bioreactor for the production of biomass including at least one of algae and cyano bacteria, which is a different material than the first feedstock;
wherein said at least one of algae and cyano bacteria is concentrated and recycled to the feed mixture as the second feedstock.

2. A process according to claim 1,
wherein the cooling step, the expanding step, and the separating step are repeated as a series of flash separation steps each resulting in separation of the feed mixture into a gas phase and a liquid phase,
wherein liquid $CO_2$ is recovered from said gas phase, and
wherein the feeding step feeds at least part of the recovered liquid $CO_2$ into the bioreactor.

3. A process according to claim 2, wherein said step of expanding and cooling comprises first cooling said converted feed mixture at process pressure to a temperature in the range 100-200° C. by heat exchange with the incoming feed mixture and subsequently expanding said cooled product stream in one or more steps at least one of said expansion steps comprising an expansion in a flash separator to a pressure in the range 50 to 70 bar, thereby producing a gas phase and a liquid phase, and subsequently cooling the gas phase in a first condenser to a temperature in the range 35 to 80° C., and cooling the gas phase from said first condenser to a temperature in the range 12-30° C., thereby producing a condensate comprising liquid $CO_2$.

4. A process according to claim 3, wherein the converted feed mixture is subject to a further flash expansion at a pressure higher than 70 bar, and at a temperature of at least 300° C.

5. A process according to claim 1, where the process further comprising recovery of substances from the residual fraction remaining after separation of said fraction comprising a liquid hydrocarbon product, and wherein said recovery is performed in one or more evaporators and condensers, and leaving a water fraction, and feeding said water fraction into a bioreactor for the production of biomass such as algae and/or bacteria such as cyano bacteria.

6. A process according to claim 1, where the feed mixture provided contains at least one homogeneous catalyst including potassium and/or sodium so as to ensure a combined concentration of potassium and sodium of at least 0.5% by weight.

7. A process according to claim 1, wherein the ratio of weight of said one or more liquid organic compounds to the dry weight of carbonaceous material in said feed mixture is in the range 0.1 to 2.0.

8. A process according to claim 1, wherein the pressure during said conversion step is in the range 275 to 350 bar.

9. A process according to claim 1, wherein the temperature during said conversion step is in the range 380 to 430° C.

10. A process according to claim 1, wherein the feed mixture at entry temperature is pressurized essentially to the desired process pressure before heating to process temperature is initiated.

11. A process according to claim 1, wherein the pH during said conversion is above 7, wherein the pH of the feed mixture is measured after the conversion, or both during and after the conversion, and when the pH measurement is outside the preferred range, the composition of the feed mixture is altered to correct the pH for subsequent conversion.

12. A process according to claim 1, wherein during the heating of the feed mixture, when the heat of the feed mixture is in the temperature range of 140-300° C., the feed mixture is being heated at a rate of at least 50° C./min.

* * * * *